US011312785B2

(12) United States Patent
Hofmann et al.

(10) Patent No.: US 11,312,785 B2
(45) Date of Patent: Apr. 26, 2022

(54) ANTAGONIZING CD73 ANTIBODY

(71) Applicant: Boehringer Ingelheim International GmbH, Ingelheim am Rhein (DE)

(72) Inventors: Irmgard Maria Rita Hofmann, Vienna (AT); Jennifer Ahlberg, Redding, CT (US); Rajkumar Ganesan, Blue Bell, PA (US); Priyanka Gupta, Danbury, CT (US); Sven Mostboeck, Vienna (AT); Simon Plyte, Como (IT); Otmar Schaaf, Vienna (AT); Chia-Hung Tsai, Danbury, CT (US); Melanie Wurm, Vienna (AT); Markus Zettl, Vienna (AT); Jark Boettcher, Vienna (AT); Bruna De Andrade Pereira, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 258 days.

(21) Appl. No.: 16/409,899

(22) Filed: May 13, 2019

(65) Prior Publication Data

US 2019/0352420 A1 Nov. 21, 2019

(30) Foreign Application Priority Data

May 19, 2018 (EP) .................................... 18173381

(51) Int. Cl.

| | |
|---|---|
| ***A61K 39/00*** | (2006.01) |
| ***C07K 16/28*** | (2006.01) |
| ***A61P 35/00*** | (2006.01) |
| *A61K 45/06* | (2006.01) |

(52) U.S. Cl.

CPC .......... *C07K 16/2896* (2013.01); *A61P 35/00* (2018.01); *C07K 16/2818* (2013.01); *C07K 16/2827* (2013.01); *A61K 45/06* (2013.01); *C07K 2317/54* (2013.01); *C07K 2317/55* (2013.01); *C07K 2317/565* (2013.01); *C07K 2317/75* (2013.01); *C07K 2317/76* (2013.01)

(58) Field of Classification Search

CPC .......... C07K 16/2896; C07K 2317/565; C07K 2317/24; A61P 35/00; A61K 2039/505

See application file for complete search history.

(56) References Cited

U.S. PATENT DOCUMENTS

| | | | |
|---|---|---|---|
| 5,624,821 | A | 4/1997 | Winter et al. |
| 5,648,260 | A | 7/1997 | Winter et al. |

FOREIGN PATENT DOCUMENTS

| | | | |
|---|---|---|---|
| EP | 0388151 | A1 | 9/1990 |
| WO | 8801649 | A1 | 3/1988 |
| WO | 9005144 | A1 | 5/1990 |
| WO | 9117271 | A1 | 11/1991 |
| WO | 09404678 | | 3/1994 |
| WO | 9413804 | A1 | 6/1994 |
| WO | 9429348 | A2 | 12/1994 |
| WO | 9849185 | A1 | 11/1998 |
| WO | 2001079258 | A1 | 10/2001 |
| WO | 2002056910 | A1 | 7/2002 |
| WO | 2003050531 | A2 | 6/2003 |
| WO | 04003019 | A2 | 1/2004 |
| WO | 04081026 | A2 | 9/2004 |
| WO | 06121168 | A1 | 11/2006 |
| WO | 8008449 | | 11/2006 |
| WO | 07042309 | A2 | 4/2007 |
| WO | 0948837 | A1 | 4/2009 |
| WO | 09825971 | A1 | 7/2009 |
| WO | 09101611 | A1 | 8/2009 |
| WO | 09203538 | | 8/2009 |
| WO | 09114335 | A2 | 9/2009 |
| WO | 100266617 | | 10/2010 |
| WO | 11075861 | A1 | 6/2011 |
| WO | 12175741 | A2 | 12/2012 |
| WO | 13024059 | A2 | 2/2013 |
| WO | 15088847 | A1 | 6/2015 |
| WO | 15112900 | A1 | 7/2015 |
| WO | 16055609 | A1 | 4/2016 |
| WO | 2016055609 | | 4/2016 |
| WO | 16075099 | A1 | 5/2016 |
| WO | 16081748 | A2 | 5/2016 |
| WO | 2016075099 | | 5/2016 |
| WO | 2016081748 | | 5/2016 |
| WO | 16131950 | A1 | 8/2016 |
| WO | 17019896 | A1 | 2/2017 |
| WO | 17064043 | A1 | 4/2017 |
| WO | 17100670 | A1 | 6/2017 |
| WO | 2017100670 | | 6/2017 |
| WO | 17152085 | A1 | 9/2017 |
| WO | 17198741 | A1 | 11/2017 |

(Continued)

OTHER PUBLICATIONS

International Search Report for PCT/EP2019/062124 dated Nov. 29, 2019.

Cornen, Immunotherapy of Cancer Conference, The innate Immunity Company next Generation Immunotherapies NK cells and other targets, 2018.

Perrot, Innate Pharma, Preclinical Development of preumanized CD39, 2018.

Geoghan, MABS, Inhibition of CD 73 AMP hydroloysis by a therapeutic antibody, 2016.

Siu, Cancer Research, Preliminary Phase 1 profile of BMS-986179, 2018.

(Continued)

*Primary Examiner* — Sheela J. Huff

(74) *Attorney, Agent, or Firm* — Wendy M. Gombert

(57) ABSTRACT

The present invention relates to novel antagonizing antibodies for CD73. The invention also relates to nucleic acids encoding such antibody molecules; to methods for preparing such antibody molecules; to host cells expressing or capable of expressing such antibody molecules; to compositions comprising such antibody molecules; and to uses of such antibody molecules or such compositions, in particular for therapeutic purposes in the field of cancer diseases.

45 Claims, 4 Drawing Sheets

Specification includes a Sequence Listing.

(56) References Cited

FOREIGN PATENT DOCUMENTS

| | | | |
|---|---|---|---|
| WO | 17199670 | A1 | 11/2017 |
| WO | 18013611 | A1 | 1/2018 |

OTHER PUBLICATIONS

Antonioli, Dept of Clinical Meds, Switching oiff CD73, vol. 22, 2017.
Young, Cancer Cell, Co inhibition of CD73 and A2AR Adenosine Signaling improves Anti tumor immune responses, 2016.
Overman, Journal of Clinical Oncology, Safety, Efficacy and Pharmacodynamics of Medi9447, 2019.
Resta, Oklahoma Medical Research Foundation, Ecto-Enzyme and signaling functions of lymphocyte CD73, 2018.
Billeta, Internattional Reviews of Immunology, Chimeric Antibodies, 1993.
Barbas, Proc. natl. Acad. Sci., In vitro evolutionof a neutralizing human antibody to human immunodeficiency virus type 1, 1994.
Schuck, Molecular INteractions, Size-DistributionAnalysis of macromoleculesbu sedimentation velocity, vol. 78, 2000.
Stafford, Biophysical Chem, Analysis of heterologous interacting systems by sedimentation velocity, vol. 108, 2004.
Knapp, Cell Press, Crystal Structure of the Human Ecto-5'-Nucleotidase CD73, 2012.
Wong, Int. Jour. of Molecular Sci., Assessing the Effects of Acute Myeloid β Oligomer Exposure in the rat, 2016.
Karlin, Proc. Natl. Acad. Sci., Applications and statistics for multiple high scoring segment sin molecular sequences, 1993.
Colgan, Purinergic Signalling, Psyiologocal Roles for ecto-5'nucleotidase, 2006.
Stagg, PNAS, Anti-CD73 antibody therapy inhibits breast tumor growth, 2009.
Karlin, Proc. Natl. Acad. Aci., Metrhods for assessing the statistical significanceof molecular sequence, vol. 87, 1990.
Scier, Gene, Identification of functional and structural amino acid residues, 1996, p. 147-155.
Altshul, J. Mol. Biol., Basic Local Alignment Search Tool, vol. 215, 2000.
Altschul, Nucleic Acids Research, Gapped BLAST and PSI-BLAST: a new generation of protein database search programs, 1997.
Torelli, Cabios, ADVANCE and ADAM; 2 algorithms for the analysis for global similarity betweenhomologous informational sequences, vol. 10, 1994.
Pearson, Proc. Natl. Acad. Sci., Improved tools for biological sequence comparison, vol. 85, 1988.
Higgins, Methods of Enzymology, Using Clustal for multiple sequence alignments, vol. 266, 1996.
Norderhaug, Jour. of Immunological Methods, Versatile vectors for transient and stable and expression of recombinant antibody molecules, 1996.
Kipriyanov, molecular Biotechnology, Generation and Production of Engineered Antibodies, 2004.
Shukla, Journal of Chromatography, Downstream processing of monoclonal antibodies, vol. 848, 2007.
Rippmann, Applied and Environmental Microbiology, Procaryotic Expression of Single Chain Variable Fragment, 1998, p. 4862-4869.
Yamawaki, The Society for Biotechnology, Production of Single CHain Variable Fragment Antobidy (scFv) in Fed Batch and Continuous Culture, vol. 104, 2007.
Sonoda, Protein Expression and purification, Functional Expression of single chain FV antibody, vol. 70, 2010.
Abdiche, Analytical Biochem, Exploring blocking assays using Octet, ProteOn, and Biacore Biosensors, vol. 386, 2009, p. 172-180.
Lofgren, PLOS one, Accurate measurement of endogenous adenosine in human blood, 2018.
Li, Target oncology, A review on various targeted anticancer therapies, vol. 7, 2012.
Hamid, The N.E. Jour. of Medicine, Safety and tumor Respinses with Lambrolizuumab in Melanoma, 2013.
Reichman, MRC Lab of Molecular Biology, Reshaping Human antibodies for Therapy, 1988.
Mark, J. Mol. Biol, By-Passing immunization, vol. 221, 1991.
Knappik, JMB, Fully Synthetic Human Combinatorial Antibody Libraries (HuCal), vol. 296, 2000.
Carmen, CAT, Concepts in antibody phage display, vol. 2, 2003.
Lonberg, International Reviews of immunology, Human Antibodies from transgenic mice, 1995.
Bruggemann, Current opinion in Biotechnology, production of human antibody repertoires in transgenic mice, vol. 8, 1997.
Huston, International reviews of Immunology, Medical Appplications of Single Chain antibodies, 2009.
Ward, Letters to Nature, Binding activities of a repertoire of single immunoglobulin varable domains secreted from a *Escherichia coli*, vol. 341, 1989.
Revets, Expert Opinion on Biological Therapy, Nanobodies as novel agents for cancer therapy, 2005.
Hollinger, Proc. Natl. Acad., Sck., Diabodies: Small Bivalent and bispecific antibody fragments, vol. 90, 1993.
Srinivasan, Current Protein and Peptide Science, immunomodulatory Peptides from IgDF Proteins, vol. 185 2005.
Jin, Micoenvironment and immunology, CD73 on Tumor Cells impairs Antitumor T-cell responses, 2010.
Wang, OnTarget, Prognostic value of CD-73of adenosinergisticpathway in solid tumor, vol. 8, 2017.
Inoue, Oncotarget, Prognostic impact of CD73 and A2A adenosine receptor expression in non small cell lung cancer, vol. 8, 2016.
Antonioli, Dept. of clinical and Experimental Med., Univ of Pisa, Immunity, inflammation and cancer, vol. 13, 2013.
Beavis, Cell Press, CD73: a potent suppressor of antitumor immune responses, vol. 33, 2012.
Hunsucker, Pharmacology and Therapeuctics, The 5-nucleotididases asregulators of nucleotide and drug metabolism, vol. 107, 2005.
Allard, Clinical Cancer Research, Targeting CD73 enhances the antitumor activity of anti-PD 1, 2013.
Tannenbaum, Cancer Biology, Immune Inflammatory Mechanisms in IFN-y mediated anti tumor activity, vol. 10, 2000.
Al-Lazikani, J. Molecular Boil, Standard Conformation for the Canonical Structures of immunoglobulins, vol. 273, 1997.
Mcallum, J. Molecular Biol, Antibody-Antigen interactions, vol. 262, 1996, p. 732-245.
LeFranc, Developmental and Comparative Immunology, IMGT unique numbering for immunoglobulin and T cell receptor variable domains and Ig superfamily V-like domains, 2003, p. 55-57.
Honneger, J. Mole. Biol, Yet another Numbering Scheme for Immunoglobulin Domains, vol. 309, 2001.
Ward, Letters to Nature, Binding Activities of a repertoire of single immunoglobulin variable domains, vol. 341, 1989.
Reichmann, Nature, Reshaping human antibodies for therapy, vol. 332, 1998.

SEQUENCE LISTING

<160> NUMBER OF SEQ ID NOS: 131

<210> SEQ ID NO 1
<211> LENGTH: 10
<212> TYPE: PRT
<213> ORGANISM: Artificial Sequence
<220> FEATURE:
<223> OTHER INFORMATION: A1 - HCDR1

<400> SEQUENCE: 1

Gly Phe Thr Phe Ser His Tyr Tyr Met Ser
1 5 10

<210> SEQ ID NO 2
<211> LENGTH: 17
<212> TYPE: PRT
<213> ORGANISM: Artificial Sequence
<220> FEATURE:
<223> OTHER INFORMATION: A1 - HCDR2

<400> SEQUENCE: 2

Thr Ile Asn Gly Gly Gly Gly Asn Thr Tyr Tyr Pro Asp Ser Val Lys
1 5 10 15

Asp

<210> SEQ ID NO 3
<211> LENGTH: 12
<212> TYPE: PRT
<213> ORGANISM: Artificial Sequence
<220> FEATURE:
<223> OTHER INFORMATION: A1 - HCDR3

<400> SEQUENCE: 3

Gly Gly Pro Tyr Ser Asn Tyr Val Trp Phe Ala Tyr
1 5 10

<210> SEQ ID NO 4
<211> LENGTH: 15
<212> TYPE: PRT
<213> ORGANISM: Artificial Sequence
<220> FEATURE:
<223> OTHER INFORMATION: A1 - LCDR1

<400> SEQUENCE: 4

Arg Ala Ser Gln Ser Val Thr Thr Ser Ser Tyr Thr Tyr Met His
1 5 10 15

<210> SEQ ID NO 5
<211> LENGTH: 7
<212> TYPE: PRT
<213> ORGANISM: Artificial Sequence
<220> FEATURE:
<223> OTHER INFORMATION: A1 - LCDR2

<400> SEQUENCE: 5

Tyr Ala Ser Asn Leu Glu Ser
1 5

<210> SEQ ID NO 6
<211> LENGTH: 9
<212> TYPE: PRT
<213> ORGANISM: Artificial Sequence
<220> FEATURE:
<223> OTHER INFORMATION: A1 - LCDR3

<400> SEQUENCE: 6

```
Gln His Ser Trp Glu Asn Pro Tyr Thr
1               5


<210> SEQ ID NO 7
<211> LENGTH: 10
<212> TYPE: PRT
<213> ORGANISM: Artificial Sequence
<220> FEATURE:
<223> OTHER INFORMATION: A2 - HCDR1

<400> SEQUENCE: 7

Gly Phe Thr Phe Ser Ser Ser Tyr Ile Ser
1               5                   10


<210> SEQ ID NO 8
<211> LENGTH: 17
<212> TYPE: PRT
<213> ORGANISM: Artificial Sequence
<220> FEATURE:
<223> OTHER INFORMATION: A2 - HCDR2

<400> SEQUENCE: 8

Trp Ile Tyr Ala Gly Thr Gly Asn Thr Asn Tyr Asn Gln Lys Phe Thr
1               5                   10                  15

Asp


<210> SEQ ID NO 9
<211> LENGTH: 9
<212> TYPE: PRT
<213> ORGANISM: Artificial Sequence
<220> FEATURE:
<223> OTHER INFORMATION: A2 - HCDR3

<400> SEQUENCE: 9

His Val Asn Trp Asp Tyr Phe Asp Tyr
1               5


<210> SEQ ID NO 10
<211> LENGTH: 11
<212> TYPE: PRT
<213> ORGANISM: Artificial Sequence
<220> FEATURE:
<223> OTHER INFORMATION: A2 - LCDR1

<400> SEQUENCE: 10

Lys Ala Ser Gln Asp Val Gly Thr Ala Val Val
1               5                   10


<210> SEQ ID NO 11
<211> LENGTH: 7
<212> TYPE: PRT
<213> ORGANISM: Artificial Sequence
<220> FEATURE:
<223> OTHER INFORMATION: A2 - LCDR2

<400> SEQUENCE: 11

Trp Ala Ser Ser Arg His Thr
1               5


<210> SEQ ID NO 12
<211> LENGTH: 9
<212> TYPE: PRT
<213> ORGANISM: Artificial Sequence
<220> FEATURE:
<223> OTHER INFORMATION: A2 - LCDR3

<400> SEQUENCE: 12
```

```
Gln Gln Tyr Arg Ser Tyr Pro Trp Thr
1               5


<210> SEQ ID NO 13
<211> LENGTH: 10
<212> TYPE: PRT
<213> ORGANISM: Artificial Sequence
<220> FEATURE:
<223> OTHER INFORMATION: A3 - HCDR1

<400> SEQUENCE: 13

Gly Tyr Thr Phe Thr Thr Tyr Trp Met His
1               5                   10


<210> SEQ ID NO 14
<211> LENGTH: 17
<212> TYPE: PRT
<213> ORGANISM: Artificial Sequence
<220> FEATURE:
<223> OTHER INFORMATION: A3 - HCDR2

<400> SEQUENCE: 14

Ala Ile Tyr Pro Gly Asn Ser Asp Thr Thr Tyr Asn Gln Lys Phe Lys
1               5                   10                  15

Gly


<210> SEQ ID NO 15
<211> LENGTH: 8
<212> TYPE: PRT
<213> ORGANISM: Artificial Sequence
<220> FEATURE:
<223> OTHER INFORMATION: A3 - HCDR3

<400> SEQUENCE: 15

Leu Leu Asp Tyr Ala Met Asp Tyr
1               5


<210> SEQ ID NO 16
<211> LENGTH: 11
<212> TYPE: PRT
<213> ORGANISM: Artificial Sequence
<220> FEATURE:
<223> OTHER INFORMATION: A3 - LCDR1

<400> SEQUENCE: 16

Arg Ala Ser Gln Asp Ile Arg Asn Tyr Leu Asn
1               5                   10


<210> SEQ ID NO 17
<211> LENGTH: 7
<212> TYPE: PRT
<213> ORGANISM: Artificial Sequence
<220> FEATURE:
<223> OTHER INFORMATION: A3 - LCDR2

<400> SEQUENCE: 17

Tyr Thr Ser Arg Leu His Ser
1               5


<210> SEQ ID NO 18
<211> LENGTH: 9
<212> TYPE: PRT
<213> ORGANISM: Artificial Sequence
<220> FEATURE:
<223> OTHER INFORMATION: A3 - LCDR3
```

<400> SEQUENCE: 18

Gln Gln Gly Asn Thr Leu Pro Trp Thr
1 5

<210> SEQ ID NO 19
<211> LENGTH: 10
<212> TYPE: PRT
<213> ORGANISM: Artificial Sequence
<220> FEATURE:
<223> OTHER INFORMATION: A4 - HCDR1

<400> SEQUENCE: 19

Gly Leu Thr Phe Ser Ser Tyr Val Met Ser
1 5 10

<210> SEQ ID NO 20
<211> LENGTH: 17
<212> TYPE: PRT
<213> ORGANISM: Artificial Sequence
<220> FEATURE:
<223> OTHER INFORMATION: A4 - HCDR2

<400> SEQUENCE: 20

Thr Ile Ser Ser Gly Gly Val Ser Thr Tyr Tyr Pro Asp Thr Val Lys
1 5 10 15

Gly

<210> SEQ ID NO 21
<211> LENGTH: 11
<212> TYPE: PRT
<213> ORGANISM: Artificial Sequence
<220> FEATURE:
<223> OTHER INFORMATION: A4 - HCDR3

<400> SEQUENCE: 21

Arg Glu Thr Ala Arg Ala Thr Gly Phe Ala Tyr
1 5 10

<210> SEQ ID NO 22
<211> LENGTH: 11
<212> TYPE: PRT
<213> ORGANISM: Artificial Sequence
<220> FEATURE:
<223> OTHER INFORMATION: A4 - LCDR1

<400> SEQUENCE: 22

Lys Ala Ser Gln Ser Val Ser Asn Asp Val Thr
1 5 10

<210> SEQ ID NO 23
<211> LENGTH: 7
<212> TYPE: PRT
<213> ORGANISM: Artificial Sequence
<220> FEATURE:
<223> OTHER INFORMATION: A4 - LCDR2

<400> SEQUENCE: 23

Tyr Ala Ser Asn Arg Tyr Thr
1 5

<210> SEQ ID NO 24
<211> LENGTH: 9
<212> TYPE: PRT
<213> ORGANISM: Artificial Sequence
<220> FEATURE:
<223> OTHER INFORMATION: A4 - LCDR3

<400> SEQUENCE: 24

Gln Gln Asp Tyr Ser Ser Pro Trp Thr
1 5

<210> SEQ ID NO 25
<211> LENGTH: 10
<212> TYPE: PRT
<213> ORGANISM: Artificial Sequence
<220> FEATURE:
<223> OTHER INFORMATION: B1 - HCDR1

<400> SEQUENCE: 25

Gly Leu Thr Phe Ser Ser Tyr Val Met Ser
1 5 10

<210> SEQ ID NO 26
<211> LENGTH: 17
<212> TYPE: PRT
<213> ORGANISM: Artificial Sequence
<220> FEATURE:
<223> OTHER INFORMATION: B1 - HCDR2

<400> SEQUENCE: 26

Thr Ile Ser Ser Gly Gly Val Ser Thr Tyr Tyr Pro Asp Thr Val Lys
1 5 10 15

Gly

<210> SEQ ID NO 27
<211> LENGTH: 11
<212> TYPE: PRT
<213> ORGANISM: Artificial Sequence
<220> FEATURE:
<223> OTHER INFORMATION: B1 - HCDR3

<400> SEQUENCE: 27

Arg Glu Thr Ala Arg Ala Thr Gly Phe Ala Tyr
1 5 10

<210> SEQ ID NO 28
<211> LENGTH: 11
<212> TYPE: PRT
<213> ORGANISM: Artificial Sequence
<220> FEATURE:
<223> OTHER INFORMATION: B1 - LCDR1

<400> SEQUENCE: 28

Lys Ala Ser Gln Ser Val Ser Asn Asp Val Thr
1 5 10

<210> SEQ ID NO 29
<211> LENGTH: 7
<212> TYPE: PRT
<213> ORGANISM: Artificial Sequence
<220> FEATURE:
<223> OTHER INFORMATION: B1 - LCDR2

<400> SEQUENCE: 29

Tyr Ala Ser Asn Arg Tyr Thr
1 5

<210> SEQ ID NO 30
<211> LENGTH: 9
<212> TYPE: PRT
<213> ORGANISM: Artificial Sequence
<220> FEATURE:

<223> OTHER INFORMATION: B1 - LCDR3

<400> SEQUENCE: 30

Gln Gln Asp Tyr Ser Ser Pro Trp Thr
1 5

<210> SEQ ID NO 31
<211> LENGTH: 10
<212> TYPE: PRT
<213> ORGANISM: Artificial Sequence
<220> FEATURE:
<223> OTHER INFORMATION: B2 - HCDR1

<400> SEQUENCE: 31

Gly Leu Thr Phe Ser Ser Tyr Val Met Ser
1 5 10

<210> SEQ ID NO 32
<211> LENGTH: 17
<212> TYPE: PRT
<213> ORGANISM: Artificial Sequence
<220> FEATURE:
<223> OTHER INFORMATION: B2 - HCDR2

<400> SEQUENCE: 32

Thr Ile Ser Ser Gly Gly Val Ser Thr Tyr Tyr Pro Asp Thr Val Lys
1 5 10 15

Gly

<210> SEQ ID NO 33
<211> LENGTH: 11
<212> TYPE: PRT
<213> ORGANISM: Artificial Sequence
<220> FEATURE:
<223> OTHER INFORMATION: B2 - HCDR3

<400> SEQUENCE: 33

Arg Glu Thr Ala Arg Ala Thr Gly Phe Ala Tyr
1 5 10

<210> SEQ ID NO 34
<211> LENGTH: 11
<212> TYPE: PRT
<213> ORGANISM: Artificial Sequence
<220> FEATURE:
<223> OTHER INFORMATION: B2 - LCDR1

<400> SEQUENCE: 34

Lys Ala Ser Gln Ser Val Ser Asp Asp Val Thr
1 5 10

<210> SEQ ID NO 35
<211> LENGTH: 7
<212> TYPE: PRT
<213> ORGANISM: Artificial Sequence
<220> FEATURE:
<223> OTHER INFORMATION: B2 - LCDR2

<400> SEQUENCE: 35

Tyr Ala Ser Asn Arg Tyr Thr
1 5

<210> SEQ ID NO 36
<211> LENGTH: 9
<212> TYPE: PRT
<213> ORGANISM: Artificial Sequence

<220> FEATURE:
<223> OTHER INFORMATION: B2 - LCDR3

<400> SEQUENCE: 36

Gln Gln Asp Tyr Ser Ser Pro Trp Thr
1               5

<210> SEQ ID NO 37
<211> LENGTH: 10
<212> TYPE: PRT
<213> ORGANISM: Artificial Sequence
<220> FEATURE:
<223> OTHER INFORMATION: C1 - HCDR1

<400> SEQUENCE: 37

Gly Tyr Thr Phe Thr Thr Tyr Trp Met His
1               5                   10

<210> SEQ ID NO 38
<211> LENGTH: 17
<212> TYPE: PRT
<213> ORGANISM: Artificial Sequence
<220> FEATURE:
<223> OTHER INFORMATION: C1 - HCDR2

<400> SEQUENCE: 38

Ala Ile Tyr Pro Gly Phe Ser Asp Thr Thr Tyr Ser Gln Lys Phe Lys
1               5                   10                  15

Gly

<210> SEQ ID NO 39
<211> LENGTH: 8
<212> TYPE: PRT
<213> ORGANISM: Artificial Sequence
<220> FEATURE:
<223> OTHER INFORMATION: C1 - HCDR3

<400> SEQUENCE: 39

Leu Leu Asp Tyr Ala Met Asp Tyr
1               5

<210> SEQ ID NO 40
<211> LENGTH: 11
<212> TYPE: PRT
<213> ORGANISM: Artificial Sequence
<220> FEATURE:
<223> OTHER INFORMATION: C1 - LCDR1

<400> SEQUENCE: 40

Arg Ala Ser Gln Asp Ile Arg Ser Tyr Leu Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: C1 - LCDR2

<400> SEQUENCE: 41

Tyr Thr Ser Arg Leu His Ser
1               5

<210> SEQ ID NO 42
<211> LENGTH: 9
<212> TYPE: PRT

```
<213> ORGANISM: Artificial Sequence
<220> FEATURE:
<223> OTHER INFORMATION: C1 - LCDR3

<400> SEQUENCE: 42

Gln Gln Gly Glu Thr Leu Pro Trp Thr
1               5


<210> SEQ ID NO 43
<211> LENGTH: 10
<212> TYPE: PRT
<213> ORGANISM: Artificial Sequence
<220> FEATURE:
<223> OTHER INFORMATION: C2 - HCDR1

<400> SEQUENCE: 43

Gly Tyr Thr Phe Thr Thr Tyr Trp Met His
1               5                   10


<210> SEQ ID NO 44
<211> LENGTH: 17
<212> TYPE: PRT
<213> ORGANISM: Artificial Sequence
<220> FEATURE:
<223> OTHER INFORMATION: C2 - HCDR2

<400> SEQUENCE: 44

Ala Ile Tyr Pro Gly Leu Ser Asp Thr Thr Tyr Ser Gln Lys Phe Lys
1               5                   10                  15

Gly


<210> SEQ ID NO 45
<211> LENGTH: 8
<212> TYPE: PRT
<213> ORGANISM: Artificial Sequence
<220> FEATURE:
<223> OTHER INFORMATION: C2 - HCDR3

<400> SEQUENCE: 45

Leu Leu Asp Tyr Ala Met Asp Tyr
1               5


<210> SEQ ID NO 46
<211> LENGTH: 11
<212> TYPE: PRT
<213> ORGANISM: Artificial Sequence
<220> FEATURE:
<223> OTHER INFORMATION: C2 - LCDR1

<400> SEQUENCE: 46

Arg Ala Ser Gln Asp Ile Arg Ser Tyr Leu Asn
1               5                   10


<210> SEQ ID NO 47
<211> LENGTH: 7
<212> TYPE: PRT
<213> ORGANISM: Artificial Sequence
<220> FEATURE:
<223> OTHER INFORMATION: C2 - LCDR2

<400> SEQUENCE: 47

Tyr Thr Ser Arg Leu His Ser
1               5


<210> SEQ ID NO 48
<211> LENGTH: 9
```

```
<212> TYPE: PRT
<213> ORGANISM: Artificial Sequence
<220> FEATURE:
<223> OTHER INFORMATION: C2 - LCDR3

<400> SEQUENCE: 48

Gln Gln Gly Glu Thr Leu Pro Trp Thr
1               5


<210> SEQ ID NO 49
<211> LENGTH: 10
<212> TYPE: PRT
<213> ORGANISM: Artificial Sequence
<220> FEATURE:
<223> OTHER INFORMATION: C3 - HCDR1

<400> SEQUENCE: 49

Gly Tyr Thr Phe Thr Thr Tyr Trp Met His
1               5                   10


<210> SEQ ID NO 50
<211> LENGTH: 17
<212> TYPE: PRT
<213> ORGANISM: Artificial Sequence
<220> FEATURE:
<223> OTHER INFORMATION: C3 - HCDR2

<400> SEQUENCE: 50

Ala Ile Tyr Pro Gly Leu Ser Asp Thr Thr Tyr Ser Gln Lys Phe Lys
1               5                   10                  15

Gly


<210> SEQ ID NO 51
<211> LENGTH: 8
<212> TYPE: PRT
<213> ORGANISM: Artificial Sequence
<220> FEATURE:
<223> OTHER INFORMATION: C3 - HCDR3

<400> SEQUENCE: 51

Leu Leu Asp Tyr Ala Met Asp Tyr
1               5


<210> SEQ ID NO 52
<211> LENGTH: 11
<212> TYPE: PRT
<213> ORGANISM: Artificial Sequence
<220> FEATURE:
<223> OTHER INFORMATION: C3 - LCDR1

<400> SEQUENCE: 52

Arg Ala Ser Gln Asp Ile Arg Ser Tyr Leu Asn
1               5                   10


<210> SEQ ID NO 53
<211> LENGTH: 7
<212> TYPE: PRT
<213> ORGANISM: Artificial Sequence
<220> FEATURE:
<223> OTHER INFORMATION: C3 - LCDR2

<400> SEQUENCE: 53

Tyr Thr Ser Arg Leu His Ser
1               5


<210> SEQ ID NO 54
```

<211> LENGTH: 9
<212> TYPE: PRT
<213> ORGANISM: Artificial Sequence
<220> FEATURE:
<223> OTHER INFORMATION: C3 - LCDR3

<400> SEQUENCE: 54

Gln Gln Gly Glu Thr Leu Pro Trp Thr
1 5

<210> SEQ ID NO 55
<211> LENGTH: 10
<212> TYPE: PRT
<213> ORGANISM: Artificial Sequence
<220> FEATURE:
<223> OTHER INFORMATION: C4 - HCDR1

<400> SEQUENCE: 55

Gly Tyr Thr Phe Thr Thr Tyr Trp Met His
1 5 10

<210> SEQ ID NO 56
<211> LENGTH: 17
<212> TYPE: PRT
<213> ORGANISM: Artificial Sequence
<220> FEATURE:
<223> OTHER INFORMATION: C4 - HCDR2

<400> SEQUENCE: 56

Ala Ile Tyr Pro Gly Leu Ser Asp Thr Thr Tyr Asn Gln Lys Phe Lys
1 5 10 15

Gly

<210> SEQ ID NO 57
<211> LENGTH: 8
<212> TYPE: PRT
<213> ORGANISM: Artificial Sequence
<220> FEATURE:
<223> OTHER INFORMATION: C4 - HCDR3

<400> SEQUENCE: 57

Leu Leu Asp Tyr Ala Met Asp Tyr
1 5

<210> SEQ ID NO 58
<211> LENGTH: 11
<212> TYPE: PRT
<213> ORGANISM: Artificial Sequence
<220> FEATURE:
<223> OTHER INFORMATION: C4 - LCDR1

<400> SEQUENCE: 58

Arg Ala Ser Gln Asp Ile Arg Ser Tyr Leu Asn
1 5 10

<210> SEQ ID NO 59
<211> LENGTH: 7
<212> TYPE: PRT
<213> ORGANISM: Artificial Sequence
<220> FEATURE:
<223> OTHER INFORMATION: C4 - LCDR2

<400> SEQUENCE: 59

Tyr Thr Ser Arg Leu His Ser
1 5

<210> SEQ ID NO 60
<211> LENGTH: 9
<212> TYPE: PRT
<213> ORGANISM: Artificial Sequence
<220> FEATURE:
<223> OTHER INFORMATION: C4 - LCDR3

<400> SEQUENCE: 60

Gln Gln Gly Glu Thr Leu Pro Trp Thr
1 5

<210> SEQ ID NO 61
<211> LENGTH: 10
<212> TYPE: PRT
<213> ORGANISM: Artificial Sequence
<220> FEATURE:
<223> OTHER INFORMATION: C5 - HCDR1

<400> SEQUENCE: 61

Gly Tyr Thr Phe Thr Thr Tyr Trp Met His
1 5 10

<210> SEQ ID NO 62
<211> LENGTH: 17
<212> TYPE: PRT
<213> ORGANISM: Artificial Sequence
<220> FEATURE:
<223> OTHER INFORMATION: C5 - HCDR2

<400> SEQUENCE: 62

Ala Ile Tyr Pro Gly Asn Ser Asp Thr Thr Tyr Asn Gln Lys Phe Lys
1 5 10 15

Gly

<210> SEQ ID NO 63
<211> LENGTH: 8
<212> TYPE: PRT
<213> ORGANISM: Artificial Sequence
<220> FEATURE:
<223> OTHER INFORMATION: C5 - HCDR3

<400> SEQUENCE: 63

Leu Leu Asp Tyr Ala Met Asp Tyr
1 5

<210> SEQ ID NO 64
<211> LENGTH: 11
<212> TYPE: PRT
<213> ORGANISM: Artificial Sequence
<220> FEATURE:
<223> OTHER INFORMATION: C5 - LCDR1

<400> SEQUENCE: 64

Arg Ala Ser Gln Asp Ile Arg Ser Tyr Leu Asn
1 5 10

<210> SEQ ID NO 65
<211> LENGTH: 7
<212> TYPE: PRT
<213> ORGANISM: Artificial Sequence
<220> FEATURE:
<223> OTHER INFORMATION: C5 - LCDR2

<400> SEQUENCE: 65

Tyr Thr Ser Arg Leu His Ser
1 5

<210> SEQ ID NO 66
<211> LENGTH: 9
<212> TYPE: PRT
<213> ORGANISM: Artificial Sequence
<220> FEATURE:
<223> OTHER INFORMATION: C5 - LCDR3

<400> SEQUENCE: 66

Gln Gln Gly Glu Thr Leu Pro Trp Thr
1 5

<210> SEQ ID NO 67
<211> LENGTH: 10
<212> TYPE: PRT
<213> ORGANISM: Artificial Sequence
<220> FEATURE:
<223> OTHER INFORMATION: C6 - HCDR1

<400> SEQUENCE: 67

Gly Tyr Thr Phe Thr Thr Tyr Trp Met His
1 5 10

<210> SEQ ID NO 68
<211> LENGTH: 17
<212> TYPE: PRT
<213> ORGANISM: Artificial Sequence
<220> FEATURE:
<223> OTHER INFORMATION: C6 - HCDR2

<400> SEQUENCE: 68

Ala Ile Tyr Pro Gly Asn Ser Asp Thr Thr Tyr Asn Gln Lys Phe Lys
1 5 10 15

Gly

<210> SEQ ID NO 69
<211> LENGTH: 8
<212> TYPE: PRT
<213> ORGANISM: Artificial Sequence
<220> FEATURE:
<223> OTHER INFORMATION: C6 - HCDR3

<400> SEQUENCE: 69

Leu Leu Asp Tyr Ala Met Asp Tyr
1 5

<210> SEQ ID NO 70
<211> LENGTH: 11
<212> TYPE: PRT
<213> ORGANISM: Artificial Sequence
<220> FEATURE:
<223> OTHER INFORMATION: C6 - LCDR1

<400> SEQUENCE: 70

Arg Ala Ser Gln Asp Ile Arg Asn Tyr Leu Asn
1 5 10

<210> SEQ ID NO 71
<211> LENGTH: 7
<212> TYPE: PRT
<213> ORGANISM: Artificial Sequence
<220> FEATURE:
<223> OTHER INFORMATION: C6 - LCDR2

<400> SEQUENCE: 71

Tyr Thr Ser Arg Leu His Ser
1 5

<210> SEQ ID NO 72
<211> LENGTH: 9
<212> TYPE: PRT
<213> ORGANISM: Artificial Sequence
<220> FEATURE:
<223> OTHER INFORMATION: C6 - LCDR3

<400> SEQUENCE: 72

```
Gln Gln Gly Asn Thr Leu Pro Trp Thr
1               5
```

<210> SEQ ID NO 73
<211> LENGTH: 121
<212> TYPE: PRT
<213> ORGANISM: Artificial Sequence
<220> FEATURE:
<223> OTHER INFORMATION: A1 - VH

<400> SEQUENCE: 73

```
Asp Val Lys Leu Val Glu Ser Gly Gly Gly Leu Val Lys Leu Gly Gly
1               5                   10                  15

Ser Leu Lys Leu Ser Cys Val Ala Ser Gly Phe Thr Phe Ser His Tyr
            20                  25                  30

Tyr Met Ser Trp Ile Arg Gln Thr Pro Glu Lys Arg Leu Glu Trp Val
        35                  40                  45

Ala Thr Ile Asn Gly Gly Gly Gly Asn Thr Tyr Tyr Pro Asp Ser Val
    50                  55                  60

Lys Asp Arg Phe Thr Ile Ser Arg Asp Asn Ala Lys Asn Thr Leu Tyr
65                  70                  75                  80

Leu Gln Met Ser Ser Leu Asn Ser Glu Asp Thr Ala Val Tyr Tyr Cys
                85                  90                  95

Ala Arg Gly Gly Pro Tyr Ser Asn Tyr Val Trp Phe Ala Tyr Trp Gly
            100                 105                 110

Gln Gly Thr Leu Val Thr Val Ser Ala
        115                 120
```

<210> SEQ ID NO 74
<211> LENGTH: 111
<212> TYPE: PRT
<213> ORGANISM: Artificial Sequence
<220> FEATURE:
<223> OTHER INFORMATION: A1 - VL

<400> SEQUENCE: 74

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Thr Thr Ser
            20                  25                  30

Ser Tyr Thr Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Ile Tyr Tyr Cys Gln His Ser Trp
                85                  90                  95

Glu Asn Pro Tyr Thr Phe Gly Gly Gly Thr Lys Leu Glu Ile Lys
            100                 105                 110
```

<210> SEQ ID NO 75
<211> LENGTH: 118
<212> TYPE: PRT
<213> ORGANISM: Artificial Sequence
<220> FEATURE:
<223> OTHER INFORMATION: A2 - VH

<400> SEQUENCE: 75

```
Gln Gly Gln Met Gln Gln Ser Gly Ala Glu Leu Val Lys Pro Gly Thr
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Arg Pro Arg Gln Ser Leu Glu Trp Ile
        35                  40                  45

Ala Trp Ile Tyr Ala Gly Thr Gly Asn Thr Asn Tyr Asn Gln Lys Phe
    50                  55                  60

Thr Asp Lys Ala Gln Val Thr Val Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg His Val Asn Trp Asp Tyr Phe Asp Tyr Trp Gly Gln Gly Thr
            100                 105                 110

Thr Leu Thr Val Ser Ser
        115
```

<210> SEQ ID NO 76
<211> LENGTH: 107
<212> TYPE: PRT
<213> ORGANISM: Artificial Sequence
<220> FEATURE:
<223> OTHER INFORMATION: A2 - VL

<400> SEQUENCE: 76

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Val Trp Tyr Gln Gln Lys Pro Gly Gln Ser Pro Lys Leu Leu Ile
        35                  40                  45

Tyr Trp Ala Ser Ser Arg His Thr Gly Val Pro Asp Arg Phe Thr Gly
    50                  55                  60

Ser Gly Ser Gly Thr Asp Phe Thr Leu Thr Leu Thr Asn Val Gln Ser
65                  70                  75                  80

Glu Asp Leu Ala Asp Tyr Phe Cys Gln Gln Tyr Arg Ser Tyr Pro Trp
                85                  90                  95

Thr Phe Gly Gly Gly Thr Asn Leu Glu Ile Lys
            100                 105
```

<210> SEQ ID NO 77
<211> LENGTH: 117
<212> TYPE: PRT
<213> ORGANISM: Artificial Sequence
<220> FEATURE:
<223> OTHER INFORMATION: A3 - VH

<400> SEQUENCE: 77

```
Glu Val Gln Leu Gln Gln Ser Gly Thr Val Leu Ala Arg Pro Gly Asp
1               5                   10                  15

Ser Val Lys Met Ser Cys Lys Thr Ser Gly Tyr Thr Phe Thr Thr Tyr
```

```
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Thr Tyr Asn Gln Lys Phe
    50                  55                  60

Lys Gly Lys Ala Lys Leu Thr Ala Val Thr Ser Ala Ser Thr Ala Tyr
65                  70                  75                  80

Met Lys Leu Ser Ser Leu Thr Asn Glu Asp Ser Ala Val Tyr Tyr Cys
                85                  90                  95

Thr Arg Leu Leu Asp Tyr Ala Met Asp Tyr Trp Gly Gln Gly Thr Ser
            100                 105                 110

Val Thr Val Ser Ser
        115


<210> SEQ ID NO 78
<211> LENGTH: 107
<212> TYPE: PRT
<213> ORGANISM: Artificial Sequence
<220> FEATURE:
<223> OTHER INFORMATION: A3 - VL

<400> SEQUENCE: 78

Glu Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp His Gln Gln Lys Pro Asp Gly Thr Val Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105


<210> SEQ ID NO 79
<211> LENGTH: 120
<212> TYPE: PRT
<213> ORGANISM: Artificial Sequence
<220> FEATURE:
<223> OTHER INFORMATION: A4 - VH

<400> SEQUENCE: 79

Glu Val Gln Leu Val Glu Ser Gly Gly Gly Leu Val Lys Pro Gly Gly
1               5                   10                  15

Ser Leu Lys Leu Ser Cys Ala Ala Ser Gly Leu Thr Phe Ser Ser Tyr
            20                  25                  30

Val Met Ser Trp Val Arg Gln Thr Pro Ala Lys Arg Leu Glu Trp Val
        35                  40                  45

Ala Thr Ile Ser Ser Gly Gly Val Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Met Ser Glu Asp Thr Ala Met Tyr Tyr Cys
                85                  90                  95
```

```
Ala Arg Arg Glu Thr Ala Arg Ala Thr Gly Phe Ala Tyr Trp Gly Gln
            100                 105                 110

Gly Thr Leu Val Thr Val Ser Ala
        115                 120


<210> SEQ ID NO 80
<211> LENGTH: 107
<212> TYPE: PRT
<213> ORGANISM: Artificial Sequence
<220> FEATURE:
<223> OTHER INFORMATION: A4 - VL

<400> SEQUENCE: 80

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Thr Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Asn Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105


<210> SEQ ID NO 81
<211> LENGTH: 120
<212> TYPE: PRT
<213> ORGANISM: Artificial Sequence
<220> FEATURE:
<223> OTHER INFORMATION: B1 - VH

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Val Met Ser Trp Val Arg Gln Ala Pro Gly Lys Gly Leu Glu Trp Val
        35                  40                  45

Ser Thr Ile Ser Ser Gly Gly Val Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Glu Thr Ala Arg Ala Thr Gly Phe Ala Tyr Trp Gly Gln
            100                 105                 110

Gly Thr Leu Val Thr Val Ser Ala
        115                 120


<210> SEQ ID NO 82
<211> LENGTH: 107
<212> TYPE: PRT
<213> ORGANISM: Artificial Sequence
<220> FEATURE:
<223> OTHER INFORMATION: B1 - VL
```

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Thr Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Val Gln Pro
65                  70                  75                  80

Glu Asp Ile Ala Thr Tyr Tyr Cys Gln Gln Asp Tyr Ser Ser Pro Trp
                85                  90                  95

Thr Phe Gly Gly Gly Thr Lys Leu Glu Ile Lys
            100                 105
```

<210> SEQ ID NO 83
<211> LENGTH: 120
<212> TYPE: PRT
<213> ORGANISM: Artificial Sequence
<220> FEATURE:
<223> OTHER INFORMATION: B2 - VH

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Val Met Ser Trp Val Arg Gln Ala Pro Gly Lys Gly Leu Glu Trp Val
        35                  40                  45

Ser Thr Ile Ser Ser Gly Gly Val Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Glu Thr Ala Arg Ala Thr Gly Phe Ala Tyr Trp Gly Gln
            100                 105                 110

Gly Thr Leu Val Thr Val Ser Ala
        115                 120
```

<210> SEQ ID NO 84
<211> LENGTH: 107
<212> TYPE: PRT
<213> ORGANISM: Artificial Sequence
<220> FEATURE:
<223> OTHER INFORMATION: B2 - VL

<400> SEQUENCE: 84

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asp Asp
            20                  25                  30

Val Thr Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60
```

```
Ser Gly Ser Gly Thr Asp Phe Thr Phe Thr Ile Ser Ser Val Gln Pro
65                  70                  75                  80

Glu Asp Ile Ala Thr Tyr Tyr Cys Gln Gln Asp Tyr Ser Ser Pro Trp
                85                  90                  95

Thr Phe Gly Gly Gly Thr Lys Leu Glu Ile Lys
            100                 105


<210> SEQ ID NO 85
<211> LENGTH: 117
<212> TYPE: PRT
<213> ORGANISM: Artificial Sequence
<220> FEATURE:
<223> OTHER INFORMATION: C1 - VH

<400> SEQUENCE: 85

Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Phe Ser Asp Thr Thr Tyr Ser Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser
        115


<210> SEQ ID NO 86
<211> LENGTH: 107
<212> TYPE: PRT
<213> ORGANISM: Artificial Sequence
<220> FEATURE:
<223> OTHER INFORMATION: C1 - VL

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys
            100                 105


<210> SEQ ID NO 87
<211> LENGTH: 117
<212> TYPE: PRT
<213> ORGANISM: Artificial Sequence
```

```
<220> FEATURE:
<223> OTHER INFORMATION: C2 - VH

<400> SEQUENCE: 87

Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Leu Ser Asp Thr Thr Tyr Ser Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser
        115


<210> SEQ ID NO 88
<211> LENGTH: 107
<212> TYPE: PRT
<213> ORGANISM: Artificial Sequence
<220> FEATURE:
<223> OTHER INFORMATION: C2 - VL

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys
            100                 105


<210> SEQ ID NO 89
<211> LENGTH: 117
<212> TYPE: PRT
<213> ORGANISM: Artificial Sequence
<220> FEATURE:
<223> OTHER INFORMATION: C3 - VH

<400> SEQUENCE: 89

Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45
```

```
Gly Ala Ile Tyr Pro Gly Leu Ser Asp Thr Thr Tyr Ser Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser
        115
```

<210> SEQ ID NO 90
<211> LENGTH: 107
<212> TYPE: PRT
<213> ORGANISM: Artificial Sequence
<220> FEATURE:
<223> OTHER INFORMATION: C3 - VL

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys
            100                 105
```

<210> SEQ ID NO 91
<211> LENGTH: 117
<212> TYPE: PRT
<213> ORGANISM: Artificial Sequence
<220> FEATURE:
<223> OTHER INFORMATION: C4 - VH

<400> SEQUENCE: 91

```
Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Leu Ser Asp Thr Thr Tyr Asn Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser
        115
```

<210> SEQ ID NO 92
<211> LENGTH: 107
<212> TYPE: PRT
<213> ORGANISM: Artificial Sequence
<220> FEATURE:
<223> OTHER INFORMATION: C4 - VL

<400> SEQUENCE: 92

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys
            100                 105
```

<210> SEQ ID NO 93
<211> LENGTH: 117
<212> TYPE: PRT
<213> ORGANISM: Artificial Sequence
<220> FEATURE:
<223> OTHER INFORMATION: C5 - VH

<400> SEQUENCE: 93

```
Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Asn Ser Asp Thr Thr Tyr Asn Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser
        115
```

<210> SEQ ID NO 94
<211> LENGTH: 107
<212> TYPE: PRT
<213> ORGANISM: Artificial Sequence
<220> FEATURE:
<223> OTHER INFORMATION: C5 - VL

<400> SEQUENCE: 94

```
Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys
            100                 105


<210> SEQ ID NO 95
<211> LENGTH: 117
<212> TYPE: PRT
<213> ORGANISM: Artificial Sequence
<220> FEATURE:
<223> OTHER INFORMATION: C6 - VH

<400> SEQUENCE: 95

Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Asn Ser Asp Thr Thr Tyr Asn Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser
        115


<210> SEQ ID NO 96
<211> LENGTH: 107
<212> TYPE: PRT
<213> ORGANISM: Artificial Sequence
<220> FEATURE:
<223> OTHER INFORMATION: C6 - VL

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95
```

```
Thr Phe Gly Gln Gly Thr Lys Leu Glu Ile Lys
            100                 105


<210> SEQ ID NO 97
<211> LENGTH: 451
<212> TYPE: PRT
<213> ORGANISM: Artificial Sequence
<220> FEATURE:
<223> OTHER INFORMATION: A1 - HC

<400> SEQUENCE: 97

Asp Val Lys Leu Val Glu Ser Gly Gly Gly Leu Val Lys Leu Gly Gly
1               5                   10                  15

Ser Leu Lys Leu Ser Cys Val Ala Ser Gly Phe Thr Phe Ser His Tyr
            20                  25                  30

Tyr Met Ser Trp Ile Arg Gln Thr Pro Glu Lys Arg Leu Glu Trp Val
        35                  40                  45

Ala Thr Ile Asn Gly Gly Gly Gly Asn Thr Tyr Tyr Pro Asp Ser Val
    50                  55                  60

Lys Asp Arg Phe Thr Ile Ser Arg Asp Asn Ala Lys Asn Thr Leu Tyr
65                  70                  75                  80

Leu Gln Met Ser Ser Leu Asn Ser Glu Asp Thr Ala Val Tyr Tyr Cys
                85                  90                  95

Ala Arg Gly Gly Pro Tyr Ser Asn Tyr Val Trp Phe Ala Tyr Trp Gly
            100                 105                 110

Gln Gly Thr Leu Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 98
<211> LENGTH: 218
<212> TYPE: PRT
<213> ORGANISM: Artificial Sequence
<220> FEATURE:
<223> OTHER INFORMATION: A1 - LC

<400> SEQUENCE: 98

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Thr Thr Ser
            20                  25                  30

Ser Tyr Thr Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Ile Tyr Tyr Cys Gln His Ser Trp
                85                  90                  95

Glu Asn Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 99
<211> LENGTH: 448
<212> TYPE: PRT
<213> ORGANISM: Artificial Sequence
```

<220> FEATURE:
<223> OTHER INFORMATION: A2 - HC

<400> SEQUENCE: 99

Gln Gly Gln Met Gln Gln Ser Gly Ala Glu Leu Val Lys Pro Gly Thr
1 5 10 15

Ser Val Lys Leu Ser Cys Lys Thr Ser Gly Phe Thr Phe Ser Ser Ser
20 25 30

Tyr Ile Ser Trp Leu Lys Gln Arg Pro Arg Gln Ser Leu Glu Trp Ile
35 40 45

Ala Trp Ile Tyr Ala Gly Thr Gly Asn Thr Asn Tyr Asn Gln Lys Phe
50 55 60

Thr Asp Lys Ala Gln Val Thr Val Asp Thr Ser Ser Ser Thr Ala Tyr
65 70 75 80

Met Gln Leu Ser Ser Leu Thr Ser Glu Asp Ser Ala Ile Tyr Tyr Cys
85 90 95

Ala Arg His Val Asn Trp Asp Tyr Phe Asp Tyr Trp Gly Gln Gly Thr
100 105 110

Thr Leu Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 100
<211> LENGTH: 214
<212> TYPE: PRT
<213> ORGANISM: Artificial Sequence
<220> FEATURE:
<223> OTHER INFORMATION: A2 - LC

<400> SEQUENCE: 100

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Val Trp Tyr Gln Gln Lys Pro Gly Gln Ser Pro Lys Leu Leu Ile
        35                  40                  45

Tyr Trp Ala Ser Ser Arg His Thr Gly Val Pro Asp Arg Phe Thr Gly
    50                  55                  60

Ser Gly Ser Gly Thr Asp Phe Thr Leu Thr Leu Thr Asn Val Gln Ser
65                  70                  75                  80

Glu Asp Leu Ala Asp Tyr Phe Cys Gln Gln Tyr Arg Ser Tyr Pro Trp
                85                  90                  95

Thr Phe Gly Gly Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 101
<211> LENGTH: 447
<212> TYPE: PRT
<213> ORGANISM: Artificial Sequence
<220> FEATURE:
<223> OTHER INFORMATION: A3 - HC

<400> SEQUENCE: 101

Glu Val Gln Leu Gln Gln Ser Gly Thr Val Leu Ala Arg Pro Gly Asp
1               5                   10                  15

Ser Val Lys Met Ser Cys Lys Thr Ser Gly Tyr Thr Phe Thr Thr Tyr
            20                  25                  30

Trp Met His Trp Val Lys Gln Arg Pro Gly Gln Gly Leu Glu Trp Ile
```

```
        35                  40                  45

Gly Ala Ile Tyr Pro Gly Asn Ser Asp Thr Thr Tyr Asn Gln Lys Phe
    50                  55                  60

Lys Gly Lys Ala Lys Leu Thr Ala Val Thr Ser Ala Ser Thr Ala Tyr
65                  70                  75                  80

Met Lys Leu Ser Ser Leu Thr Asn Glu Asp Ser Ala Val Tyr Tyr Cys
                85                  90                  95

Thr Arg Leu Leu Asp Tyr Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 102

<211> LENGTH: 214
<212> TYPE: PRT
<213> ORGANISM: Artificial Sequence
<220> FEATURE:
<223> OTHER INFORMATION: A3 - LC

<400> SEQUENCE: 102

```
Glu Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp His Gln Gln Lys Pro Asp Gly Thr Val Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 103
<211> LENGTH: 450
<212> TYPE: PRT
<213> ORGANISM: Artificial Sequence
<220> FEATURE:
<223> OTHER INFORMATION: A4 - HC

<400> SEQUENCE: 103

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Leu Thr Phe Ser Ser Tyr
            20                  25                  30

Val Met Ser Trp Val Arg Gln Thr Pro Ala Lys Arg Leu Glu Trp Val
        35                  40                  45

Ala Thr Ile Ser Ser Gly Gly Val Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Met Ser Glu Asp Thr Ala Met Tyr Tyr Cys
                85                  90                  95

Ala Arg Arg Glu Thr Ala Arg Ala Thr Gly Phe Ala Tyr Trp Gly Gln
```

```
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 104
<211> LENGTH: 214
<212> TYPE: PRT
<213> ORGANISM: Artificial Sequence
<220> FEATURE:
<223> OTHER INFORMATION: A4 - LC

<400> SEQUENCE: 104

Ser Ile Val Met Thr Gln Thr Pro Lys Phe Leu Leu Val Ser Ala Gly
```

```
1               5                   10                  15

Asp Arg Val Thr Ile Thr Cys Lys Ala Ser Gln Ser Val Ser Asn Asp
            20                  25                  30

Val Thr Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Asn Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 105
<211> LENGTH: 450
<212> TYPE: PRT
<213> ORGANISM: Artificial Sequence
<220> FEATURE:
<223> OTHER INFORMATION: B1 - HC

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Val Met Ser Trp Val Arg Gln Ala Pro Gly Lys Gly Leu Glu Trp Val
        35                  40                  45

Ser Thr Ile Ser Ser Gly Gly Val Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Glu Thr Ala Arg Ala Thr Gly Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 106
<211> LENGTH: 214
<212> TYPE: PRT
<213> ORGANISM: Artificial Sequence
<220> FEATURE:
<223> OTHER INFORMATION: B1 - LC

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Thr Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
```

```
    50                  55                  60

Ser Gly Ser Gly Thr Asp Phe Thr Phe Thr Ile Ser Ser Val Gln Pro
65                  70                  75                  80

Glu Asp Ile Ala Thr Tyr Tyr Cys Gln Gln Asp Tyr Ser Ser Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 107
<211> LENGTH: 450
<212> TYPE: PRT
<213> ORGANISM: Artificial Sequence
<220> FEATURE:
<223> OTHER INFORMATION: B2 - HC

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Val Met Ser Trp Val Arg Gln Ala Pro Gly Lys Gly Leu Glu Trp Val
        35                  40                  45

Ser Thr Ile Ser Ser Gly Gly Val Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Glu Thr Ala Arg Ala Thr Gly Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 108
<211> LENGTH: 214
<212> TYPE: PRT
<213> ORGANISM: Artificial Sequence
<220> FEATURE:
<223> OTHER INFORMATION: B2 - LC

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asp Asp
            20                  25                  30

Val Thr Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Val Gln Pro
65                  70                  75                  80

Glu Asp Ile Ala Thr Tyr Tyr Cys Gln Gln Asp Tyr Ser Ser Pro Trp
                85                  90                  95

Thr Phe Gly Gly Gly Thr Lys Leu Glu Ile Lys Arg Thr Val Ala Ala
```

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 109
<211> LENGTH: 446
<212> TYPE: PRT
<213> ORGANISM: Artificial Sequence
<220> FEATURE:
<223> OTHER INFORMATION: C1 - HC

<400> SEQUENCE: 109

Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Phe Ser Asp Thr Thr Tyr Ser Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
```

```
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 110
<211> LENGTH: 214
<212> TYPE: PRT
<213> ORGANISM: Artificial Sequence
<220> FEATURE:
<223> OTHER INFORMATION: C1 - LC

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 111
<211> LENGTH: 446
<212> TYPE: PRT
<213> ORGANISM: Artificial Sequence
<220> FEATURE:
<223> OTHER INFORMATION: C2 - HC

<400> SEQUENCE: 111

Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Leu Ser Asp Thr Thr Tyr Ser Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
```

```
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 112
<211> LENGTH: 214
<212> TYPE: PRT
<213> ORGANISM: Artificial Sequence
<220> FEATURE:
<223> OTHER INFORMATION: C2 - LC

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 113
<211> LENGTH: 446
<212> TYPE: PRT
<213> ORGANISM: Artificial Sequence
<220> FEATURE:
<223> OTHER INFORMATION: C3 - HC

<400> SEQUENCE: 113

Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Leu Ser Asp Thr Thr Tyr Ser Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
```

```
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 114
<211> LENGTH: 214
<212> TYPE: PRT
<213> ORGANISM: Artificial Sequence
<220> FEATURE:
<223> OTHER INFORMATION: C3 - LC

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 115
<211> LENGTH: 446
<212> TYPE: PRT
<213> ORGANISM: Artificial Sequence
<220> FEATURE:
<223> OTHER INFORMATION: C4 - HC

<400> SEQUENCE: 115

Gln Val Gln Leu Val Gln Ser Gly Ala Glu Val Lys Lys Pro Gly Asp
1               5                   10                  15
```

```
Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Leu Ser Asp Thr Thr Tyr Asn Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
```

```
        435                 440                 445


<210> SEQ ID NO 116
<211> LENGTH: 214
<212> TYPE: PRT
<213> ORGANISM: Artificial Sequence
<220> FEATURE:
<223> OTHER INFORMATION: C4 - LC

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 117
<211> LENGTH: 446
<212> TYPE: PRT
<213> ORGANISM: Artificial Sequence
<220> FEATURE:
<223> OTHER INFORMATION: C5 - HC

<400> SEQUENCE: 117

Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Asn Ser Asp Thr Thr Tyr Asn Gln Lys Phe
    50                  55                  60

Lys Gly Lys Val Thr Met Thr Arg Asp Thr Ser Thr Ser Thr Val Tyr
65                  70                  75                  80
```

```
Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
                100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 118
<211> LENGTH: 214
<212> TYPE: PRT
<213> ORGANISM: Artificial Sequence
<220> FEATURE:
<223> OTHER INFORMATION: C5 - LC

<400> SEQUENCE: 118

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Thr Tyr Phe Cys Gln Gln Gly Glu Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 119
<211> LENGTH: 446
<212> TYPE: PRT
<213> ORGANISM: Artificial Sequence
<220> FEATURE:
<223> OTHER INFORMATION: C6 - HC

<400> SEQUENCE: 119

Gln Val Gln Leu Val Gln Ser Gly Ala Glu Val Lys Lys Pro Gly Asp
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Ala Ile Tyr Pro Gly Asn Ser Asp Thr Thr Tyr Asn Gln Lys Phe
    50                  55                  60

Lys Gly Lys Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg Leu Leu Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 120
<211> LENGTH: 214
<212> TYPE: PRT
<213> ORGANISM: Artificial Sequence
<220> FEATURE:
<223> OTHER INFORMATION: C6 - LC

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp His Gln Gln Lys Pro Gly Lys Ala Pro Lys Leu Leu Ile
        35                  40                  45

Trp Tyr Thr Ser Arg Leu His Ser Gly Val Pro Ser Arg Phe Ser Gly
    50                  55                  60
```

```
Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 121
<211> LENGTH: 446
<212> TYPE: PRT
<213> ORGANISM: Artificial Sequence
<220> FEATURE:
<223> OTHER INFORMATION: PD1-1 - HC

<400> SEQUENCE: 121

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205
```

```
Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 122
<211> LENGTH: 218
<212> TYPE: PRT
<213> ORGANISM: Artificial Sequence
<220> FEATURE:
<223> OTHER INFORMATION: PD1-1 - LC

<400> SEQUENCE: 122

```
Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 123
<211> LENGTH: 446
<212> TYPE: PRT
<213> ORGANISM: Artificial Sequence
<220> FEATURE:
<223> OTHER INFORMATION: PD1-2 - HC

<400> SEQUENCE: 123

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Pro Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

```
Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 124
<211> LENGTH: 218
<212> TYPE: PRT
<213> ORGANISM: Artificial Sequence
<220> FEATURE:
<223> OTHER INFORMATION: PD1-2 - LC

<400> SEQUENCE: 124

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

```
His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 125
<211> LENGTH: 446
<212> TYPE: PRT
<213> ORGANISM: Artificial Sequence
<220> FEATURE:
<223> OTHER INFORMATION: PD1-3 - HC

<400> SEQUENCE: 125

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 126
<211> LENGTH: 218
<212> TYPE: PRT
<213> ORGANISM: Artificial Sequence
<220> FEATURE:
<223> OTHER INFORMATION: PD1-3 - LC

<400> SEQUENCE: 126

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 127
<211> LENGTH: 446
<212> TYPE: PRT
<213> ORGANISM: Artificial Sequence
<220> FEATURE:
```

<223> OTHER INFORMATION: PD1-4 - HC

<400> SEQUENCE: 127

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 128
<211> LENGTH: 218
<212> TYPE: PRT
<213> ORGANISM: Artificial Sequence
<220> FEATURE:
<223> OTHER INFORMATION: PD1-4 - LC

<400> SEQUENCE: 128

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 129
<211> LENGTH: 446
<212> TYPE: PRT
<213> ORGANISM: Artificial Sequence
<220> FEATURE:
<223> OTHER INFORMATION: PD1-5 - HC

<400> SEQUENCE: 129

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45
```

```
Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 130
<211> LENGTH: 218

<212> TYPE: PRT
<213> ORGANISM: Artificial Sequence
<220> FEATURE:
<223> OTHER INFORMATION: PD1-5 - LC

<400> SEQUENCE: 130

```
Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 131
<211> LENGTH: 785
<212> TYPE: PRT
<213> ORGANISM: Artificial Sequence
<220> FEATURE:
<223> OTHER INFORMATION: mature murine CD73-HuFc-His6

<400> SEQUENCE: 131

```
Trp Glu Leu Thr Ile Leu His Thr Asn Asp Val His Ser Arg Leu Glu
1               5                   10                  15

Gln Thr Ser Asp Asp Ser Thr Lys Cys Leu Asn Ala Ser Leu Cys Val
            20                  25                  30

Gly Gly Val Ala Arg Leu Phe Thr Lys Val Gln Gln Ile Arg Lys Glu
        35                  40                  45

Glu Pro Asn Val Leu Phe Leu Asp Ala Gly Asp Gln Tyr Gln Gly Thr
    50                  55                  60

Ile Trp Phe Thr Val Tyr Lys Gly Leu Glu Val Ala His Phe Met Asn
65                  70                  75                  80

Ile Leu Gly Tyr Asp Ala Met Ala Leu Gly Asn His Glu Phe Asp Asn
                85                  90                  95

Gly Val Glu Gly Leu Ile Asp Pro Leu Leu Arg Asn Val Lys Phe Pro
            100                 105                 110
```

```
Ile Leu Ser Ala Asn Ile Lys Ala Arg Gly Pro Leu Ala His Gln Ile
        115                 120                 125

Ser Gly Leu Phe Leu Pro Ser Lys Val Leu Ser Val Gly Gly Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Ser Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Ile Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ala Asp Asp Gly Arg Gln Val Pro Val Val Gln Ala Tyr Ala
                245                 250                 255

Phe Gly Lys Tyr Leu Gly Tyr Leu Lys Val Glu Phe Asp Asp Lys Gly
            260                 265                 270

Asn Val Ile Thr Ser Tyr Gly Asn Pro Ile Leu Leu Asn Ser Ser Ile
        275                 280                 285

Pro Glu Asp Ala Thr Ile Lys Ala Asp Ile Asn Gln Trp Arg Ile Lys
    290                 295                 300

Leu Asp Asn Tyr Ser Thr Gln Glu Leu Gly Arg Thr Ile Val Tyr Leu
305                 310                 315                 320

Asp Gly Ser Thr Gln Thr Cys Arg Phe Arg Glu Cys Asn Met Gly Asn
                325                 330                 335

Leu Ile Cys Asp Ala Met Ile Asn Asn Asn Leu Arg His Pro Asp Glu
            340                 345                 350

Met Phe Trp Asn His Val Ser Met Cys Ile Val Asn Gly Gly Gly Ile
        355                 360                 365

Arg Ser Pro Ile Asp Glu Lys Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Ile Asn Arg Lys Pro Trp Asn Arg Val Val Gln Leu Glu Val
        435                 440                 445

Leu Cys Thr Lys Cys Arg Val Pro Ile Tyr Glu Pro Leu Glu Met Asp
    450                 455                 460

Lys Val Tyr Lys Val Thr Leu Pro Ser Tyr Leu Ala Asn Gly Gly Asp
465                 470                 475                 480

Gly Phe Gln Met Ile Lys Asp Glu Leu Leu Lys His Asp Ser Gly Asp
                485                 490                 495

Gln Asp Ile Ser Val Val Ser Glu Tyr Ile Ser Lys Met Lys Val Val
            500                 505                 510

Tyr Pro Ala Val Glu Gly Arg Ile Lys Phe Ser Gly Gly Ser Gly Gly
        515                 520                 525
```

-continued

```
Ser Gly Gly Ser Gly Gly Ser Gly Gly Ser Gly Gly Ser Gly Gly Glu
    530                 535                 540

Pro Lys Ser Cys Asp Lys Thr His Thr Cys Pro Pro Cys Pro Ala Pro
545                 550                 555                 560

Glu Leu Leu Gly Gly Pro Ser Val Phe Leu Phe Pro Pro Lys Pro Lys
                565                 570                 575

Asp Thr Leu Met Ile Ser Arg Thr Pro Glu Val Thr Cys Val Val Val
            580                 585                 590

Asp Val Ser His Glu Asp Pro Glu Val Lys Phe Asn Trp Tyr Val Asp
        595                 600                 605

Gly Val Glu Val His Asn Ala Lys Thr Lys Pro Arg Glu Glu Gln Tyr
    610                 615                 620

Asn Ser Thr Tyr Arg Val Val Ser Val Leu Thr Val Leu His Gln Asp
625                 630                 635                 640

Trp Leu Asn Gly Lys Glu Tyr Lys Cys Lys Val Ser Asn Lys Ala Leu
                645                 650                 655

Pro Ala Pro Ile Glu Lys Thr Ile Ser Lys Ala Lys Gly Gln Pro Arg
            660                 665                 670

Glu Pro Gln Val Tyr Thr Leu Pro Pro Ser Arg Asp Glu Leu Thr Lys
        675                 680                 685

Asn Gln Val Ser Leu Thr Cys Leu Val Lys Gly Phe Tyr Pro Ser Asp
    690                 695                 700

Ile Ala Val Glu Trp Glu Ser Asn Gly Gln Pro Glu Asn Asn Tyr Lys
705                 710                 715                 720

Thr Thr Pro Pro Val Leu Asp Ser Asp Gly Ser Phe Phe Leu Tyr Ser
                725                 730                 735

Lys Leu Thr Val Asp Lys Ser Arg Trp Gln Gln Gly Asn Val Phe Ser
            740                 745                 750

Cys Ser Val Met His Glu Ala Leu His Asn His Tyr Thr Gln Lys Ser
        755                 760                 765

Leu Ser Leu Ser Pro Gly Lys Ala Gly Ser Ala His His His His His
    770                 775                 780

His
785
```

ANTAGONIZING CD73 ANTIBODY

SEQUENCE LISTING

The instant application contains a Sequence Listing which has been submitted electronically in ASCII format and is hereby incorporated by reference in its entirety. Said ASCII copy, created on, May 10, 2019 is named 12-0426-US-1sequencelisting.txt and is 139 bytes in size.

FIELD OF THE INVENTION

The present invention relates to novel CD73 binding polypeptides. The invention also relates to nucleic acids encoding such polypeptides; to methods for preparing such polypeptides; to host cells expressing or capable of expressing such polypeptides; to compositions comprising such polypeptides; and to uses of such polypeptides or such compositions, in particular for therapeutic purposes in the field of cancer diseases.

BACKGROUND OF THE INVENTION

Cancer is a disease characterized by abnormal cell growth with the potential to spread throughout the body. In the developed world it is the second most common cause of death. The most common types of cancer in males are lung cancer, prostate cancer, colorectal cancer, and stomach cancer, and in females, the most common types are breast cancer, colorectal cancer, lung cancer, and cervical cancer. While the chances of survival depend mainly on the type of cancer and the stage at identification, for lung cancer the overall 10 year survival rate is around 5%.

In the past the most frequent means of treating cancers were through surgery, radiation treatment, or the use of chemotherapeutic drugs. However, in recent years, cancer immunotherapy has shown to offer much promise as a treatment modality for oncology.

Cancer immunotherapy is a branch of oncology in which the immune system is activated to attack the cancer, which is in stark contrast to existing common methods of treatment in which the tumor is directly excised or treated. This therapeutic concept is based on the identification of a number of proteins on the surface of T-cells which act to inhibit the immune function of these cells. Immunotherapies either block such inhibitory molecules to increase the activity of the immune system or stimulate pathways involved in the activation of immune effector cells. Listed among these proteins are CD73 and PD-1.

Cluster of Differentiation 73 (CD73), also known as ecto-5'-nucleotidase (ecto-5'NT, EC 3.1.3.5), is a glycosylphosphatidylinositol (GPI)-linked cell surface enzyme found in most tissues, but particularly expressed in endothelial cells and subsets of hematopoietic cells (Resta et al., Immunol Rev 1998; 161:95-109 and Colgan et al., Purinergic Signal 2006; 2:351-60).

CD73 is a cell surface enzyme expressed on cancer cells, stromal cells and tumor-residing immune cells that converts AMP to adenosine and inorganic phosphate. Adenosine is immunosuppressive and has the capacity to influence the function of several immune cell types. Adenosine has an activatory effect on immunosuppressive cells such as regulatory T cells, MDSCs and M2 macrophages and an inhibitory effect on effector cells such as dendritic cells, effector T cells and NK cells. A neutralizing CD73 antibody may inhibit the function of CD73 by blocking the enzymatic activity and/or by reducing CD73 cell surface levels. This will lead to a reduction in immunosuppressive adenosine and thus to an increase in T cell activities.

Dual blockade of CD73 and immune checkpoints—including PD1 and potentially others—may further restore T cell functionality, resulting in improved objective responses and prolongation of overall survival in cancer patients compared to PD1 monotherapy.

CD73 has been reported to be expressed on many different cancers, including colon, lung, pancreas, ovary, bladder, leukemia, glioma, glioblastoma, melanoma, thyroid, esophageal, prostate and breast cancers (Jin et al., Cancer Res 2010; 70:2245-55 and Stagg et al., PNAS 2010; 107: 1547-52). Moreover, CD73 expression in cancer has been correlated to shorter overall survival in a number of tumor indications, amongst others gastrointestinal, breast and NSCLC tumors (Wang et al., Prognostic value of CD73-adenosinergic pathway in solid tumor: A meta-analysis and systematic review, Oncotarget 2017; Inoue et al., Prognostic impact of CD73 and A2A adenosine receptor expression in non-small-cell lung cancer, Oncotarget 2017). CD73 activity has also been proposed as a prognostic marker in papillary thyroid carcinomas. By generating immunosuppressive adenosine, CD73 has widespread functions on immune cells and creates an immunosuppressive microenvironment within the tumor. Adenosine potently suppresses T cell responses such as proliferation, cytotoxicity and cytokine production. In addition, adenosine alters the differentiation of dendritic cells, thus impairing T cell responses. Adenosine also acts upon NK cells, resulting in an inhibition of their cytotoxic function. Further, adenosine has a stimulatory role on immunosuppressive cell types. Adenosine leads to the expansion of immunosuppressive MDSCs and the differentiation of macrophages into the suppressive M2 phenotype. (Antonioli et al., Immunity, inflammation and cancer: a leading role for adenosine. Nature Reviews Cancer 2013; Beavis et al., CD73: A potent suppressor of antitumor immune responses, Trends in Immunology, 2012). In addition to its effects on immune cells, CD73 might have roles in the regulation of cell-cell and cell-matrix interactions as well as of angiogenesis. Adenosine can also act directly on cancer cells and regulate cell growth as well as apoptosis and is implicated in drug resistance (Hunsucker et al., Pharmacol Ther 2005; 1:1-30). Thus CD73 can regulate cancer progression both directly and indirectly, which highlights its potential as a novel therapeutic target. Allard et al have reported that targeting CD73 enhances the antitumour activity of anti-PD-1 and anti-CTLA-4 mAbs (Clin Cancer Res 2013; 19:5626).

Other agents that target the same pathways include A2AR antagonists. However, due to adenosine receptor redundancy, it may be expected that the A2AR antagonists may not fully prevent adenosine-mediated activities relative to a CD73 inhibitor.

The non-hydrolyzable ADP-analog adenosine 5'-(alpha, beta-methylene) diphosphate (APCP) is an inhibitor of the CD73 enzymatic activity and is commercially available. AB421 is a small molecule CD73 inhibitor developed by Arcus Biosciences.

WO 2016/075099 discloses anti-CD73 binding molecules, e.g., antibodies and antigen binding fragments thereof, including the MED19447 antibody. MED19447 reduces CD73 function by inhibiting the enzymatic activity of CD73 to hydrolyze adenosine monophosphate (AMP) and by inducing internalization of CD73. WO 2016/081748 discloses antibodies inhibiting enzymatic activity of human CD73, and antibodies internalizing CD73 into cells, including the BMS 986179 antibody.

It is an object of the invention to provide improved pharmacologically active agents that can be used in the treatment of several cancer diseases.

In particular, it is an object of the invention to provide such pharmacologically active agents, compositions and/or methods of treatment that provide certain advantages compared to the agents, compositions and/or methods currently used and/or known in the art. These advantages include in vivo efficacy, improved therapeutic and pharmacological properties, less side effects, and other advantageous properties such as improved ease of preparation or reduced costs of goods, especially as compared to candidate drugs already known in the art.

BRIEF SUMMARY OF THE INVENTION

According to a first aspect there are provided anti-CD73 antibody molecules. As described further herein, the anti-CD73 antibody molecules of the present invention have surprising and advantageous properties over other anti-CD73 antibodies. For example, they show improved capacity to revert AMP-mediated T cell suppression (e.g. as demonstrated by higher T cell proliferation levels and stronger induction of IFNγ secretion). IFNγ is known to be a crucial factor for the anti-tumor response mediated by T cells (Tannenbaum, C., and Hamilton, T. Immune-inflammatory mechanisms in IFNγ-mediated anti-tumor activity, Seminars in Cancer Biology, 2000). Further, the anti-CD73 antibodies described herein show improved inhibition of CD73 compared to prior art anti-CD73 antibodies. The antibodies of the present invention inhibit cell-bound CD73 as well as non-cell-bound CD73 equally well. The anti-CD73 antibodies of the invention show improved inhibition of adenosine generation compared to reference anti-CD73 antibodies. Furthermore, they have high affinity to human CD73.

Nucleic acid molecules encoding the anti-CD73 antibody molecules, expression vectors, host cells and methods of making the anti-CD73 antibody molecules of the invention are also provided. Pharmaceutical compositions comprising the anti-CD73 antibody molecules of the invention are also provided. The anti-CD73 antibody molecules disclosed herein can be used to treat cancerous disorders, including solid and soft-tissue tumors.

More specifically, an anti-CD73 antibody molecule of the invention comprises:

(a) heavy chain CDRs comprising the amino acid sequence of SEQ ID NO:25 (hcCDR1), SEQ ID NO:26 (hcCDR2) and SEQ ID NO:27 (hcCDR3) and light chain CDRs comprising the amino acid sequence of SEQ ID NO:28 (lcCDR1), SEQ ID NO:29 (lcCDR2) and SEQ ID NO:30 (lcCDR3); or, (b) heavy chain CDRs comprising the amino acid sequence of SEQ ID NO:31 (hcCDR1), SEQ ID NO:32 (hcCDR2) and SEQ ID NO:33 (hcCDR3) and light chain CDRs comprising the amino acid sequence of SEQ ID NO:34 (lcCDR1), SEQ ID NO:35 (lcCDR2) and SEQ ID NO:36 (lcCDR3); or, (c) heavy chain CDRs comprising the amino acid sequence of SEQ ID NO:37 (hcCDR1), SEQ ID NO:38 (hcCDR2) and SEQ ID NO:39 (hcCDR3) and light chain CDRs comprising the amino acid sequence of SEQ ID NO:40 (lcCDR1), SEQ ID NO:41 (lcCDR2) and SEQ ID NO:42 (lcCDR3); or (d) heavy chain CDRs comprising the amino acid sequence of SEQ ID NO:43 (hcCDR1), SEQ ID NO:44 (hcCDR2) and SEQ ID NO:45 (hcCDR3) and light chain CDRs comprising the amino acid sequence of SEQ ID NO:46 (lcCDR1), SEQ ID NO:47 (lcCDR2) and SEQ ID NO:48 (lcCDR3); or (e) heavy chain CDRs comprising the amino acid sequence of SEQ ID NO:49 (hcCDR1), SEQ ID NO:50 (hcCDR2) and SEQ ID NO:51 (hcCDR3) and light chain CDRs comprising the amino acid sequence of SEQ ID NO:52 (lcCDR1), SEQ ID NO:53 (lcCDR2) and SEQ ID NO:54 (lcCDR3); or (f) heavy chain CDRs comprising the amino acid sequence of SEQ ID NO:55 (hcCDR1), SEQ ID NO:56 (hcCDR2) and SEQ ID NO:57 (hcCDR3) and light chain CDRs comprising the amino acid sequence of SEQ ID NO:58 (lcCDR1), SEQ ID NO:59 (lcCDR2) and SEQ ID NO:60 (lcCDR3); or (g) heavy chain CDRs comprising the amino acid sequence of SEQ ID NO:61 (hcCDR1), SEQ ID NO:62 (hcCDR2) and SEQ ID NO:63 (hcCDR3) and light chain CDRs comprising the amino acid sequence of SEQ ID NO:64 (lcCDR1), SEQ ID NO:65 (lcCDR2) and SEQ ID NO:66 (lcCDR3); or (h) heavy chain CDRs comprising the amino acid sequence of SEQ ID NO:67 (hcCDR1), SEQ ID NO:68 (hcCDR2) and SEQ ID NO:69 (hcCDR3) and light chain CDRs comprising the amino acid sequence of SEQ ID NO:70 (lcCDR1), SEQ ID NO:71 (lcCDR2) and SEQ ID NO:72 (lcCDR3).

According to a further aspect of the invention, there is also provided methods for the treatment of cancers. In one embodiment, anti-CD73 antibody molecules of the invention may be used in combination with a second therapeutic agent, such as a PD-1 antagonist. In some embodiments said second therapeutic agent, such as a PD-1 antagonist, is to be administered simultaneously, concurrently, sequentially, successively, alternatively or separately, with the anti-CD73 antibody molecules. In some embodiments the PD-1 antagonist is an anti-PD-1 antibody or an anti-PDL-1 antibody. In some embodiments the PD-1 antagonist is an anti-PD-1 antibody selected from the group consisting of PDR-001, pembrolizumab, nivolumab and pidilizumab. In some embodiments the PD-1 antagonist is an anti-PDL-1 antibody selected from the group consisting of atezolizumab, avelumab and durvalumab. In some embodiments the PD-1 antagonist is an anti-PD-1 antibody selected from the group consisting of PD1-1, PD1-2, PD1-3, PD1-4 and PD1-5. Further embodiments of these aspects of the invention include where said uses of the antibody molecules of the invention can be combined with a third therapeutic agent.

Further aspects, embodiments, uses and methods involving the antibody molecules of the invention will become clear from the following detailed description of the invention and from the appended claims.

The invention provides for novel antibody molecules that allow a more efficient treatment of several cancer types, including lung cancer (e.g. non-small cell lung cancer, NSCLC), various gastrointestinal cancers (e.g. colon carcinoma, gastric cancer, hepatocellular carcinoma) and kidney cancer, (e.g. renal cell cancer such as clear cell carcinoma).

Figure 1:
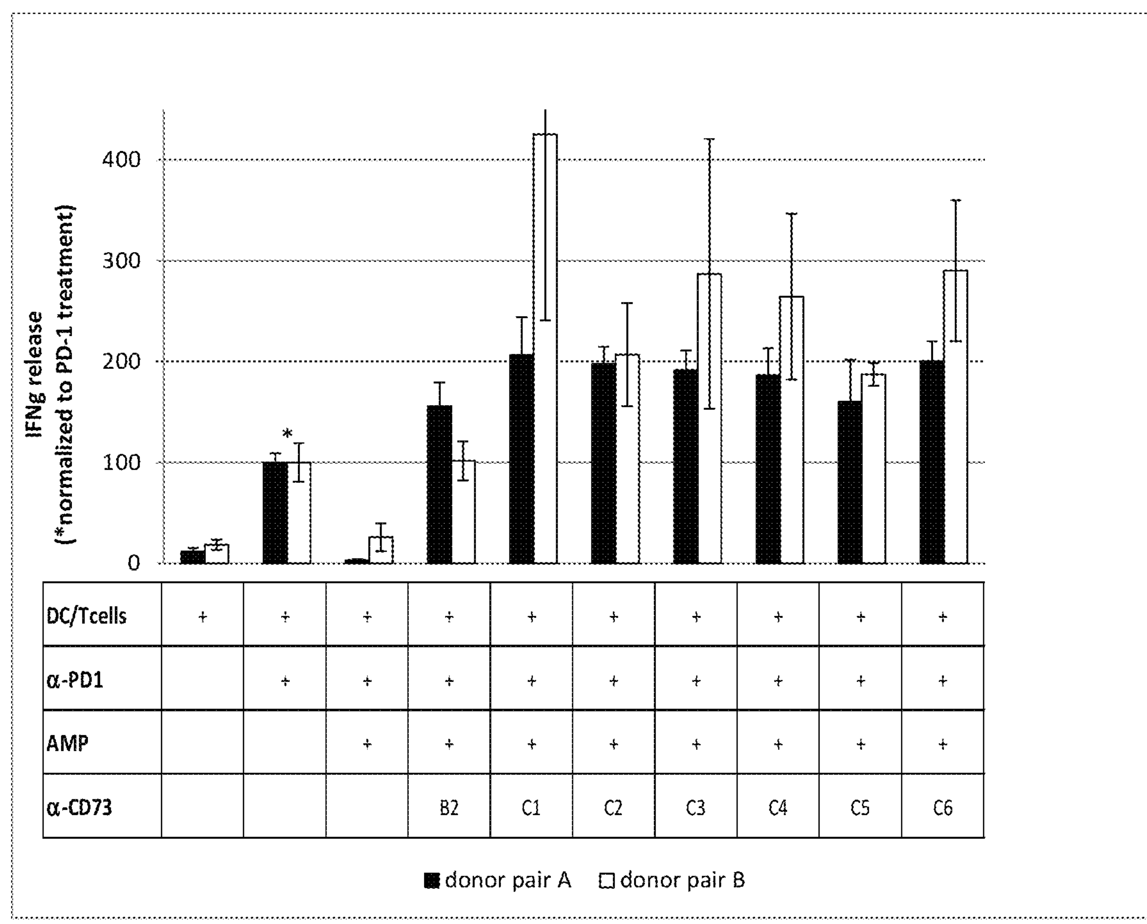
FIG. 1: Dendritic cell/T cell co-culture. The data (as further described in Example 7) illustrate that AMP inhibits the anti-PD1 response in a dendritic/T cell co-culture assay, and anti-CD73 antibody treatment leads to reversal of this AMP-mediated inhibition.

Stimulated primary human T cells were treated with a range of αCD73 antibody concentrations followed by addition of AMP. Induction of proliferation and release of IFNγ was measured. The assay was done as outlined in Example 6.

DETAILED DESCRIPTION OF THE INVENTION

Definitions

The above and other aspects and embodiments of the invention will become clear from the further description herein.

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" ($2^{nd}$ Ed.), Gower Medical Publishing, London, New York (1989), as well as to the general background art cited herein. Furthermore, unless indicated otherwise, all methods, steps, techniques and manipulations that are not specifically described in detail can be performed and have been performed in a manner known per se, as will be clear to the skilled person.

Reference is for example again made to the standard handbooks, to the general background art referred to above and to the further references cited therein.

As used herein, the articles "a" and "an" refer to one or to more than one (e.g., to at least one) of the grammatical object of the article. When used herein, the term "comprising" and variations thereof such as "comprises" and "comprise" can be substituted with the term "containing" or "including" or "having" or "has", respectively, and vice versa.

"Antibody molecules" or "antibodies" (used synonymously herein) are gamma globulin proteins that can be found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibody molecules can bind, by non-covalent interaction, to other molecules or structures known as antigens. This binding is specific in the sense that an antibody molecule will only bind to a specific structure with high affinity. The unique part of the antigen recognized by an antibody molecule is called an epitope, or antigenic determinant. The part of the antibody molecule binding to the epitope is sometimes called paratope, which is the molecular determinant within the antibody structure that makes specific interaction with the antigen; and the so-called variable domain composed of CDRs, or variable region (Fv) of the antibody. A paratope may comprise fully or in part CDRs of the heavy chain, light chain or both heavy and light chain of a given antibody. The variable domain comprises the three so-called complementary-determining regions (CDR's) spaced apart by framework regions (FR's).

The terms "complementarity determining region," and "CDR," are known in the art to refer to non-contiguous sequences of amino acids within antibody variable regions, which confer antigen specificity and binding affinity. In general, there are three (3) CDRs in each heavy chain variable region (CDR-H1, CDR-H2, CDR-H3) and three (3) CDRs in each light chain variable region (CDR-L1, CDR-L2, CDR-L3).

The amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, Md. ("Kabat" numbering scheme), A1-Lazikani et al., (1997) JMB 273, 927-948 ("Chothia" numbering scheme), MacCallum et al., J. Mol. Biol. 262:732-745 (1996), "Antibody-antigen interactions: Contact analysis and binding site topography," J. Mol. Biol. 262, 732-745. ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" or "CCG" numbering scheme), and Honegger A and Pltickthun A, "Yet another numbering scheme for immunoglobulin variable domains: an automatic modeling and analysis tool," J Mol Biol, 2001 Jun. 8; 309(3):657-70, (AHo numbering scheme).

The boundaries of a given CDR may vary depending on the naming convention. The amino acid positions assigned to CDRs and FRs can be defined for example according to the numbering system of Kabat, wherein the VH framework regions (FRs) and CDRs are positioned as follows: residues 1-30 (FR1), 31-35 (CDR1), 36-49 (FR2), 50-65 (CDR2), 66-94 (FR3), 95-102 (CDR3) and 103-113 (FR4). Also, according to the numbering system of Kabat, VL FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4).

Alternatively, the IMGT or CCG unique numbering has been defined to compare the variable domains whatever the antigen receptor, the chain type, or the species (Lefranc, M.-P., Pommié, C., Ruiz, M., Giudicelli, V., Foulquier, E., Truong, L., Thouvenin-Contet, V. and Lefranc, G., "IMGT unique numbering for immunoglobulin and T cell receptor variable domains and Ig superfamily V-like domains" Dev. Comp. Immunol., 27, 55-77 (2003)). In the IMGT unique numbering, the conserved amino acids always have the same position, for instance cysteine 23 (1st-CYS), tryptophan 41 (CONSERVED-TRP), hydrophobic amino acid 89, cysteine 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117.

Within the context of this invention, reference to CDRs is based on the definition of the CCG/IMGT convention, however, the present disclosure is not limited to FRs and CDRs as defined by any one numbering system, but includes all numbering systems, including those discussed above.

Thus, unless otherwise specified, the terms "CDR" and "complementary determining region" of a given antibody or region thereof, such as a variable region, as well as individual CDRs (e.g., "CDR-H1, CDR-H2) and framework regions (FRs) of the antibody or region thereof, should be understood to encompass respective region (e.g., the complementary determining region) as defined by any of the known schemes described herein above. In some instances, the scheme for identification of a particular CDR or CDRs is specified, such as the CDR as defined by the Kabat, Chothia, IMGT, AHO or other methods known in the art. In other cases, the particular amino acid sequence of a CDR is given.

In some embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In some embodiments the antibody has effector function and can fix complement. In other embodiments the antibody does not recruit effector cells or fix complement. In certain embodiments, the antibody has reduced or no ability to bind an Fc receptor. For example, it may be an isotype or subtype, fragment or other mutant, which does not support binding to an Fc receptor, e.g., it has a mutagenized or deleted Fc receptor binding region.

The antibody constant region is altered in some embodiments. Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP388,151A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions. In one embodiment, the antibody comprises a L234A and/or L235A mutation (Kabat nomenclature), corresponding to positions L232A and L233A in actual numbering of the exemplary antibodies described herein. In one embodiment, the antibody is a human IgG1.

The polypeptides of the invention may have a modified N-terminal sequence, e.g. a deletion of one or more of the N-terminal amino acids, or an exchange of e.g. the first, N-terminal amino acid (e.g. glutamate to alanine), to optimize the molecule for being expressed by using certain expression systems (such as specific vectors or host cells), or for being expressed as inclusion bodies or in soluble form, or for being secreted into the medium or the periplasmic space or for being contained within the cell, or for yielding a more homogenous product. The polypeptides of the invention may have a modified C-terminal sequence, such as an additional alanine, and/or further amino acid exchanges or deletions in the C-terminal part or at other defined positions within any of the framework regions, as explained e.g. in WO2012/175741, WO2011/075861, or WO2013/024059, in order to e.g. further enhance stability or reduce immunogenicity of such polypeptides.

The term "variable region", or "variable domain" as used herein interchangeably, means an region of the antibody molecule which essentially consists of four "framework regions" which are referred to in the art and hereinbelow as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and hereinbelow as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The terms "variable heavy (or VH)" and "variable light (or VL)" refer to the variable domains from the heavy or light chains, respectively, of an antibody molecule. Accordingly, the CDRs of the heavy chain (HC) are termed "HCDRs", and the CDRs of the light chain (LC) are termed "LCDRs", respectively.

The art has further developed antibody molecules and made them versatile tools in medicine and technology. Thus, in the context of the present invention the terms "antibody molecule" or "antibody" do not only include antibodies as they may be found in nature, comprising e.g. two light chains and two heavy chains, but furthermore encompasses all molecules comprising at least one paratope with binding specificity to an antigen and structural similarity to a variable domain of an antibody molecule.

Thus, an antibody molecule according to the invention includes a monoclonal antibody, a human antibody, or a humanized antibody.

Also contemplated are a chimeric antibody, a fragment of an antibody, in particular a Fv, Fab, Fab', or $F(ab')_2$ fragment, a single chain antibody, in particular a single chain variable fragment (scFv), a Small Modular Immunopharmaceutical (SMIP), a domain antibody, a nanobody, a diabody.

Monoclonal antibodies (mAb) are monospecific antibodies that are identical in amino acid sequence. They may be produced by hybridoma technology from a hybrid cell line (called hybridoma) representing a clone of a fusion of a specific antibody-producing B cell with a myeloma (B cell cancer) cell (Kohler G, Milstein C. Continuous cultures of fused cells secreting antibody of predefined specificity. Nature 1975; 256:495-7.). Alternatively, monoclonal antibodies may be produced by recombinant expression in host cells (Norderhaug L, Olafsen T, Michaelsen T E, Sandlie I. (May 1997). "Versatile vectors for transient and stable expression of recombinant antibody molecules in mammalian cells", J Immunol Methods 204 (1): 77-87. A "recombinant antibody" is an antibody which has been produced by a recombinantly engineered host cell. It is optionally isolated or purified.

For application in man, it is often desirable to reduce immunogenicity of antibodies originally derived from other species, like mouse. This can be done by construction of chimeric antibodies, or by a process called "humanization". In this context, a "chimeric antibody" is understood to be an antibody comprising a sequence part (e.g. a variable domain) derived from one species (e.g. mouse) fused to a sequence part (e.g. the constant domains) derived from a different species (e.g. human). A "humanized antibody" is an antibody comprising a variable domain originally derived from a non-human species, wherein certain amino acids have been mutated to make the overall sequence of that variable domain more closely resemble to a sequence of a human variable domain. Methods of chimerisation and humanization of antibodies are well-known in the art (Billetta R, Lobuglio A F. "Chimeric antibodies". Int Rev Immunol. 1993; 10(2-3):165-76; Riechmann L, Clark M, Waldmann H, Winter G (1988). "Reshaping human antibodies for therapy". Nature: 332:323.).

A "humanized" antibody refers to an antibody comprising amino acid residues from non-human hypervariable regions (HVRs) and amino acid residues from human FRs. In certain embodiments, a humanized antibody will comprise substantially all of at least one, and typically two, variable domains, in which all or substantially all of the HVRs (e.g. complementary determining regions (CDRs)) correspond to those of a non-human antibody, and all or substantially the entire framework regions (FRs) correspond to those of a human antibody. A humanized antibody optionally may comprise at least a portion of an antibody constant region derived from a human antibody. A "humanized form" of an antibody, e.g. a non-human antibody, refers to an antibody that has undergone humanization.

Furthermore, technologies have been developed for creating antibodies based on sequences derived from the human genome, for example by phage display or use of transgenic animals (WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93.; Brüggemann M, Taussig M J. "Production of human antibody repertoires in transgenic mice". Curr Opin Biotechnol. 1997 August; 8(4):455-8.). Such antibodies are "human antibodies" in the context of the present invention.

Also contemplated are fragments of the molecules which retain antigen binding properties, like Fab, Fab', or $F(ab')_2$ fragments. Such fragments may be obtained by fragmentation of antibody molecules e.g. by proteolytic digestion, or by recombinant expression of such fragments. For example, antibody molecule digestion can be accomplished by means of routine techniques, e.g. using papain or pepsin (WO 94/29348). Papain digestion of antibodies typically produces two identical antigen binding fragments, so-called Fab fragments, each with a single antigen binding site, and a residual Fc fragment. Pepsin treatment yields an $F(ab')_2$. In Fab molecules, the variable domains are each fused to an immunoglobulin constant domain, preferably of human origin. Thus, the heavy chain variable domain may be fused to a $CH_1$ domain (a so-called Fd fragment), and the light chain variable domain may be fused to a CL domain. Fab molecules may be produced by recombinant expression of respective nucleic acids in host cells, see below.

A number of technologies have been developed for placing variable domains of antibody molecules, or molecules derived from such variable domains, in a different molecular context. In general, these antibody molecules are smaller in size compared to natural antibody molecules, and may comprise a single amino acid chain or several amino acid chains. For example, a single-chain variable fragment (scFv) is a fusion of the variable regions of the heavy and light chains of antibody molecules, linked together with a short linker, usually serine (S) or glycine (G) (WO 88/01649; WO 91/17271; Huston et al; International Reviews of Immunology, Volume 10, 1993, 195-217). "Single domain antibodies" or "nanobodies" harbour an antigen-binding site in a single Ig-like domain (WO 94/04678; WO 03/050531, Ward et al., Nature. 1989 Oct. 12; 341(6242):544-6; Revets et al., Expert Opin Biol Ther. 5(1):111-24, 2005). One or more single domain antibodies with binding specificity for the same or a different antigen may be linked together. Diabodies are bivalent antibody molecules consisting of two amino acid chains comprising two variable domains (WO 94/13804, Holliger et al., Proc Natl Acad Sci USA. 1993 Jul. 15; 90(14):6444-8). Other examples of antibody-like molecules are immunoglobulin super family antibodies (IgSF; Srinivasan and Roeske, Current Protein Pept. Sci. 2005, 6(2): 185-96). A different concept leads to the so-called Small Modular Immunopharmaceutical (SMIP) which comprises a Fv domain linked to single-chain hinge and effector domains devoid of the constant domain CH1 (WO 02/056910).

The antibody molecule may be fused (as a fusion protein) or otherwise linked (by covalent or non-covalent bonds) to other molecular entities having a desired impact on the properties of the antibody molecule. For example, it may be desirable to improve pharmacokinetic properties of antibody molecules, stability e.g. in body fluids such as blood, in particular in the case of single chain antibodies or domain antibodies. A number of technologies have been developed in this regard, in particular to prolong the half-life of such antibody molecules in the circulation, such as pegylation (WO 98/25971; WO 98/48837; WO 2004081026), fusing or otherwise covalently attaching the antibody molecule to another antibody molecule having affinity to a serum protein like albumin (WO 2004041865; WO 2004003019), or expression of the antibody molecule as fusion protein with all or part of a serum protein like albumin or transferrin (WO 01/79258).

The terms "epitope" and "antigenic determinant", which can be used interchangeably, refer to the part of a macromolecule, such as a polypeptide, that is recognized by antigen-binding molecules, such as the antibody molecules of the invention, and more particularly by the antigen-binding site of said molecules. Epitopes define the minimum binding site for an antibody molecule, and thus represent the target of specificity of an antibody molecule. Epitopes can be further defined as structural epitopes or functional epitopes. A "structural epitope" consists of amino acids or other molecules in a region that is in close contact with the antibody usually revealed by a structure. A "functional epitope" is defined, as those parts of a molecule that make an energetic contribution to binding such that when they are changed there is a decrease in binding affinity. Therefore, the residues making contact with the paratope, and what residues that are contributing to the affinity, whether they are proximal or not are important considerations when defining the epitope. X-ray crystallography is one method to determine the precise sites of interaction between an antibody and its antigen. Crystal structures enable accurate determination of key interactions between individual amino acids from both side chains and main chain atoms in both the epitope and paratope. Amino acids that are within 4.5 Angstrom of each other are generally considered to be contacting residues.

An antibody molecule that can "bind", "bind to", "specifically bind", or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein.

Generally, the term "specificity" refers to the number of different types of antigens or epitopes to which a particular antigen-binding molecule or antigen-binding protein (such as an immunoglobulin, an antibody, an immunoglobulin single variable domain) can bind. The specificity of an antigen-binding protein can be determined based on its affinity and/or avidity. The affinity, represented by the equilibrium constant for the dissociation of an antigen with an antigen-binding protein ($K_D$), is a measure for the binding strength between an epitope and an antigen-binding site on the antigen-binding protein: the lesser the value of the $K_D$, the stronger the binding strength between an epitope and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as an antibody of the invention) and the pertinent antigen. Avidity is related to both the affinity between an epitope and its antigen binding site on the antigen-binding molecule and the number of pertinent binding sites present on the antigen-binding molecule.

Typically, antigen-binding proteins (such as the antibody molecules of the invention) will bind with a dissociation constant ($K_D$) of 10E-5 to 10E-14 moles/liter (M) or less, and preferably 10E-7 to 10E-14 moles/liter (M) or less, more preferably 10E-8 to 10E-14 moles/liter, and even more preferably 10E-11 to 10E-13 (as measured e.g. in a Kinexa assay; known in the art), and/or with an association constant ($K_A$) of at least 10E7 ME-1, preferably at least 10E8 ME-1, more preferably at least 10E9 ME-1, such as at least 10E11 ME-1. Any $K_D$ value greater than 10E-4 M is generally considered to indicate non-specific binding. Preferably, an antibody of the invention will bind to the desired antigen with a $K_D$ less than 500 nM, preferably less than 200 nM, more preferably less than 10 nM, such as less than 500 pM. Specific binding of an antigen-binding protein to an antigen or epitope can be determined in any suitable manner known per se, including, for example, the assays described herein such as surface plasmon resonance (SPR), Scatchard analysis and/or competitive binding assays, such as radioimmunoassays (RIA), enzyme immunoassays (EIA) and sandwich competition assays, and the different variants thereof known per se in the art.

The binding affinity of an antibody molecule may be enhanced by a process known as affinity maturation (Marks et al., 1992, Biotechnology 10:779-783; Barbas, et al., 1994, Proc. Nat. Acad. Sci, USA 91:3809-3813; Shier et al., 1995, Gene 169:147-155). Affinity matured antibodies are therefore also embraced in the present invention.

For example, affinity maturation of the inventive antibody may result in alterations of one or more amino acids introduced into the framework and/or CDR regions which may result in an improvement in the binding affinity for the antigen, without changing the specificity of the antibody for its epitope. Thus, embodiments of the invention include e.g. antibodies that specifically bind to CD73 comprising a heavy chain variable region having at least 90%, 91%, 92%, 93%, 94%, 95%, 96%, 97%, 98%, 99% amino acid sequence identity to SEQ ID NO: 73, SEQ ID NO: 75, SEQ ID NO: 77; SEQ ID NO: 79; SEQ ID NO: 81; SEQ ID NO: 83; SEQ ID NO: 85; SEQ ID NO: 87; SEQ ID NO: 89; SEQ ID NO: 91; SEQ ID NO: 93; SEQ ID NO: 95 and a light chain variable region having at least 90%, 91%, 92%, 93%, 94%, 95%, 96%, 97%, 98%, 99% amino acid sequence identity to SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96. For example, affinity maturated antibodies of the invention may comprise a light chain variable region as disclosed above comprising 1, 2, 3, 4, 5, 6, 7, 8, 9, or 10 amino acid substitutions, whereby the amino acid substitutions may be conservative amino acid substitutions, or non-conservative amino acid substitutions and/or a heavy chain variable region as disclosed above comprising 1, 2, 3, 4, 5, 6, 7, 8, 9, 10, or 11 amino acid substitutions, whereby the amino acid substitutions may be conservative amino acid substitutions, or non-conservative amino acid substitutions.

For example, the present invention also contemplates mutations in the antibody sequences according to the invention which may include substitutions, deletions, including internal deletions, additions, including additions yielding fusion proteins, or conservative substitutions of amino acid residues within and/or adjacent to the amino acid sequence, but that result in no functional ("silent") change, in that the change produces a functionally equivalent anti-CD73 antibody. Such change may e.g. comprise conservative amino acid substitutions which may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine, positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for a member of another class.

In one example, the present invention relates to anti-CD73 antibodies with enhanced effector function as well as altered/mutant derivatives thereof including, but not limited to ones exhibiting altered binding characteristics; e.g. altered association constants koN, dissociation constants kOFF, and/or equilibrium constant or binding affinity, $K_D$.

The compositions and methods disclosed herein encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared.

When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to a protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure which has little or essentially no influence on the function, activity or other biological properties of the polypeptide. Such conservative amino acid substitutions are well known in the art, for example from W01998/49185, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gin; (iii) polar, positively charged residues: His, Arg and Lys; (iv) large aliphatic, nonpolar residues: Met, Leu, Ile, Val and Cys; and (v) aromatic residues: Phe, Tyr and Trp. Particularly preferred conservative amino acid substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp or into Phe; Val into Ile or into Leu.

The terms "polypeptide", "peptide" and "protein" (if single chain) are used interchangeably herein.

The terms "nucleic acid," "nucleic acid sequence," "nucleotide sequence," or "polynucleotide sequence," and "polynucleotide" are used interchangeably.

The term "isolated," as used herein, refers to material that is removed from its original or native environment (e.g. the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Preferably, the nucleic acid will be part of an expression vector, wherein said nucleic acid molecule is operably linked to at least one regulatory sequence, wherein such regulatory sequence may be a promoter, enhancer, or terminator sequence, and most preferably a heterologous promotor, enhancer, or terminator sequence.

The terms "PD1" and "PD-1" are used interchangeably herein. The terms "PDL1" and "PDL-1" are likewise used interchangeably herein. PD1-1, PD1-2, PD1-3, PD1-4, and PD1-5 as disclosed herein below refer to specific anti-PD-1 antibodies, respectively.

"MED19447" and "BMS986179", as used herein, when written in quotation marks (" "), refer to reference antibodies that were generated according to information as disclosed in WO 2016/075099 ("MED19447") and WO 2016/081748 ("BMS986179", also termed mAb-CD73.4-Vh-hHC-IgG2-IgG1.1f therein), respectively. WO 2016/075099 and WO 2016/081748, respectively, are hereby incorporated by reference in their entirety.

For the avoidance of doubt, by "Cluster of Differentiation 73" or "CD73" we mean the human protein encoded by the gene "NTSE 5'-nucleotidase ecto [*Homo sapiens* (human)]", which is provided in NCBI Reference Sequence: NP_002517.1, accessible at w w w ncbi.nlm.nih.gov/protein/NP_002517.1 (Long isoform, which corresponds to UniProt accession no. P21589), as well as NCBI Reference Sequence: NP_001191742.1, accessible at w w w ncbi.nlm-.nih.gov/protein/NP_001191742.1 (Short isoform), and the respective nucleic acid sequences encoding these proteins. As used herein, "CD73" may refer to the monomeric and/or dimeric form of these proteins. In some embodiments, "CD73" refers to the long isoform of human CD73 as described above. For crystallographic data as provided herein amino acid numbering corresponds to Uniprot accession no. P21589, including the signal peptide, whereby the mature protein is devoid of the signal peptide corresponding to amino acid residues 1-26 of P21589, however, the numbering scheme throughout this application will refer to the full length amino acid sequence of P21589. Murine CD73 as used herein refers to Uniprot accession no. Q61503.

In living cells and organisms, CD73 is usually present as a dimeric protein anchored to the cell membrane through a glycosylphosphatidylinositol (GPI) membrane linkage (also termed "GPI anchor" herein), and has ecto-5'-nucleotidase activity.

The terms "soluble CD73", and "sCD73", which are used interchangeably herein, mean CD73 molecules which are not attached to a membrane, e.g. via a GPI anchor.

The term "cell-bound CD73" means CD73 molecules which are attached to a cell surface, e.g. via a GPI anchor.

The term "non-cell-bound CD73" refers to CD73 that is present in the extracellular space. It includes both soluble CD73 and vesicle-bound CD73, i.e. CD73 molecules which are attached to the surface of vesicles in the extracellular space. The term "non-cell-bound CD73" excludes all "cell-bound CD73". Activity of "non-cell-bound CD73" can be determined by measuring CD73 activity in cell culture supernatants as described in Example 8.

The terms "IFNγ", "IFNg", "interferon gamma", "interferon-gamma", "IFN-gamma", "IFNG", "IFN gamma", "IFN-γ", or similar, are used interchangeably herein, and denote the cytokine of the interferon family as known in the art (NCBI Gene ID: 3458), which is secreted by cells of both the innate and adaptive immune systems, such as T cells.

Anti-CD73 Antibodies of the Invention

As detailed above, CD73 plays an important role in regulating T-cell activity and hence immune system activity. It has been shown in a range of different cancer settings that antagonistic anti-CD73 antibody molecules can reverse adenosine-mediated suppression of T-cell activity, thereby activating the immune system to attack tumors and so treat cancer.

The present invention provides improved anti-CD73 antibodies. Starting from progenitor murine antibodies to CD73, termed A1, A2, A3 and A4 (see Table 9), humanized variants were generated. Preferred anti-CD73 antibody molecules of the present invention are termed B1, B2, C1, C2, C3, C4, C5 and C6 (see Table 9), which are humanized monoclonal antibodies. Anti-CD73 antibodies of the invention may e.g. also be referred to as "antagonistic CD73 antibody" or "antagonistic CD73 antibodies", whereby the term "antagonistic" or any gramatical equivalent thereof refers to the inhibition of CD73 function (e.g. soluble and cell-surface bound) by the inventive CD73 antibody.

Using an in-vitro T-cell activation assay (further described in Example 6) the present inventors examined functional characteristics of representative anti-CD73 antibodies of the present invention. As can be seen in Example 6 and Table 5 and 6, the tested antibodies were able to induce T-cell proliferation to a higher level in comparison to reference anti-CD73 antibodies in certain donors. In addition the tested antibodies were able to induce higher IFNγ levels in T cells compared to reference anti-CD73 antibodies in certain donors. As can be appreciated, this surprising ability of the anti-CD73 antibodies of the present invention to more effectively induce T-cell activation than the prior art reference anti-CD73 antibody suggests that they may provide a more effective treatment of cancer and/or improved clinical outcome.

The inventors further investigated various other functional characteristics of the anti-CD73 antibody molecules of the present invention. Included in this assessment was the determination of the capacity to inhibit adenosine formation by anti-CD73 antibodies. This was done by measuring inhibition of cell-bound CD73 as well as inhibition of non-cell-bound CD73 in cell culture supernatants. Anti-CD73 antibodies of the present invention showed higher activity in inhibiting non-cell-bound CD73 compared to reference anti-CD73 antibodies. Thus, these antibodies have the capacity to lead to a more complete inhibition of CD73 compared to reference CD73 antibodies.

In contrast to the anti-CD73 antibodies known in the art, the anti-CD73 antibodies of the invention have improved properties, in particular in terms of the inhibition of adenosine generation and T cell activation. This is in contrast to the known reference anti-CD73 antibody molecules "MED19447" and "BMS986179", as can be seen from the accompanying examples. As can be appreciated, this superiority of the anti-CD73 antibody molecules of the present invention, suggests that they may have a higher efficacy and/or better clinical outcome than other anti-CD73 antibodies and thus may allow for a more effective cancer therapy.

Accordingly therefore a first aspect of the invention provides anti-CD73 antibody molecules, comprising:

(1) heavy chain CDRs comprising the amino acid sequence of SEQ ID NO:1 (hcCDR1), SEQ ID NO:2 (hcCDR2) and SEQ ID NO:3 (hcCDR3) and light chain CDRs comprising the amino acid sequence of SEQ ID NO:4 (lcCDR1), SEQ ID NO:5 (lcCDR2) and SEQ ID NO:6 (lcCDR3); or (2) heavy chain CDRs comprising the amino acid sequence of SEQ ID NO:7 (hcCDR1), SEQ ID NO:8 (hcCDR2) and SEQ ID NO:9 (hcCDR3) and light chain CDRs comprising the amino acid sequence of SEQ ID NO:10 (lcCDR1), SEQ ID NO:11 (lcCDR2) and SEQ ID NO:12 (lcCDR3); or (3) heavy chain CDRs comprising the amino acid sequence of SEQ ID NO:13 (hcCDR1), SEQ ID NO:14 (hcCDR2) and SEQ ID NO:15 (hcCDR3) and light chain CDRs comprising the amino acid sequence of SEQ ID NO:16 (lcCDR1), SEQ ID NO:17 (lcCDR2) and SEQ ID NO:18 (lcCDR3); or (4) heavy chain CDRs comprising the amino acid sequence of SEQ ID NO:19 (hcCDR1), SEQ ID NO:20 (hcCDR2) and SEQ ID NO:21 (hcCDR3) and light chain CDRs comprising the amino acid sequence of SEQ ID NO:22 (lcCDR1), SEQ ID NO:23 (lcCDR2) and SEQ ID NO:24 (lcCDR3); or (5) heavy chain CDRs comprising the amino acid sequence of SEQ ID NO:25 (hcCDR1), SEQ ID NO:26 (hcCDR2) and SEQ ID NO:27 (hcCDR3) and light chain CDRs comprising the amino acid sequence of SEQ ID NO:28 (lcCDR1), SEQ ID NO:29 (lcCDR2) and SEQ ID NO:30 (lcCDR3); or, (6) heavy chain CDRs comprising the amino acid sequence of SEQ ID NO:31 (hcCDR1), SEQ ID NO:32 (hcCDR2) and SEQ ID NO:33 (hcCDR3) and light chain CDRs comprising the amino acid sequence of SEQ ID NO:34 (lcCDR1), SEQ ID NO:35 (lcCDR2) and SEQ ID NO:36 (lcCDR3); or, (7) heavy chain CDRs comprising the amino acid sequence of SEQ ID NO:37 (hcCDR1), SEQ ID NO:38 (hcCDR2) and SEQ ID NO:39 (hcCDR3) and light chain CDRs comprising the amino acid sequence of SEQ ID NO:40 (lcCDR1), SEQ ID NO:41 (lcCDR2) and SEQ ID NO:42 (lcCDR3); or (8) heavy chain CDRs comprising the amino acid sequence of SEQ ID NO:43 (hcCDR1), SEQ ID NO:44 (hcCDR2) and SEQ ID NO:45 (hcCDR3) and light chain CDRs comprising the amino acid sequence of SEQ ID NO:46 (lcCDR1), SEQ ID NO:47 (lcCDR2) and SEQ ID NO:48 (lcCDR3); or (9) heavy chain CDRs comprising the amino acid sequence of SEQ ID NO:49 (hcCDR1), SEQ ID NO:50 (hcCDR2) and SEQ ID NO:51 (hcCDR3) and light chain CDRs comprising the amino acid sequence of SEQ ID NO:52 (lcCDR1), SEQ ID NO:53 (lcCDR2) and SEQ ID NO:54 (lcCDR3); or

(10) heavy chain CDRs comprising the amino acid sequence of SEQ ID NO:55 (hcCDR1), SEQ ID NO:56 (hcCDR2) and SEQ ID NO:57 (hcCDR3) and light chain CDRs comprising the amino acid sequence of SEQ ID NO:58 (lcCDR1), SEQ ID NO:59 (lcCDR2) and SEQ ID NO:60 (lcCDR3); or

(11) heavy chain CDRs comprising the amino acid sequence of SEQ ID NO:61 (hcCDR1), SEQ ID NO:62 (hcCDR2) and SEQ ID NO:63 (hcCDR3) and light chain CDRs comprising the amino acid sequence of SEQ ID NO:64 (lcCDR1), SEQ ID NO:65 (lcCDR2) and SEQ ID NO:66 (lcCDR3); or

(12) heavy chain CDRs comprising the amino acid sequence of SEQ ID NO:67 (hcCDR1), SEQ ID NO:68 (hcCDR2) and SEQ ID NO:69 (hcCDR3) and light chain CDRs comprising the amino acid sequence of SEQ ID NO:70 (lcCDR1), SEQ ID NO:71 (lcCDR2) and SEQ ID NO:72 (lcCDR3).

As outlined above, preferred anti-CD73 antibody molecules of the present invention are termed B1, B2, C1, C2, C3, C4, C5 and C6. Provided herein is a sequence table (Table 9) which readily allows identification of individual amino acid sequences to specific anti-CD73 antibody molecules of the present invention.

In addition to the CDR sequences as set out herein, the antibody molecules of the invention include immunoglobulin framework region (FR) sequences. These sequences are preferably not immunogenic in humans, and are therefore preferably human or humanized FR sequences. Suitable human or humanized FR sequences are known in the art. Specifically preferred FR sequences can be taken from the embodiments shown herein, disclosing the complete antibody molecules and thereby CDR sequences as well as FR sequences.

Methods of preparing antibody molecules of the first aspect of the invention are well known in the art, and the skilled person would readily be able to prepare an antibody molecule having the characteristic of the first aspect of the invention. Examples of such methods are provided below.

For production of antibodies comprising two complete heavy and two complete light chains, like those of the IgG1 or IgG4 type, see Norderhaug et al., J Immunol Methods 1997, 204 (1): 77-87; Kipriyanow and Le Gall, Molecular Biotechnology 26: 39-60, 2004; Shukla et al., 2007, J. Chromatography B, 848(1): 28-39.

Processes for manufacturing scFv antibodies by recombinant expression of nucleic acids encoding scFv constructs in host cells (like *E. coli, Pichia pastoris*/Komagataella phaffii, or mammalian cell lines, e.g. CHO or NSO), yielding functional scFv molecules, are also known (Rippmann et al., Applied and Environmental Microbiology 1998, 64(12): 4862-4869; Yamawaki et al., J. Biosci. Bioeng. 2007, 104 (5): 403-407; Sonoda et al., Protein Expr. Purif. 2010, 70(2): 248-253).

For the avoidance of doubt, each of the specific embodiments listed herein for the first aspect of the invention can also be considered for independent aspects of the invention.

A preferred embodiment of the first aspect of the invention is wherein said antibody molecule is a humanized antibody molecule.

In one embodiment, said antibody is a recombinant antibody. In one embodiment, said antibody is isolated. In one embodiment, said antibody is purified.

A further preferred embodiment of the first aspect of the invention is wherein said antibody molecule is a monoclonal antibody, Fab, F(ab')2, Fv or scFv.

The terms "humanized", "Fab", "F(ab')2", "Fv" and "scFv" are well known in the art and further discussed herein in the Definitions section of the specification.

In a preferred embodiment, the anti-CD73 antibody molecule has a heavy chain constant region selected from the group consisting of IgG1, IgG2, IgG3, IgG4, IgM, IgA and IgE constant regions. Preferably the heavy chain constant region is IgG1, more preferably IgG1 with a L234A and/or a L235A mutation (Kabat numbering; corresponding to positions L232A and L233A in actual numbering).

In a preferred embodiment, the anti-CD73 antibody molecule has a light chain constant region which is kappa or lambda.

In one embodiment, the anti-CD73 antibody molecule has a heavy chain variable domain comprising an amino acid sequence at least 85%, 90%, 95% identical to any of SEQ ID NOs: 73, 75, 77 or 79 as disclosed above.

In one embodiment said antibody molecule has a heavy chain variable domain comprising an amino acid sequence of any of SEQ ID NOs: 73, 75, 77 or 79.

In a preferred embodiment, the anti-CD73 antibody molecule has a heavy chain variable domain comprising an amino acid sequence at least 85%, 90%, 95% identical to any of SEQ ID NOs: 81, 83, 85, 87, 89, 91, 93, or 95. Preferably said antibody molecule has a heavy chain variable domain comprising an amino acid sequence of any of SEQ ID NOs: 81, 83, 85, 87, 89, 91, 93, or 95. More preferably said antibody is humanized.

In one embodiment, the anti-CD73 antibody molecule has a light chain variable domain comprising an amino acid sequence at least 85% identical to any of SEQ ID NOs: 74, 76, 78 or 80.

In one embodiment said antibody molecule has a light chain variable domain comprising an amino acid sequence of any of SEQ ID NOs: 74, 76, 78 or 80.

In a preferred embodiment the anti-CD73 antibody molecules has a light chain variable domain comprising an amino acid sequence at least 85% identical to any of SEQ ID NOs: 82, 84, 86, 88, 90, 92, 94 or 96. Preferably said antibody molecule has a light chain variable domain comprising the amino acid sequence of SEQ ID NOs: 82, 84, 86, 88, 90, 92, 94 or 96. More preferably said antibody is humanized.

Methods of calculating amino acid sequence identities are well known in the art and further discussed herein in the Definitions section of the specification.

In a preferred embodiment, the anti-CD73 antibody molecule has a heavy chain variable region comprising the amino acid sequence of SEQ ID NO: 81.

In a preferred embodiment, the anti-CD73 antibody molecule has a heavy chain variable region comprising the amino acid sequence of SEQ ID NO: 83.

In a preferred embodiment, the anti-CD73 antibody molecule has a heavy chain variable region comprising the amino acid sequence of SEQ ID NO: 85.

In a preferred embodiment, the anti-CD73 antibody molecule has a heavy chain variable region comprising the amino acid sequence of SEQ ID NO: 87.

In a preferred embodiment, the anti-CD73 antibody molecule has a heavy chain variable region comprising the amino acid sequence of SEQ ID NO: 89.

In a preferred embodiment, the anti-CD73 antibody molecule has a heavy chain variable region comprising the amino acid sequence of SEQ ID NO: 91.

In a preferred embodiment, the anti-CD73 antibody molecule has a heavy chain variable region comprising the amino acid sequence of SEQ ID NO: 93.

In a preferred embodiment, the anti-CD73 antibody molecule has a heavy chain variable region comprising the amino acid sequence of SEQ ID NO: 95.

In a preferred embodiment, the anti-CD73 antibody molecule has a light chain variable region comprising the amino acid sequence of SEQ ID NO: 82.

In a preferred embodiment, the anti-CD73 antibody molecule has a light chain variable region comprising the amino acid sequence of SEQ ID NO: 84.

In a preferred embodiment, the anti-CD73 antibody molecule has a light chain variable region comprising the amino acid sequence of SEQ ID NO: 86.

In a preferred embodiment, the anti-CD73 antibody molecule has a light chain variable region comprising the amino acid sequence of SEQ ID NO: 88.

In a preferred embodiment, the anti-CD73 antibody molecule has a light chain variable region comprising the amino acid sequence of SEQ ID NO: 90.

In a preferred embodiment, the anti-CD73 antibody molecule has a light chain variable region comprising the amino acid sequence of SEQ ID NO: 92.

In a preferred embodiment, the anti-CD73 antibody molecule has a light chain variable region comprising the amino acid sequence of SEQ ID NO: 94.

In a preferred embodiment, the anti-CD73 antibody molecule has a light chain variable region comprising the amino acid sequence of SEQ ID NO: 96.

In a preferred embodiment, the anti-CD73 antibody molecule has a heavy chain comprising the amino acid sequence of SEQ ID NO: 105.

In a preferred embodiment, the anti-CD73 antibody molecule has a heavy chain comprising the amino acid sequence of SEQ ID NO: 107.

In a preferred embodiment, the anti-CD73 antibody molecule has a heavy chain comprising the amino acid sequence of SEQ ID NO: 109.

In a preferred embodiment, the anti-CD73 antibody molecule has a heavy chain comprising the amino acid sequence of SEQ ID NO: 111.

In a preferred embodiment, the anti-CD73 antibody molecule has a heavy chain comprising the amino acid sequence of SEQ ID NO: 113.

In a preferred embodiment, the anti-CD73 antibody molecule has a heavy chain comprising the amino acid sequence of SEQ ID NO: 115.

In a preferred embodiment, the anti-CD73 antibody molecule has a heavy chain comprising the amino acid sequence of SEQ ID NO: 117.

In a preferred embodiment, the anti-CD73 antibody molecule has a heavy chain comprising the amino acid sequence of SEQ ID NO: 119.

In a preferred embodiment, the anti-CD73 antibody molecule has a light chain comprising the amino acid sequence of SEQ ID NO: 106.

In a preferred embodiment, the anti-CD73 antibody molecule has a light chain comprising the amino acid sequence of SEQ ID NO: 108.

In a preferred embodiment, the anti-CD73 antibody molecule has a light chain comprising the amino acid sequence of SEQ ID NO: 110.

In a preferred embodiment, the anti-CD73 antibody molecule has a light chain comprising the amino acid sequence of SEQ ID NO: 112.

In a preferred embodiment, the anti-CD73 antibody molecule has a light chain comprising the amino acid sequence of SEQ ID NO: 114.

In a preferred embodiment, the anti-CD73 antibody molecule has a light chain comprising the amino acid sequence of SEQ ID NO: 116.

In a preferred embodiment, the anti-CD73 antibody molecule has a light chain comprising the amino acid sequence of SEQ ID NO: 118.

In a preferred embodiment, the anti-CD73 antibody molecule has a light chain comprising the amino acid sequence of SEQ ID NO: 120.

In one embodiment, the anti-CD73 antibody molecule has a heavy chain variable region comprising the amino acid sequence of SEQ ID NO: 73 and a light chain variable region comprising the amino acid sequence of SEQ ID NO: 74.

In one embodiment, the anti-CD73 antibody molecule has a heavy chain variable region comprising the amino acid sequence of SEQ ID NO: 75 and a light chain variable region comprising the amino acid sequence of SEQ ID NO: 76.

In one embodiment, the anti-CD73 antibody molecule has a heavy chain variable region comprising the amino acid sequence of SEQ ID NO: 77 and a light chain variable region comprising the amino acid sequence of SEQ ID NO: 78.

In one embodiment, the anti-CD73 antibody molecule has a heavy chain variable region comprising the amino acid sequence of SEQ ID NO: 79 and a light chain variable region comprising the amino acid sequence of SEQ ID NO: 80.

In a preferred embodiment, the anti-CD73 antibody molecule has a heavy chain variable region comprising the amino acid sequence of SEQ ID NO: 81 and a light chain variable region comprising the amino acid sequence of SEQ ID NO: 82.

In a preferred embodiment, the anti-CD73 antibody molecule has a heavy chain variable region comprising the amino acid sequence of SEQ ID NO: 83 and a light chain variable region comprising the amino acid sequence of SEQ ID NO: 84.

In a preferred embodiment, the anti-CD73 antibody molecule has a heavy chain variable region comprising the amino acid sequence of SEQ ID NO: 85 and a light chain variable region comprising the amino acid sequence of SEQ ID NO: 86.

In a preferred embodiment, the anti-CD73 antibody molecule has a heavy chain variable region comprising the amino acid sequence of SEQ ID NO: 87 and a light chain variable region comprising the amino acid sequence of SEQ ID NO: 88.

In a preferred embodiment, the anti-CD73 antibody molecule has a heavy chain variable region comprising the amino acid sequence of SEQ ID NO: 89 and a light chain variable region comprising the amino acid sequence of SEQ ID NO: 90.

In a preferred embodiment, the anti-CD73 antibody molecule has a heavy chain variable region comprising the amino acid sequence of SEQ ID NO: 91 and a light chain variable region comprising the amino acid sequence of SEQ ID NO: 92.

In a preferred embodiment, the anti-CD73 antibody molecule has a heavy chain variable region comprising the amino acid sequence of SEQ ID NO: 93 and a light chain variable region comprising the amino acid sequence of SEQ ID NO: 94.

In a preferred embodiment, the anti-CD73 antibody molecule has a heavy chain variable region comprising the amino acid sequence of SEQ ID NO: 95 and a light chain variable region comprising the amino acid sequence of SEQ ID NO: 96.

In one embodiment, the anti-CD73 antibody molecule has a heavy chain comprising the amino acid sequence of SEQ ID NO: 97 and a light chain comprising the amino acid sequence of SEQ ID NO: 98.

In one embodiment, the anti-CD73 antibody molecule has a heavy chain comprising the amino acid sequence of SEQ ID NO: 99 and a light chain comprising the amino acid sequence of SEQ ID NO: 100.

In one embodiment, the anti-CD73 antibody molecule has a heavy chain comprising the amino acid sequence of SEQ ID NO: 101 and a light chain comprising the amino acid sequence of SEQ ID NO: 102.

In one embodiment, the anti-CD73 antibody molecule has a heavy chain comprising the amino acid sequence of SEQ ID NO: 103 and a light chain comprising the amino acid sequence of SEQ ID NO: 104.

In a preferred embodiment, the anti-CD73 antibody molecule has a heavy chain comprising the amino acid sequence of SEQ ID NO: 105 and a light chain comprising the amino acid sequence of SEQ ID NO: 106.

In a preferred embodiment, the anti-CD73 antibody molecule has a heavy chain comprising the amino acid sequence of SEQ ID NO: 107 and a light chain comprising the amino acid sequence of SEQ ID NO: 108.

In a preferred embodiment, the anti-CD73 antibody molecule has a heavy chain comprising the amino acid sequence of SEQ ID NO: 109 and a light chain comprising the amino acid sequence of SEQ ID NO: 110.

In a preferred embodiment, the anti-CD73 antibody molecule has a heavy chain comprising the amino acid sequence of SEQ ID NO: 111 and a light chain comprising the amino acid sequence of SEQ ID NO: 112.

In a preferred embodiment, the anti-CD73 antibody molecule has a heavy chain comprising the amino acid sequence of SEQ ID NO: 113 and a light chain comprising the amino acid sequence of SEQ ID NO: 114.

In a preferred embodiment, the anti-CD73 antibody molecule has a heavy chain comprising the amino acid sequence of SEQ ID NO: 115 and a light chain comprising the amino acid sequence of SEQ ID NO: 116.

In a preferred embodiment, the anti-CD73 antibody molecule has a heavy chain comprising the amino acid sequence of SEQ ID NO: 117 and a light chain comprising the amino acid sequence of SEQ ID NO: 118.

In a preferred embodiment, the anti-CD73 antibody molecule has a heavy chain comprising the amino acid sequence of SEQ ID NO: 119 and a light chain comprising the amino acid sequence of SEQ ID NO: 120.

For all of the above embodiments it shall be understood that, by using the term "comprising", it is intended to also include an embodiment in which the respective domain or molecule "consists" of the amino acid sequence as indicated.

In a preferred embodiment, the anti-CD73 antibody molecule is capable of binding to human CD73 with a dissociation constant ($K_D$) of less than 10 nM, preferably less than 1 nM, more preferably less than 100 pM.

In some embodiments, the anti-CD73 antibody molecule is capable of binding to human CD73 (long isoform) and cynomolgus monkey (*Macaca fascicularis*) CD73 with high affinity. In some embodiments, high affinity refers to a $K_D$ of less than 10 nM e.g. 9, 8, 7, 6 or lower, as measured by surface plasmon resonance (SPR). In preferred embodiments, high affinity refers to a $K_D$ of less than 1 nM, as measured by SPR. In more preferred embodiments, the anti-CD73 antibody molecule is capable of binding to human CD73 with a $K_D$ of less than 500 pM. In the most preferred embodiment, the antibody binds to human CD73 with a $K_D$ of less than 100 pM. A protocol for determining $K_D$ using SPR is provided in the accompanying examples.

In a preferred embodiment, the anti-CD73 antibody molecule binds to mouse CD73 with lower affinity compared to human CD73, such as 10×, 50×, 100× or 110× lower affinity compared to human CD73. The sequence of mouse CD73 is accessible by Gen Bank accession number NP_035981.1 (only 1 form identified). The sequence of cynomolgous CD73 is accessible by RefSeq accession No XP_005552488.1.

In one embodiment, the anti-CD73 antibody molecule is capable of reducing the activity of human CD73. In some embodiments, the activity of human CD73 refers to the enzymatic function of hydrolysing AMP to adenosine. Accordingly, reducing the activity of human CD73 refers to inhibiting such enzymatic function. In one embodiment, the anti-CD73 antibody inhibits enzymatic function of human CD73 in vitro as described in the Examples. In some embodiments, reducing the activity of human CD73 refers to a reduction of the cell surface levels of CD73. In another embodiment, the inhibition (by blocking the CD73 enzymatic function or by reducing CD73 cell surface levels) is determined in a cell based assay, e.g. using a cancer cell line such as Colo201.

In some embodiments, the anti-CD73 antibody molecule inhibits the formation of adenosine by at least 70%, preferably by more than 80%, as determined in a cell based assay as described in Example 5. In particularly preferred embodiments, the anti-CD73 antibody molecule inhibits the formation of adenosine by at least 60%, at least 70%, preferably by more than 75% in cell culture supernatants, i.e. it inhibits the activity of non-cell-bound CD73 as described in Example 8. In one embodiment, the anti-CD73 antibody molecule inhibits the formation of adenosine by non-cell-bound CD73 by at least 70%.

In yet a further embodiment, the anti-CD73 antibody inhibits enzymatic function of human CD73 in vivo.

Assays to determine the inhibition of enzymatic activity of human CD73 in vitro or in vivo are known in the art, and are also described in further detail in the accompanying examples.

In some embodiments, the anti-CD73 antibody molecule is capable of inhibiting the enzymatic activity of human CD73 with an 1090 of less than 5 nM, or 4, 3, 2, 1.5, 1, 0.5 nM or lower. In particularly preferred embodiments, the anti-CD73 antibody molecule inhibits the enzymatic activity of human CD73 with an $IC_{90}$ of less than 0.4 nM. A protocol for determining $IC_{90}$ is provided in the accompanying examples. In some embodiments, the anti-CD73 antibody inhibits human CD73 with an $IC_{90}$ of less than 1 nM, but only moderately reduces cell surface levels of CD73 (i.e. by less than 30%, less than 25% or less than 20%).

In one embodiment, the anti-CD73 antibody is capable of reversing the AMP-dependent suppression of T cell function. In a preferred embodiment, T cell function refers to T cell proliferation, which is known to be suppressible by adenosine that is generated by CD73 from adenosine monophosphate (AMP). The antibody of the invention is able to reverse this suppression by inhibiting adenosine production by CD73, preferably to a level substantially the same as the control level (stimulated T cells treated with isotype control without AMP addition). In preferred embodiments, the antibody of the invention is capable to restore the proliferation of T cells to 40%, 50%, 60%, 70%, 80%, 85%, 90%, 95%, 96%, 97%, 98%, 99% or 100%, or even more than 100%, such as 110%, 115%, 120% or 125% of the control level. An assay to determine AMP-dependent suppression of T cell function is described in Example 6. In some embodiments, the T cells are CD4+. In other embodiments, the T cells are CD8+.

In some embodiments, T cell function refers to interferon gamma release by T cells. Without wishing to be bound to any theory, it is believed that adenosine produced by CD73 suppresses such interferon gamma release by T cells. Accordingly, the antibody of the invention is able to restore interferon gamma release by T cells, preferably to a level substantially the same as the control level (stimulated T cells treated with isotype control without AMP addition). In preferred embodiments, the antibody of the invention is capable to induce interferon gamma release of T cells suppressed by AMP up to a value of 2× (i.e. two-fold), 3×, 5×, 10×, 20×, 30×, 40×50×, or more than 50× of the control level (stimulated T cells treated with isotype control with AMP addition). An assay to determine interferon gamma release of T cells is described in Example 6. In some embodiments, the T cells are CD4+. In other embodiments, the T cells are CD8+.

In a particularly preferred embodiment, T cell function refers to both T cell proliferation and interferon gamma release as described above, i.e. the anti-CD73 antibodies are capable of stimulating both T cell proliferation and interferon gamma release of T cells.

In a further embodiment, the anti-CD73 antibody molecule forms antigen-antibody complexes with soluble CD73 with a defined size, such as a 2:2 oligomer. These complexes are smaller compared to complexes formed by other CD73 antibodies known in the art (see e.g. FIG. 2). Size of antigen-antibody complexes has previously been linked to Fcγ receptor activation, and might therefore play a role in undesired immunogenicity (Krayukhina et al., Analytical ultracentrifugation with fluorescence detection system reveals differences in complex formation between recombinant human TNF and different biological TNF antagonists in various environments (2017). mAbs).

In some embodiments, the present invention provides anti-CD73 antibodies that bind to the same epitope as the antibodies A1, A2, A3, A4, B1, B2, C1, C2, C3, C4, C5, or C6 described herein (as referenced in Table 9). In some embodiments, the anti-CD73 antibody competes for binding to the same epitope as A1, A2, A3, A4, B1, B2, C1, C2, C3, C4, C5, or C6 (as referenced in Table 9). In some embodiments, the anti-CD73 antibody binds to an epitope that overlaps with, or substantially overlaps with, the epitope of A1, A2, A3, A4, B1, B2, C1, C2, C3, C4, C5, or C6 (as referenced in Table 9). Preferably, said anti-CD73 antibody is a monoclonal antibody.

In one embodiment the inventive anti-CD73 antibody as disclosed above comprises a light chain variable region paratope which binds to at least two, three, four, five, six, seven, eight, nine, ten, or all of the following amino acids on CD73 (Uniprot No. P21589): F137, P138, 1139, A151, S152, S155, G156, L157, Y158, L159, P160, Y161, K162, E203 and K206, whereby the binding of the light chain variable region to said amino acid residues on CD73 contributes to the inhibition of CD73 function by the inventive anti-CD73 antibody.

According to a preferred embodiment the inventive anti-CD73 antibody as disclosed above comprises a light chain variable region paratope which e.g. binds to at least two, three, four, five, six, seven, eight, nine, ten, or all of the amino acid residues as disclosed above, e.g. F137, P138, 1139, A151, S152, S155, G156, L157, Y158, L159, P160, Y161, K162, E203 and K206, which are part of the conformational epitope on CD73 which comprises amino acid residues F137, P138, 1139, A151, S152, G156, L157, Y158, L159, P160, Y161, K162, V163, P165, G167, D168, E169, V170, E203, K206, T209, L210, N211 (amino acid numbering corresponds to Uniprot accession no. P21589, including signal peptide, whereby the mature protein is devoid of the signal peptide comprising amino acid residues 1-26, however, the numbering scheme throughout this application will refer to the full length amino acid sequence of P21589) which is specifically bound by the inventive anti-CD73 antibody, whereby the variable light chain of the inventive anti-CD73 antibody comprises one amino acid sequence according to SEQ ID NO: 78, SEQ ID NO: 86, SEQ ID NO: 88, SEQ ID NO: 90, SEQ ID NO: 92, SEQ ID NO: 94, SEQ ID NO: 96. The term "conformational epitope" according to the invention which is bound by the inventive anti-CD73 antibody as disclosed herein refers to a non-linear epitope in which the epitope recognized and bound by the inventive antibody is formed by the secondary and/or tertiary structure of a polypeptide or protein and which is unique to a folded three-dimensional conformation of the polypeptide or protein. Generally, a conformational epitope consists of amino acids that are discontinuous in the linear sequence that come together in the folded structure of the protein. However, a conformational epitope may also consist of a linear sequence of amino acids that adopts a conformation that is unique to a folded three-dimensional conformation of the polypeptide and which is not present in a denatured state of said polypeptide or protein.

According to one embodiment, the inventive anti-CD73 antibody as disclosed above comprises a heavy chain variable region paratope which binds to at least two, three, four, five, six, seven, eight, nine, ten, or all of the following amino acid residues L159, P160, Y161, K162, V163, P165, G167, D168, E169, V170, T209, L210 and N211 which are part of the conformational epitope on CD73 which comprises amino acid residues F137, P138, 1139, A151, S152, G156, L157, Y158, L159, P160, Y161, K162, V163, P165, G167, D168, E169, V170, E203, K206, T209, L210, N211 (amino acid numbering corresponds to Uniprot accession no. P21589), whereby the binding of the heavy chain variable region to said amino acid residues on CD73 contributes to the inhibition of CD73 function by the inventive anti-CD73 antibody.

According to a one embodiment, the inventive anti-CD73 antibody as disclosed above comprise a heavy chain variable region paratope which comprises one of the amino acid sequence according to SEQ ID NO: 85, SEQ ID NO: 87, SEQ ID NO: 89, SEQ ID NO: 91, SEQ ID NO: 93, SEQ ID NO: 95 and binds to at least two, three, four, five, six, seven, eight, nine, ten, or all of the amino acid residues L159, P160, Y161, K162, V163, P165, G167, D168, E169, V170, T209, L210 and N211 on CD73 which are part of the conformational epitope formed by amino acids F137, P138, 1139, A151, S152, G156, L157, Y158, L159, P160, Y161, K162, V163, P165, G167, D168, E169, V170, E203, K206, T209, L210, N211 of human CD73 (Uniprot accession no. P21589) which is specifically bound by the inventive anti-CD73 antibody.

According to a preferred embodiment, the inventive anti-CD73 antibody as disclosed above comprises a light chain which comprises an amino acid sequence according to one of SEQ ID NO: 102, SEQ ID NO: 110, SEQ ID NO: 112, SEQ ID NO: 114, SEQ ID NO: 116, SEQ ID NO: 118, SEQ ID NO: 120 and binds e.g. to at least two, three, four, five, six, seven, eight, nine, ten, or all of the amino acid residues as disclosed above, e.g. F137, P138, 1139, A151, S152, S155, G156, L157, T158, L159, P160, Y161, K162, E203 and K206, which contribute to and are part of the conformational epitope on CD73 formed by amino acids F137, P138, 1139, A151, S152, G156, L157, Y158, L159, P160, Y161, K162, V163, P165, G167, D168, E169, V170, E203, K206, T209, L210, N211 (amino acid numbering corresponds to Uniprot accession no. P21589). Binding of the inventive light chain as disclosed above to the conformational epitope on CD73 which comprises amino acid residues F137, P138, 1139, A151, S152, G156, L157, Y158, L159, P160, Y161, K162, V163, P165, G167, D168, E169, V170, E203, K206, T209, L210, N211 contributes to the specific binding of the inventive anti-CD73 antibody to CD73 thereby inhibiting its function.

According to a preferred embodiment, the inventive anti-CD73 antibody as disclosed above comprises a heavy chain which comprises an amino acid sequence according to one SEQ ID NO: 101, SEQ ID NO: 111, SEQ ID NO: 113, SEQ ID NO: 115, SEQ ID NO: 117, SEQ ID NO: 119 and binds to at least two, three, four, five, six, seven, eight, nine, ten, or all of the amino acids L159, P160, Y161, K162, V163, P165, G167, D168, E169, V170, T209, L210 and N211 on CD73 which contribute to and are part of the conformational epitope formed by amino acids F137, P138, 1139, A151, S152, G156, L157, Y158, L159, P160, Y161, K162, V163, P165, G167, D168, E169, V170, E203, K206, T209, L210, N211 of human CD73 (Uniprot accession no. P21589). Binding of the inventive heavy chain as disclosed above to the conformational epitope on CD73 formed by amino acids F137, P138, 1139, A151, S152, G156, L157, Y158, L159, P160, Y161, K162, V163, P165, G167, D168, E169, V170, E203, K206, T209, L210, N211 contributes to the specific binding of the inventive anti-CD73 antibody to CD73 thereby inhibiting CD73 function.

Figure 4:
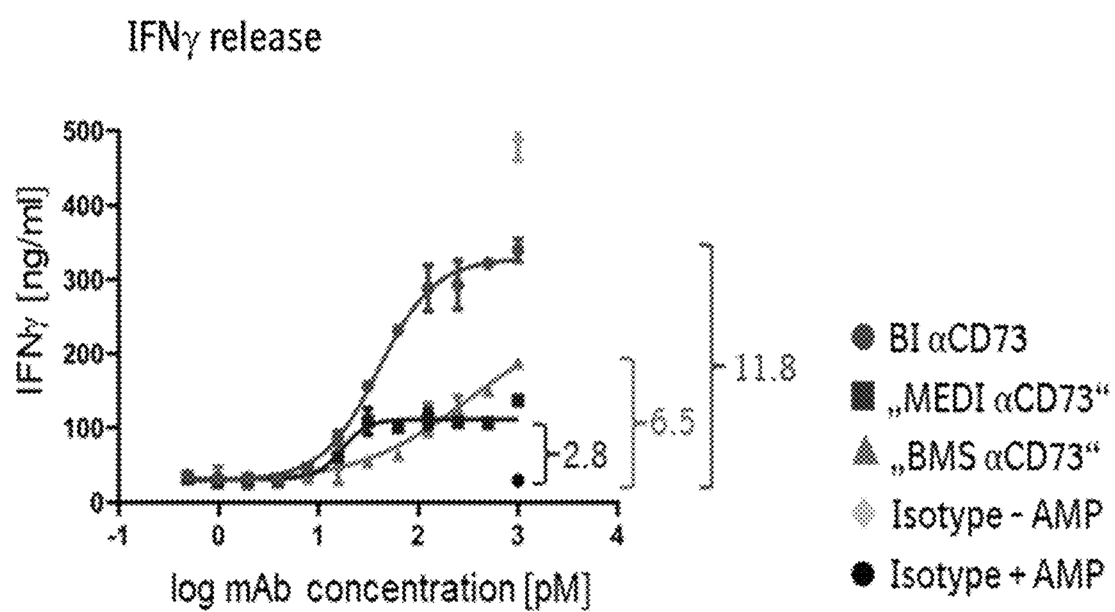
FIG. 4: IFNγ release in human T cell assay

According to one embodiment, binding of the inventive anti-CD73 as disclosed above to the conformational epitope formed by amino acids F137, P138, 1139, A151, S152, G156, L157, Y158, L159, P160, Y161, K162, V163, P165, G167, D168, E169, V170, E203, K206, T209, L210, N211 of human CD73 (Uniprot accession no. P21589) induces IFNγ release in T cells (see e.g. FIG. 4). For example, binding of the inventive anti-CD73 antibody as disclosed above which comprises heavy chain CDRs 1-3 comprising amino acid sequences according to SEQ ID NO: 55 (HCDR1), 56 (HCDR2) and SEQ ID NO: 57(HCDR3) and light chain CDRs 1-3 comprising amino acid sequences according to SEQ ID NO: 58 (LCDR1), SEQ ID NO.:59 (LCDR2) and SEQ ID NO: 60 (LCDR3), or a $V_H$ comprising the amino acid sequence according to SEQ ID NO 91 and a $V_L$ comprising the amino acid sequence according to SEQ ID NO 92, or e.g. which comprises a heavy chain comprising the amino acid sequence according to SEQ ID NO: 115 and a light chain comprising the amino acid sequence according to SEQ ID No: 116 induces IFNγ release in T cells (e.g. see: FIG. 4), e.g. IFNγ release induced by the inventive antibody is at least 5-, 6-, 7-, 8-9, 10-, 11-fold compared to isotype control+AMP in vitro, whereby e.g. IFNγ levels may be determined as disclosed in Example 6. Accordingly, the antibody of the invention is able to restore IFNγ release by T cells to a level substantially the same e.g. 75%, 80%, 85%, 90%, 95%, of the control level (stimulated T cells treated with isotype control without AMP addition).

According to a preferred embodiment the inventive anti-CD73 antibody as disclosed above comprises a heavy chain according to SEQ ID NO: 101 and a light chain according to SEQ ID NO: 102 and inhibits CD73 function by binding to at least two, three, four, five, six, seven, eight, nine, ten or all amino acid residues of a conformational epitope comprised of amino acid residues F137, P138, 1139, A151, S152, G156, L157, Y158, L159, P160, Y161, K162, V163, P165, G167, D168, E169, V170, E203, K206, T209, L210, N211 on CD73.

According to a preferred embodiment the inventive anti-CD73 antibody as disclosed above comprises a heavy chain according to SEQ ID NO: 109 and a light chain according to SEQ ID NO: 110 and inhibits the function of CD73 by binding to at least two, three, four, five, six, seven, eight, nine, ten or all amino acid residues of a conformational epitope comprised of amino acid residues F137, P138,1139, A151, S152, G156, L157, Y158, L159, P160, Y161, K162, V163, P165, G167, D168, E169, V170, E203, K206, T209, L210, N211 on CD73.

According to a preferred embodiment the inventive anti-CD73 antibody as disclosed above comprises a heavy chain according to SEQ ID NO: 111 and a light chain according to SEQ ID NO: 112 and inhibits the function of CD73 by binding to at least two, three, four, five, six, seven, eight, nine, ten or all amino acid residues of a conformational epitope comprised of amino acid residues F137, P138,1139, A151, S152, G156, L157, Y158, L159, P160, Y161, K162, V163, P165, G167, D168, E169, V170, E203, K206, T209, L210, N211 on CD73.

According to a preferred embodiment the inventive anti-CD73 antibody as disclosed above comprises a heavy chain according to SEQ ID NO: 113 and a light chain according to SEQ ID NO: 114 and inhibits the function of CD73 by binding to at least two, three, four, five, six, seven, eight, nine, ten or all amino acid residues of a conformational epitope comprised of amino acid residues F137, P138, 1139, A151, S152, G156, L157, Y158, L159, P160, Y161, K162, V163, P165, G167, D168, E169, V170, E203, K206, T209, L210, N211 on CD73.

According to a preferred embodiment the inventive anti-CD73 antibody as disclosed above comprises a heavy chain according to SEQ ID NO: 115 and a light chain according to SEQ ID NO: 116 and inhibits the function of CD73 by binding to at least two, three, four, five, six, seven, eight, nine, ten or all amino acid residues of a conformational epitope comprised of amino acid residues F137, P138,1139, A151, S152, G156, L157, Y158, L159, P160, Y161, K162, V163, P165, G167, D168, E169, V170, E203, K206, T209, L210, N211 on CD73.

According to a preferred embodiment the inventive anti-CD73 antibody as disclosed above comprises a heavy chain according to SEQ ID NO: 117 and a light chain according to SEQ ID NO: 118 and inhibits the function of CD73 by binding to at least two, three, four, five, six, seven, eight, nine, ten or all amino acid residues of a conformational epitope comprised of amino acid residues F137, P138,1139, A151, S152, G156, L157, Y158, L159, P160, Y161, K162, V163, P165, G167, D168, E169, V170, E203, K206, T209, L210, N211 on CD73.

According to a preferred embodiment the inventive anti-CD73 antibody as disclosed above comprises a heavy chain according to SEQ ID NO: 119 and a light chain according to SEQ ID NO: 120 and inhibits the function of CD73 by binding to at least two, three, four, five, six, seven, eight, nine, ten or all amino acid residues of a conformational epitope comprised of amino acid residues F137, P138,1139, A151, S152, G156, L157, Y158, L159, P160, Y161, K162, V163, P165, G167, D168, E169, V170, E203, K206, T209, L210, N211 on CD73.

According to a preferred embodiment the present invention provides anti-CD73 antibodies that bind to the conformational epitope formed by amino acids F137, P138, 1139, A151, S152, G156, L157, Y158, L159, P160, Y161, K162, V163, P165, G167, D168, E169, V170, E203, K206, T209, L210, N211 of human CD73 and which cross-compete with the binding to the conformational epitope of the inventive anti-CD73 antibody disclosed above, e.g. with the binding of an anti-CD73 antibody which comprises a heavy chain according to SEQ ID NO: 115 and a light chain according to SEQ ID NO: 116. Cross-competition of antibody binding may e.g. be assessed by suitable methods known in the art such as those described in Anal Biochem. 2009 Mar. 15; 386(2):172-80.

According to a preferred embodiment amino acid residues T28, T31, Y32, W33, Y52, L55, D57, L99, L100, D101, Y102 of the heavy chain variable region of the inventive anti-CD73 antibody and amino acid residues R30, S31, Y32, W49, Y50, T51, S52, R53, S65, G66, S67, E92 of the light chain variable region of the inventive anti-CD73 antibody contact and/or specifically bind to the conformational epitope on CD73 comprising amino acid residues F137, P138, 1139, A151, S152, G156, L157, Y158, L159, P160, Y161, K162, V163, P165, G167, D168, E169, V170, E203, K206, T209, L210, N211, wherein the inventive anti-CD73 antibody comprises amino acid sequences according to SEQ ID NO: 115 and SEQ ID NO: 116, and wherein the inventive anti-CD73 antibody inhibits CD73 enzymatic activity with an 1090 of less than 5 nM, 4 nM, 3 nM, 2 nM, 1.5 nM, 1 nM, 0.5 nM or lower, preferably with an 1090 of less than 0.5 nM. For example, the inventive antibody as disclosed above may inhibit the formation of adenosine by at least 60%, by at least 70%, preferably by more than 75%. Inhibition of adenosine formation in vitro by the inventive antibody as disclosed above may e.g. be assessed in cell culture supernatants as described in Example 8. Inhibition of adenosine formation by the inventive antibody in vivo may e.g. be assessed in blood samples, or in samples taken from tumor microenvironment by methods as described in Lofgren L, Pehrsson S, Hagglund G, Tjellstrom H, Nylander S (2018) Accurate measurement of endogenous adenosine in human blood. PLoS ONE 13(10): e0205707. https://doi.org/10.1371/journal.pone.0205707.

For example, in a preferred embodiment, by binding to the conformational epitope which comprises amino acid residues F137, P138, 1139, A151, S152, G156, L157, Y158, L159, P160, Y161, K162, V163, P165, G167, D168, E169, V170, E203, K206, T209, L210, N211 the inventive anti-CD73 antibody as disclosed above inhibits the enzymatic activity of CD73 by inhibiting the adoption of “open” and “closed” conformations of CD73 which are required for the enzymatic activity of CD73 to hydrolyze AMP.

According to a preferred embodiment, the inventive anti-CD73 antibody as disclosed above inhibits CD73 enzymatic activity by binding to a conformational epitope on CD73 which comprises amino acid residues F137, P138, 1139, A151, S152, G156, L157, Y158, L159, P160, Y161, K162, V163, P165, G167, D168, E169, V170, E203, K206, T209, L210, N211 thereby reducing cell surface levels of CD73 (see: Example 4).

Preferably, said anti-CD73 antibody is humanized. Such antibodies may be generated using methods known in the art, e.g. by using the epitope sequence for immunization, or recombinantly expressed and purified CD73 protein.

The epitope of an antibody can be determined using methods known in the art, e.g. by hydrogen-deuterium exchange mass spectrometry (HDX-MS), NMR, site-directed mutagenesis (e.g. alanine-scanning) or X-ray crystallography of the antibody-antigen complex.

Hydrogen-deuterium exchange mass spectrometry (HDX-MS) determines protein conformation and conformational dynamics in solution by monitoring the rate and extent of deuterium exchange of protein backbone amide hydrogen atoms. The exchange level of HDX depends on protein solvent accessibility and hydrogen bonds, and the mass increase of the protein upon HDX can be precisely measured by MS. When this technique is paired with enzymatic digestion, structure features at the peptide level can be resolved, enabling differentiation of surface exposed peptides from those folded inside. In epitope mapping experiments, the deuterium labeling and subsequent quenching experiments are performed in parallel for antigen and antigen/mAb complex, followed by online pepsin digestion, peptide separation, and MS analysis.

Binding competition for an epitope can be determined using any of the methods known in the art. For example, standard ELISA assays or competitive ELISA assays can be used in which a recombinant human CD73 protein is immobilized on the plate, various concentrations of unlabeled first antibody are added, the plate is washed, labeled second antibody is added, washed, and the amount of bound label is measured. If the increasing concentration of the unlabeled (first) antibody (also referred to as the "blocking antibody") inhibits the binding of the labeled (second) antibody, the first antibody is said to inhibit the binding of the second antibody to the target on the plate, or is said to compete with the binding of the second antibody. Additionally or alternatively, surface plasmon resonance (SPR) analysis can be used to assess the ability of the antibodies to compete. The ability of a test antibody to inhibit the binding of an anti-CD73 antibody described herein (e.g. antibodies A1, A2, A3, A4, B1, B2, C1, C2, C3, C4, C5, or C6, Table 9) to CD73 demonstrates that the test antibody can compete with the antibody for binding to CD73.

The anti-CD73 antibodies described above, i.e. according to the first aspect of the invention, are also collectively referred to herein as "antibodies of the invention", "CD73 antibodies of the invention", "anti-CD73 antibodies of the invention", "antibodies described herein" or similar.

A further aspect of the present invention provides isolated nucleic acid molecules encoding the heavy chain variable region and/or the light chain variable region of an anti-CD73 antibody molecule of any of the first aspect of the invention. The nucleic acid molecules of the invention include, but are not limited to, the DNA molecules encoding the anti-CD73 antibody amino acid sequences provided herein. Also, the present invention also relates to nucleic acid molecules that hybridize to the DNA molecules encoding the polypeptide sequences shown in the sequence listing under high stringency binding and washing conditions, as defined in WO 2007/042309. Preferred molecules (from an mRNA perspective) are those that have at least 75% or 80% (preferably at least 85%, more preferably at least 90% and most preferably at least 95%) homology or sequence identity with one of the DNA molecules described herein. By way of example, in view of expressing the antibodies in eukaryotic cells, the DNA sequences shown in the sequence listing have been designed to match codon usage in eukaryotic cells. If it is desired to express the antibodies in *E. coli*, these sequences can be changed to match *E. coli* codon usage. Variants of DNA molecules of the invention can be constructed in several different ways, as described e.g. in WO 2007/042309.

In a further aspect, the present invention provides an expression vector containing a nucleic acid molecule comprising the nucleotide sequence encoding the heavy chain variable region and/or the light chain variable region of an anti-CD73 antibody molecule of any of the first aspect of the invention.

Preferably the nucleic acid molecule comprises a nucleotide sequence encoding the heavy chain variable region of any of SEQ ID NOs: 81, 83, 85, 87, 89, 91, 93, and 95. Preferably the nucleic acid molecule comprises a nucleotide sequence encoding the light chain variable region of any of SEQ ID NOs SEQ ID NOs: 82, 84, 86, 88, 90, 92, 94 or 96.

Preferably the expression vector comprises, in addition, a nucleic acid molecule, preferably a DNA molecule, encoding the constant domains of a heavy chain and/or the constant domain of a light chain, respectively, linked to the nucleic acid molecule, preferably the DNA molecule, encoding the heavy chain variable domain and/or the light chain variable domain, respectively.

In a specifically preferred embodiment, two expression vectors may be used, one of them for expression of the heavy chain, the other one for expression of the light chain, which two expression vectors may then both be transfected into a host cell for recombinant protein expression.

Preferably, the expression vector will be a vector comprising said nucleic acid molecule or molecules, operably linked to at least one regulatory sequence, wherein such regulatory sequence may be a promoter, enhancer, or terminator sequence, and most preferably a heterologous promotor, enhancer, or terminator sequence.

The nucleic acids of the invention may be prepared or obtained in a manner known per se (e.g. by automated DNA synthesis and/or recombinant DNA technology), based on the information on the amino acid sequences for the antibodies of the invention given herein.

In another aspect, the invention relates to a host cell having an expression vector as described above, such as an expression vector encoding a heavy chain of an anti-CD73 antibody molecule of the invention and an expression vector encoding a light chain of an anti-CD73 antibody molecule of the invention. In some embodiments, the host cell comprises a vector encoding both the light chain and the heavy chain of an anti-CD73 antibody molecule of the invention, in particular if the antibody is a single-chain antibody, such as a scFv.

According to a particularly preferred embodiment, said host cells are eukaryotic cells such as mammalian cells, in particular human cells (in vitro). In another embodiment, such host cells are bacterial cells. Other useful cells are yeast cells or other fungal cells.

Mammalian cell lines available as hosts for expression are well known in the art and include, inter alia, Chinese hamster ovary (CHO, CHO-DG44) cells, NSO, SP2/0 cells, HeLa cells, baby hamster kidney (BHK) cells, monkey kidney cells (COS), human carcinoma cells (e. g., Hep G2), A549 cells, 3T3 cells or the derivatives/progenies of any such cell line. Other mammalian cells, including but not limited to human, mice, rat, monkey and rodent cells lines, or other eukaryotic cells, including but not limited to yeast, insect and plant cells, or prokaryotic cells such as bacteria may be used. The antibodies of the invention are produced by culturing the host cells for a period of time sufficient to allow for expression of the antibody in the host cells. However, amphibian cells, insect cells, plant cells, and any other cells used in the art for the expression of heterologous proteins can be used as well.

In another aspect, the invention provides a method of manufacturing an anti-CD73 antibody molecule of the invention, comprising the steps of:

culturing a host cell as described above under conditions that allow formation of an anti-CD73 antibody molecule of the invention; and, recovering said antibody molecule.

In one embodiment, the method of manufacturing additionally comprises the step of further purifying said antibody, as described further below.

In one embodiment, the method of manufacturing additionally comprises the step of further modifying said antibody as further described herein.

In one embodiment, the method of manufacturing additionally comprises the step of formulating said antibody molecule into a pharmaceutical composition as further described herein.

Any method that is known in the art for producing an antibody may be used, e.g. as described herein.

In another aspect, the invention provides an anti-CD73 antibody as described above for use in medicine. Specific medical uses of the antibodies of the invention are described in further detail herein below.

In another aspect, a pharmaceutical composition is provided, comprising an anti-CD73 antibody of the invention and a pharmaceutically acceptable carrier. Suitable carriers are known in the art and further described herein below. This composition may also comprise an additional therapeutic agent as described herein below in more detail, such as, but not limited to, a PD-1 antagonist.

Pharmaceutical Compositions Including Anti-CD73 Antibodies and Other Therapeutic Agents, Such as a PD-1 Antagonist; Kit of Parts, Methods and Uses PD-1 plays an important role in regulating T-cell activity and hence immune system activity.

It has been shown in a range of different cancer settings that antagonistic anti-PD-1 antibodies molecules can increase T-cell activity, thereby activating the immune system to attack tumors and so treat cancer.

It is known that monoclonal antibodies that block PD-1 receptors have been associated with durable clinical responses against a variety of cancer types and hold great potential as novel cancer therapeutics. It has also been shown that targeting CD73 enhances the antitumor activity of anti-PD-1 antibodies.

Against this background, the inventors sought to investigate the combination of the anti-CD73 antibodies of the invention with PD-1 antibodies.

Using a dendritic cell/T cell co-culture assay (further outlined in Example 7) the inventors examined functional characteristics of representative anti-CD73 antibody molecules of the present invention in combination with anti-PD-1 molecules. As can be seen in Example 7 and FIG. 1, the effect of an anti-PD1 antibody is suppressed by AMP, which shows clearly that the PD1 response is dependent on AMP. The combination of anti-CD73 antibody molecule of the present invention with a PD-1 antagonist, such as an anti-PD-1 antibody, is capable of reverting the AMP-dependent suppression and restoring IFNγ levels.

Thus, a further aspect of the invention provides a pharmaceutical composition comprising an anti-CD73 antibody of the invention, a PD-1 antagonist, and a pharmaceutically acceptable carrier. Suitable carriers are known in the art and further described herein below.

Suitable PD-1 antagonists are described herein below.

In some embodiments, the PD-1 antagonist is an anti-PD-1 antibody. In some embodiments, the PD-1 antagonist is an anti-PDL-1 antibody. In some embodiments, this anti-PD-1 antibody is selected from the group consisting of PDR-001, pembrolizumab, nivolumab and pidilizumab. Preferably the anti-PD-1 antibody molecule is selected from PD1-1, PD1-2, PD1-3, PD1-4, and PD1-5 as described herein.

In some embodiments, the anti-PDL-1 antibody is selected from atezolizumab, avelumab or durvalumab.

Instead of an anti-CD73 antibody of the invention, another anti-CD73 antibody, such as MED19447, BMS986179, CPX-006, CPX-0016, or an antibody as described in WO08007648, WO2016075099, WO2016081748, WO2016055609, WO2016131950, WO17064043, WO2017100670, WO17152085 or WO2018013611 can also be used.

A further aspect of the invention provides a kit of parts comprising an anti-CD73 antibody molecule of the invention and a PD-1 antagonist. The kit may further comprise instructions for use.

Suitable PD-1 antagonists are described herein below.

In some embodiments, the PD-1 antagonist is an anti-PD-1 antibody. In some embodiments, the PD-1 antagonist is an anti-PDL-1 antibody. In some embodiments, this anti-PD-1 antibody is selected from the group consisting of PDR-001, pembrolizumab, nivolumab and pidilizumab. Preferably the anti-PD-1 antibody molecule is selected from PD1-1, PD1-2, PD1-3, PD1-4, and PD1-5 as described herein.

In some embodiments, the anti-PDL-1 antibody is selected from atezolizumab, avelumab or durvalumab.

Instead of an anti-CD73 antibody of the invention, another anti-CD73 antibody, such as MED19447, BMS986179, CPX-006, CPX-0016, or an antibody as described in WO08007648, WO2016075099, WO2016081748, WO2016055609, WO2016131950, WO17064043, WO2017100670, WO17152085 or WO2018013611 can also be used.

It will be clear to the skilled person that based on the above, there are also disclosed herewith pharmaceutical compositions for the treatment of a disease (as specified in more detail below) using the antibody molecules of the invention set out above, e.g. an anti-CD73 antibody of the invention and a PD-1 antagonist, as well as methods of treating a disease (as specified in more detail below) making use of such pharmaceutical compositions or antibody molecules of the invention.

For the avoidance of doubt, all of the embodiments relating to pharmaceutical compositions, kits, treatment methods, medical uses, methods of administration and dosages as described herein are contemplated for any of the anti-CD73 antibodies described herein, either alone or in combination with further therapeutic agents, such as a PD-1 antagonist. Any of the PD-1 antagonists as described herein may be used (including inhibitors of PD-1 and PDL-1) such as pembrolizumab, nivolumab, pidilizumab, atezolizumab, avelumab, durvalumab, PD1-1, PD1-2, PD1-3, PD1-4, or PD1-5 as described herein.

When the anti-CD73 antibody molecule of the invention and the anti-PD-1 antibody molecule of the invention are to be administered simultaneously via the same route of administration, they may be administered as different pharmaceutical formulations or compositions or as part of a combined pharmaceutical formulation or composition. Also, when the anti-CD73 antibody molecule of the invention and the anti-PD-1 antibody molecule of the invention are to be used as part of a combined treatment regimen, each of the antibodies may be administered in the same amount and according to the same regimen as used when one of the antibodies is used on its own, and such combined use may or may not lead to a synergistic effect. However, when the combined use of the antibodies leads to a synergistic effect, it may also be possible to reduce the amount of one or both of the antibodies, while still achieving the desired therapeutic action. This may for example be useful for avoiding, limiting or reducing any unwanted side-effects that are associated with the use of one or both of the antibodies when they are used in their usual amounts, while still obtaining the desired pharmacological or therapeutic effect.

Further to the anti-CD73 antibody and the PD-1 antagonist, the composition and kit described above may also comprise an additional therapeutic agent as described herein below in more detail.

Pharmaceutical Compositions, Methods of Administration, Dosages

The invention further relates to pharmaceutical compositions for the treatment of a disease (as specified in more detail below), wherein such compositions comprise at least one anti-CD73 antibody as provided herein. The invention further encompasses methods of treating a disease (as specified in more detail below) using at least one anti-CD73 antibody or pharmaceutical composition as set out before, and further encompasses the preparation of a medicament for the treatment of such disease by using such anti-CD73 antibody molecule(s) of the invention or pharmaceutical composition.

Such compositions are contemplated for any of the anti-CD73 antibodies described herein, either alone or in combination with further therapeutic agents, such as a PD-1 antagonist, e.g. pembrolizumab, nivolumab, pidilizumab, atezolizumab, avelumab, durvalumab, PD1-1, PD1-2, PD1-3, PD1-4, or PD1-5.

The anti-CD73 antibody and/or the composition comprising the same can be administered to a patient in need thereof in any suitable manner, depending on the specific pharmaceutical formulation or composition to be used. Thus, the anti-CD73 antibody and/or the composition comprising the same can for example be administered intravenously (i.v.), subcutaneously (s.c.), intramuscularly (i.m.), intraperitoneally (i.p.), transdermally, orally, sublingually (e.g. in the form of a sublingual tablet, spray or drop placed under the tongue and adsorbed through the mucus membranes into the capillary network under the tongue), (intra-)nasally (e.g. in the form of a nasal spray and/or as an aerosol), topically, by means of a suppository, by inhalation, or any other suitable manner in an effective amount or dose.

The anti-CD73 antibody and/or the composition comprising the same are administered according to a regimen of treatment that is suitable for treating and/or alleviating the disease, disorder or condition to be treated or alleviated. The clinician will generally be able to determine a suitable treatment regimen, depending on factors such as the disease, disorder or condition to be treated or alleviated, the severity of the disease, the severity of the symptoms thereof, the specific antibody molecules of the invention to be used, the specific route of administration and pharmaceutical formulation or composition to be used, the age, gender, weight, diet, general condition of the patient, and similar factors well known to the clinician. Generally, the treatment regimen will comprise the administration of one or more antibody molecules of the invention, or of one or more compositions comprising the same, in therapeutically effective amounts or doses.

Generally, for the treatment and/or alleviation of the diseases, disorders and conditions mentioned herein and depending on the specific disease, disorder or condition to be treated, the potency of the specific antibody molecule of the invention to be used, the specific route of administration and the specific pharmaceutical formulation or composition used, the antibody molecules of the invention will generally be administered in an amount between 0.05 and 50.0 mg per kilogram of body weight and dose, preferably between 5.0 and 20.0 mg/kg/dose, and more preferably between 10 and 15 mg/kg/dose, either continuously (e.g. by infusion) or more preferably as single doses (such as e.g. twice a week, weekly, or monthly doses; cf. below), but can significantly vary, especially, depending on the before-mentioned parameters. Thus, in some cases it may be sufficient to use less than the minimum dose given above, whereas in other cases the upper limit may have to be exceeded. When administering large amounts it may be advisable to divide them up into a number of smaller doses spread over the day.

Depending on the specific antibody molecule of the invention and its specific pharmacokinetic and other properties, it may be administered daily, every second, third, fourth, fifth or sixth day, weekly, monthly, and the like. An administration regimen could include long-term, weekly treatment. By "long-term" is meant at least two weeks and preferably months, or years of duration.

The efficacy of the antibody molecules of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

Formulations

For pharmaceutical use, the antibody molecules of the invention may be formulated as a pharmaceutical preparation comprising (i) at least one anti-CD73 antibody of the invention and (ii) at least one pharmaceutically acceptable carrier, diluent, excipient, adjuvant, and/or stabilizer, and (iii) optionally one or more further pharmacologically active polypeptides and/or compounds, such as a PD-1 antagonist. By "pharmaceutically acceptable" is meant that the respective material does not show any biological or otherwise undesirable effects when administered to an individual and does not interact in a deleterious manner with any of the other components of the pharmaceutical composition (such as e.g. the pharmaceutically active ingredient) in which it is contained. Specific examples can be found in standard handbooks, such as e.g. Remington's Pharmaceutical Sciences, $18^{th}$ Ed., Mack Publishing Company, USA (1990). For example, the antibodies of the invention may be formulated and administered in any manner known per se for conventional antibodies and antibody fragments and other pharmaceutically active proteins. Thus, according to a further embodiment, the invention relates to a pharmaceutical composition or preparation that contains at least one CD73 antibody of the invention, and at least one pharmaceutically acceptable carrier, diluent, excipient, adjuvant and/or stabilizer, and optionally one or more further pharmacologically active substances, such as a PD-1 antagonist, as further described herein.

Pharmaceutical preparations for parenteral administration, such as intravenous, intramuscular, subcutaneous injection or intravenous infusion may for example be sterile solutions, suspensions, dispersions, emulsions, or powders which comprise the active ingredient and which are suitable, optionally after a further dissolution or dilution step, for infusion or injection. Suitable carriers or diluents for such preparations for example include, without limitation, sterile water and pharmaceutically acceptable aqueous buffers and solutions such as physiological phosphate-buffered saline, Ringer's solutions, dextrose solution, and Hank's solution; water oils; glycerol; ethanol; glycols such as propylene glycol, as well as mineral oils, animal oils and vegetable oils, for example peanut oil, soybean oil, as well as suitable mixtures thereof.

Solutions of the antibody molecules of the invention may also contain a preservative to prevent the growth of microorganisms, such as antibacterial and antifungal agents, for example, p-hydroxybenzoates, parabens, chlorobutanol, phenol, sorbic acid, thiomersal, (alkali metal salts of) ethylenediamine tetraacetic acid, and the like. In many cases, it will be preferable to include isotonic agents, for example, sugars, buffers or sodium chloride. Optionally, emulsifiers and/or dispersants may be used. The proper fluidity can be maintained, for example, by the formation of liposomes, by the maintenance of the required particle size in the case of dispersions or by the use of surfactants. Other agents delaying absorption, for example, aluminum monostearate and gelatin, may also be added. The solutions may be filled into injection vials, ampoules, infusion bottles, and the like.

In all cases, the ultimate dosage form must be sterile, fluid and stable under the conditions of manufacture and storage. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Usually, aqueous solutions or suspensions will be preferred. Generally, suitable formulations for therapeutic proteins such as the antibodies of the invention are buffered protein solutions, such as solutions including the protein in a suitable concentration (such as from 0.001 to 400 mg/ml, preferably from 0.005 to 200 mg/ml, more preferably 0.01 to 200 mg/ml, more preferably 1.0-100 mg/ml, such as 1.0 mg/ml, 50 mg/ml or 100 mg/ml and an aqueous buffer such as:

phosphate buffered saline, pH 7.4,
other phosphate buffers, pH 6.2 to 8.2,
acetate buffers, pH 3.2 to 7.5, preferably pH 4.8 to 5.5
histidine buffers, pH 5.0 to 7.0,
succinate buffers, pH 3.2 to 6.6, and
citrate buffers, pH 2.1 to 6.2, and, optionally, salts (e.g. NaCl) and/or sugars (such as e.g. sucrose and trehalose) and/or other polyalcohols (such as e.g. mannitol and glycerol) for providing isotonicity of the solution, and/or surfactants.

Preferred buffered protein solutions are solutions including about 50 mg/ml of the antibody of the invention, alone or in combination with a PD-1 antagonist, dissolved in 25 mM acetate buffer, pH 5.5, optionally comprising 0.67 mM methionine, adjusted to isotonicity by adding 240 mM trehalose. Other surfactants, e.g. 0.04% Tween-20, Tween-80 or Polysorbate 80, may also be included in such solutions. Formulations for subcutaneous application may include significantly higher concentrations of the antibody of the invention, such as up to 100 mg/ml or even above 100 mg/ml. However, it will be clear to the person skilled in the art that the ingredients and the amounts thereof as given above do only represent one, preferred option. Alternatives and variations thereof will be immediately apparent to the skilled person, or can easily be conceived starting from the above disclosure.

According to a further aspect of the invention, an antibody molecule of the invention may be used in combination with a device useful for the administration of the antibody, such as a syringe, injector pen, micropump, or other device.

Therapeutic Uses/Methods of Treatment

A further aspect of the invention provides a method of treating cancer comprising administering to a patient in need thereof a therapeutically effective amount of the anti-CD73 antibody molecule of the invention. In a preferred embodiment the method further comprises administering to such patient a PD-1 antagonist, such as an anti-PD-1 antibody or an anti-PDL-1 antibody. Preferably said anti-PD-1 antibody is selected from the group consisting of pembrolizumab, nivolumab, pidilizumab, PD1-1, PD1-2, PD1-3, PD1-4, and PD1-5 as described herein. Preferably said anti-PDL-1 antibody is selected from the group consisting of atezolizumab, avelumab and durvalumab.

In some embodiments, the cancer is kidney cancer, gastrointestinal cancer or lung cancer. In some embodiments, said gastrointestinal cancer is colon carcinoma, gastric cancer or hepatocellular carcinoma. In some embodiments, said kidney cancer is renal cancer, preferably clear cell carcinoma. In a preferred embodiment of the invention the cancer is lung cancer, preferably non-small cell lung cancer (NSCLC). In some embodiments, said colon carcinoma is CRC.

In some embodiments, the anti-CD73 antibody molecule of the invention, optionally together with a PD-1 antagonist as described above, is administered in combination with one or more further therapeutic agents and/or procedures, which agents and procedures are described herein below in further detail. Non-limiting examples are therapeutic agents or procedures selected from chemotherapy, a targeted anti-cancer therapy, an oncolytic drug, a cytotoxic agent, an immune-based therapy, a cytokine, surgical procedure, a radiation procedure, a vaccine, or a cellular immunotherapy.

In some embodiments, the further therapeutic agent is an A2AR antagonist, CD39 antagonist, LAG-3 antagonist, CTLA-4 antagonist, EGFR antagonist, or HER2 antagonist.

A further aspect of the invention provides an anti-CD73 antibody molecule of the invention for use in a method of treating cancer. In a preferred embodiment the aspect further comprises the additional use of a PD-1 antagonist, such as an anti-PD-1 antibody or an anti-PDL-1 antibody. Preferably said anti-PD-1 antibody is selected from the group consisting of pembrolizumab, nivolumab, pidilizumab, PD1-1, PD1-2, PD1-3, PD1-4, and PD1-5 as described herein. Preferably said anti-PDL-1 antibody is selected from the group consisting of atezolizumab, avelumab and durvalumab.

In some embodiments, the cancer is kidney cancer, gastrointestinal cancer or lung cancer. In some embodiments, said gastrointestinal cancer is colon carcinoma, gastric cancer or hepatocellular carcinoma. In some embodiments, said kidney cancer is renal cancer, preferably clear cell carcinoma. In a preferred embodiment of the invention the cancer is lung cancer, preferably non-small cell lung cancer (NSCLC). In some embodiments, said colon carcinoma is CRC.

In some embodiments, the anti-CD73 antibody molecule of the invention, optionally together with a PD-1 antagonist as described above, is administered in combination with one or more further therapeutic agents and/or procedures, which agents and procedures are described herein below in further detail. Non-limiting examples are therapeutic agents or procedures selected from chemotherapy, a targeted anti-cancer therapy, an oncolytic drug, a cytotoxic agent, an immune-based therapy, a cytokine, surgical procedure, a radiation procedure, a vaccine, or a cellular immunotherapy.

As known in the art, "targeted anti-cancer therapy" refers to systemic administration of drugs with particular mechanisms that specifically act on well-defined targets or biologic pathways that, when activated or inactivated, may cause regression or destruction of the malignant process, meanwhile with minimized adverse effects on healthy tissues (Li et al, Target Oncol. 2012; 7(1):69-85). An "immune-based therapy", or "immunotherapy" is the treatment of disease by inducing, enhancing, or suppressing an immune response. In the context of cancer, an immune-based therapy usually refers to a therapy inducing and/or enhancing an immune response, e.g. using immunotherapeutic agents as described herein below.

In some embodiments, the further therapeutic agent is an A2AR antagonist, CD39 antagonist, LAG-3 antagonist, CTLA-4 antagonist, EGFR antagonist, or HER2 antagonist.

A PD-1 antagonist within the meaning of this invention and all of its embodiments is a compound that inhibits the interaction of PD-1 with its receptor(s). PD-1 antagonists are well-known in the art, e.g. reviewed by Li et al., Int. J. Mol. Sci. 2016, 17, 1151 (incorporated herein by reference). The PD-1 antagonist may be an inhibitor of PD-1, or an inhibitor of PDL-1, such as an anti-PD-1 antibody or an anti-PDL-1 antibody. In some embodiments, the PD-1 antagonist is an anti-PD-1 antibody. In some embodiments, the PD-1 antagonist is an anti-PDL-1 antibody.

Any PD-1 antagonist, especially antibodies, such as those disclosed by Li et al. as well as the further antibodies disclosed herein below, can be used according to the invention. Preferably, the PD-1 antagonist of this invention and all its embodiments is selected from the group consisting of the following antibodies:

pembrolizumab (anti-PD-1 antibody);
nivolumab (anti-PD-1 antibody);
pidilizumab (anti-PD-1 antibody);
PDR-001 (anti-PD-1 antibody);
atezolizumab (anti-PDL-1 antibody);
avelumab (anti-PDL-1 antibody);
durvalumab (anti-PDL-1 antibody)
PD1-1, PD1-2, PD1-3, PD1-4 and PD1-5 as described herein (anti-PD1-antibodies).

Pembrolizumab (formerly also known as lambrolizumab; trade name Keytruda; also known as MK-3475) disclosed e.g. in Hamid, O. et al. (2013) New England Journal of Medicine 369(2):134-44, is a humanized IgG4 monoclonal antibody that binds to PD-1; it contains a mutation at C228P designed to prevent Fc-mediated cytotoxicity. Pembrolizumab is e.g. disclosed in U.S. Pat. No. 8,354,509 and WO2009/114335. It is approved by the FDA for the treatment of patients suffering from unresectable or metastatic melanoma and patients with metastatic NSCLC.

Nivolumab (CAS Registry Number: 946414-94-4; BMS-936558 or MDX1106b) is a fully human IgG4 monoclonal antibody which specifically blocks PD-1, lacking detectable antibody-dependent cellular toxicity (ADCC). Nivolumab is e.g. disclosed in U.S. Pat. No. 8,008,449 and WO2006/121168. It has been approved by the FDA for the treatment of patients suffering from unresectable or metastatic melanoma, metastatic NSCLC and advanced renal cell carcinoma.

Pidilizumab (CT-011; Cure Tech) is a humanized IgG1 k monoclonal antibody that binds to PD-1. Pidilizumab is e.g. disclosed in WO 2009/101611.

PDR-001 or PDR001 is a high-affinity, ligand-blocking, humanized anti-PD-1 IgG4 antibody that blocks the binding of PDL-1 and PD-L2 to PD-1. PDR-001 is disclosed in WO2015/112900 and WO2017/019896.

According to this and any other of the aspects of the present invention, antibodies PD1-1 to PD1-5 are antibody molecules as disclosed in EP16170174.3, and are defined by the sequences as shown in Table 9 further below.

Accordingly, PD1-1 has a heavy chain comprising the amino acid sequence of SEQ ID NO:121 and a light chain comprising the amino acid sequence of SEQ ID NO:122;

PD1-2 has a heavy chain comprising the amino acid sequence of SEQ ID NO:123 and a light chain comprising the amino acid sequence of SEQ ID NO:124;

PD1-3 has a heavy chain comprising the amino acid sequence of SEQ ID NO:125 and a light chain comprising the amino acid sequence of SEQ ID NO:126;

PD1-4 has a heavy chain comprising the amino acid sequence of SEQ ID NO:127 and a light chain comprising the amino acid sequence of SEQ ID NO:128; and PD1-5 has a heavy chain comprising the amino acid sequence of SEQ ID NO:129 and a light chain comprising the amino acid sequence of SEQ ID NO:130.

A further aspect of the invention is the use of the anti-CD73 antibody molecule of the invention for preparing a pharmaceutical composition for treating cancer. In a preferred embodiment the aspect further comprises the additional use of a PD-1 antagonist, such as an anti-PD-1 antibody or an anti-PDL-1 antibody. Preferably said anti-PD-1 antibody is selected from the group consisting of pembrolizumab, nivolumab, pidilizumab, PD1-1, PD1-2, PD1-3, PD1-4, and PD1-5 as described herein. Preferably said anti-PDL-1 antibody is selected from the group consisting of atezolizumab, avelumab and durvalumab.

In an embodiment the anti-CD73 antibody molecule is to be administered simultaneously, concurrently, sequentially, successively, alternatively or separately, with the PD-1 antagonist.

The medical use aspects of the invention may comprise any of the specific anti-CD73 antibody molecules of the invention and/or PD-1 antagonist as described herein.

Due to their biological properties, the antibodies of the invention are suitable for treating diseases characterised by excessive or abnormal cell proliferation, such as cancer.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions.

Exemplary cancers whose growth can be inhibited using the antibody molecules disclosed herein include cancers typically responsive to immunotherapy.

For example, the following cancers, tumors, and other proliferative diseases may be treated with antibodies according to the invention, without being restricted thereto:

Examples of solid tumors include malignancies, e.g., sarcomas, and carcinomas (including adenocarcinomas and squamous cell carcinomas) of the various organ systems, such as those affecting liver, lymphoid, genitourinary tract (e.g., renal, urothelial cells), pharynx. Adenocarcinomas include malignancies such as most colon cancers, renal-cell carcinoma, liver cancer, non-small cell carcinoma of the lung, small intestine. Squamous cell carcinomas include malignancies, e.g., in the lung, esophagus, skin, HNSCC, oral cavity, anus, and cervix.

Further indications that may be treated include kidney cancer, e.g. renal cancer such as clear cell carcinoma), gastrointestinal cancer, gastric cancer, CRC, colon carcinoma, cancer of the anal region, pancreatic cancer, ovarian cancer, melanoma (e.g., metastatic malignant melanoma, such as cutaneous or intraocular malignant melanoma), breast cancer, HNSCC, HCC, lung cancer, small-cell lung cancer, non-small cell lung cancer (NSCLC), squamous non-small cell lung cancer (NSCLC), non NSCLC, glioma, endometrial cancer, prostate cancer (e.g. hormone refractory prostate adenocarcinoma or castrate resistant prostate cancer (CRPC)), thyroid cancer, neuroblastoma, glioblastoma (glioblastoma multiforme), cervical cancer, stomach cancer, bladder cancer, hepatoma, germ cell tumor, pediatric sarcoma, sinonasal natural killer lymphoma, bone cancer, uterine cancer, testicular cancer, carcinoma of the fallopian tube, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, spinal axis tumor, brain stem glioma, pituitary adenoma, Kaposi's sarcoma, epidermoid cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), acute lymphoblastic leukemia, chronic lymphocytic leukemia (CLL), chronic lymphoid leukemia, and chronic myelogenous leukemia (CML), undifferentiated AML (MO), myeloblastic leukemia (MI), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B-cell lymphomas, precursor lymphomas, lymphoplasmacytoid lymphoma, lymphocytic lymphoma, acute myeloid lymphoma, monocytoid B-cell lymphoma, mucosa-associated lymphoid tissue (MALT) lymphoma, anaplastic (e.g., Kil+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, T-lymphoblastic lymphoma, peripheral T-cell lymphoma, precursor T-lymphoblastic lymphoma, post-transplantation lymphoproliferative disorder, true histiocytic lymphoma, primary central nervous system lymphoma, primary effusion lymphoma, lymphoblastic lymphoma (LBL), diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), anaplastic large cell lymphoma and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous system, including astrocytoma, schwannomas; tumors of mesenchymal origin, including fibrosarcoma, rhabdomyoscaroma, and osteosarcoma; and other tumors, including xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (TPLL), including of the small cell and cerebriform cell type; large granular lymphocyte leukemia (LGL) preferably of the T-cell type; a/d T-NHL hepatosplenic lymphoma; peripheral/postthymic T cell lymphoma (pleomorphic and immunoblastic subtypes); angiocentric (nasal) T-cell lymphoma; rectal cancer; as well as any combinations of said cancers. The methods described herein may also be used for treatment of metastatic cancers, cancers resistant or refractory to previous treatments (e.g., cancers refractory to previous immunotherapy, e.g., with a blocking CTLA-4 or PD-1 or PDL-1 antibody), and recurrent cancers.

In some embodiments, the cancer is kidney cancer, gastrointestinal cancer or lung cancer. In some embodiments, said gastrointestinal cancer is colon carcinoma, gastric cancer or hepatocellular carcinoma. In some embodiments, said kidney cancer is renal cancer, preferably clear cell carcinoma. In a preferred embodiment of the invention the cancer is lung cancer, preferably non-small cell lung cancer (NSCLC). In some embodiments, said colon carcinoma is CRC.

All cancers, tumors, neoplasms, etc., mentioned above which are characterized by their specific location/origin in the body are meant to include both the primary tumors and the metastatic tumors derived therefrom.

It is possible that a patient is more likely to respond to treatment with an antibody molecule of the invention (as described herein) if that patient has a cancer which is characterized by having a high expression of CD73 (on the cancer cells themselves, or on stromal or immune cells within the tumor); and/or where the cancer is infiltrated by immune cells, e.g. tumor-infiltrating lymphocytes. Although it is expected that some expression of CD73 may be required, the treatment with an antibody molecule of the invention is not necessarily limited to cancers having a high expression of CD73. Hence an embodiment of the invention is wherein the patient to be treated has a cancer which is characterized by having a high expression of CD73 and/or where the cancer is infiltrated by immune cells. In some embodiments, the patient has a cancer which is characterized by having a high expression of PDL-1, and/or CD73 on cancer, stromal or immune cells within the tumor, and is treated both with an anti-CD73 antibody and a PD-1 antagonist as described herein.

Such expression may be determined, for example, on cancer cells, tumor-infiltrating lymphocytes, such as CD8+ T cells or CD4+ T cells, tumor vasculature, tumor stroma, by methods known in the art, such as flow cytometry or immunohistochemistry.

In a preferred embodiment, the patient to be treated is selected based on increased expression of CD73.

Furthermore, it is possible that a patient is more likely to respond to treatment with an antibody molecule of the invention (as described herein) if that patient has a cancer which is characterized by having a high-mutational burden. Examples of how high mutational burden can be assessed include determining whether the cancer is characterized by having microsatellite instabilities, or poor DNA mismatch repair efficiencies. It is thought that such cancers are more immunogenic and hence are more likely to respond to treatment with immunomodulatory therapeutic regimes, such as an antibody molecule of the invention. Hence an embodiment of the invention is wherein the patient to be treated has a cancer which is characterized by having a high-mutational burden.

The antibody molecules of the invention may be used in therapeutic regimens in the context of first line, second line, or any further line treatments.

In one embodiment, the patient to be treated has previously undergone treatment with another treatment agent. In some embodiments, such treatment agent may be a PD-1 antagonist as described herein, such as pembrolizumab, nivolumab, pidilizumab, atezolizumab, avelumab, durvalumab, or PD1-1, PD1-2, PD1-3, PD1-4, and PD1-5 as described herein.

In one embodiment, the patient to be treated is a poor responder to treatment with said treatment agent. For example, the patient may suffer from a cancer that is known to be non-responsive, minimally response, or not sufficiently responsive to treatment with said treatment agent. In one embodiment, a poor responder to treatment with said treatment agent is an individual whose cancer tissue or cancer-adjacent tissue is characterized by insufficient or low levels of inflammation (e.g. compared to a reference). In one embodiment, a poor responder to treatment with said treatment agent is an individual who has received treatment with said treatment agent and whose cancer has progressed. In one embodiment, an individual who is a poor responder or who has a cancer that is poorly responsive is an individual having a poor disease prognosis for treatment with said treatment agent. An individual having a poor response to treatment with said treatment agent can, for example, be identified by a high or higher risk of cancer progression (e.g. compared to individuals having a good disease prognostic), based on one or more predictive factors. In one embodiment, a predictive factor comprises presence of elevated numbers of CD73 expressing T cells and/or elevated levels of CD73-expressing cells or adenosine levels in the tumor microenvironment (in tumor or tumor adjacent tissues). In one embodiment, a predictive factor comprises presence or absence of a mutation in one or more genes. In one embodiment, the mutation defines a neo-epitope recognized by a T cell. In one embodiment, the predictive factor comprises level of expression of one or more genes or proteins in tumor cells, e.g. PDL-1, decreased or elevated levels of PDL-1 on tumor cells. In one embodiment, the predictive factor comprises level of expression of one or more genes or proteins in effector T cells in circulation or in the tumor environment, e.g., PD-1. In one embodiment, the predictive factor comprises a high mutational burden as described above.

In some embodiments, said treatment agent is a PD-1 antagonist as described herein, such as pembrolizumab, nivolumab, pidilizumab, atezolizumab, avelumab, durvalumab, or PD1-1, PD1-2, PD1-3, PD1-4, and PD1-5 as described herein.

The antibody molecules of the invention may be used for the prevention, short-term or long-term treatment of the above-mentioned diseases, optionally also in combination with radiotherapy, chemotherapy and/or surgery. Therefore, in another embodiment, the patient to be treated has previously undergone treatment with radiotherapy or chemotherapy (as further described below). In one embodiment, the patient to be treated is a poor responder to treatment with radiotherapy or chemotherapy, as described above.

Of course, the above also includes the use of the antibody molecules of the invention in various methods of treating the above diseases by administering a therapeutically effective dose to a patient in need thereof, as well as the use of these antibody molecules for the manufacture of medicaments for the treatment of such diseases, as well as pharmaceutical compositions including such antibody molecules of the inventions, as well as the preparation and/or manufacture of medicaments including such antibodies of the invention, and the like.

Combinations with Other Active Substances or Treatments

An anti-CD73 antibody molecule of the invention, or the combination of an anti-CD73 antibody of the invention and a PD-1 antagonist, may be used on its own or in combination with one or more further therapeutic agent(s) or procedure(s), in particular selected from chemotherapeutic agents like DNA damaging agents or therapeutically active compounds that inhibit angiogenesis, signal transduction pathways or mitotic checkpoints in cancer cells.

In some embodiments, the anti-CD73 antibody used in such combination may be any of the antibodies described above in the first aspect of the invention. Preferred anti-CD73 antibodies are B1, B2, C1, C2, C3, C4, C5 and C6 (Table 9). In some embodiments, it is also contemplated that other anti-CD73 antibodies known in the art may be used instead of, or in addition to, the antibodies of the first aspect. Instead of an anti-CD73 antibody of the first aspect of the invention, another anti-CD73 antibody, such as MED19447, BMS986179, CPX-006, CPX-0016, or an antibody as described in WO2008007648, WO2016075099, WO2016081748, WO2016055609, WO2016131950, WO17064043, WO2017100670, WO17152085 or WO2018013611 can also be used.

The additional therapeutic agent may be administered simultaneously with, optionally as a component of the same pharmaceutical preparation, or before or after administration of the antibody molecule.

In certain embodiments, the additional therapeutic agent may be, without limitation, one or more inhibitors selected from the group of inhibitors of EGFR, VEGFR, HER2-neu, Her3, AuroraA, AuroraB, PLK and PI3 kinase, FGFR, PDGFR, Raf, Ras, KSP, IAP (SMAC mimetics), Bcl-2, Mcl-1, HDAC (histone deacetylase), GSK3β, PDK1, PTK2, IGF-R or IR.

Further examples of additional therapeutic agents are inhibitors of CDK, Akt, src/bcr abl, cKit, cMet/HGF, c-Myc, Flt3, HSP90, hedgehog antagonists, inhibitors of JAK/STAT, Mek, mTor, NFkappaB, the proteasome, Rho or an inhibitor of the ubiquitination pathway or another inhibitor of the Notch signaling pathway, or modulators of c-FLIP (cellular FLICE-inhibitory protein).

Examples for Aurora inhibitors are, without limitation, PHA-739358, AZD-1152, AT 9283, CYC-116, R-763, VX-680, VX-667, MLN-8045, PF-3814735.

An example for a PLK inhibitor is GSK-461364.

Examples for raf inhibitors are BAY-73-4506 (also a VEGFR inhibitor), PLX 4032, RAF-265 (also in addition a VEGFR inhibitor), sorafenib (also in addition a VEGFR inhibitor), and XL 281.

Examples for KSP inhibitors are ispinesib, ARRY-520, AZD-4877, CK-1122697, GSK 246053A, GSK-923295, MK-0731, and SB-743921.

Examples for SMAC mimetics (IAP antagonists) are, without limitation, LCL-161, Debio 1143 and ASTX-660.

Examples for src and/or bcr-abl inhibitors are dasatinib, AZD-0530, bosutinib, XL 228 (also an IGF-1 R inhibitor), nilotinib (also a PDGFR and cKit inhibitor), imatinib (also a cKit inhibitor), and NS-187.

An example for a PDK1 inhibitor is BX-517.

An example for a Rho inhibitor is BA-210.

Examples for PI3 kinase inhibitors are PX-866, BEZ-235 (also an mTor inhibitor), XL 418 (also an Akt inhibitor), XL-147, and XL 765 (also an mTor inhibitor).

Examples for inhibitors of cMet or HGF are XL-184 (also an inhibitor of VEGFR, cKit, Flt3), PF-2341066, MK-2461, XL-880 (also an inhibitor of VEGFR), MGCD-265 (also an inhibitor of VEGFR, Ron, Tie2), SU-11274, PHA-665752, AMG-102, and AV-299.

An example for a c-Myc inhibitor is CX-3543.

Examples for Flt3 inhibitors are AC-220 (also an inhibitor of cKit and PDGFR), KW 2449, lestaurtinib (also an inhibitor of VEGFR, PDGFR, PKC), TG-101348 (also an inhibitor of JAK2), XL-999 (also an inhibitor of cKit, FGFR, PDGFR and VEGFR), sunitinib (also an inhibitor of PDGFR, VEGFR and cKit), and tandutinib (also an inhibitor of PDGFR, and cKit).

Examples for HSP90 inhibitors are tanespimycin, alvespimycin, IPI-504 and CNF 2024.

Examples for JAK/STAT inhibitors are CYT-997 (also interacting with tubulin), TG 101348 (also an inhibitor of Flt3), and XL-019.

Examples for Mek inhibitors are ARRY-142886, PD-325901, AZD-8330, and XL 518.

Examples for mTor inhibitors are temsirolimus, AP-23573 (which also acts as a VEGF inhibitor), everolimus (a VEGF inhibitor in addition). XL-765 (also a PI3 kinase inhibitor), and BEZ-235 (also a PI3 kinase inhibitor).

Examples for Akt inhibitors are perifosine, GSK-690693, RX-0201, and triciribine.

Examples for cKit inhibitors are AB-1010, OSI-930 (also acts as a VEGFR inhibitor), AC-220 (also an inhibitor of Flt3 and PDGFR), tandutinib (also an inhibitor of Flt3 and PDGFR), axitinib (also an inhibitor of VEGFR and PDGFR), XL-999 (also an inhibitor of Flt3, PDGFR, VEGFR, FGFR), sunitinib (also an inhibitor of Flt3, PDGFR, VEGFR), and XL-820 (also acts as a VEGFR- and PDGFR inhibitor), imatinib (also a bcr-abl inhibitor), nilotinib (also an inhibitor of bcr-abl and PDGFR).

Examples for hedgehog antagonists are IPI-609 and CUR-61414.

Examples for CDK inhibitors are seliciclib, AT-7519, P-276, ZK-CDK (also inhibiting VEGFR2 and PDGFR), PD-332991, R-547, SNS-032, PHA-690509, and AG 024322.

Examples for proteasome inhibitors are bortezomib, carfilzomib, and NPI-0052 (also an inhibitor of NFkappaB).

An example for an NFkappaB pathway inhibitor is NPI-0052.

An example for an ubiquitination pathway inhibitor is HBX-41108.

In preferred embodiments, the additional therapeutic agent is an anti-angiogenic agent.

Examples for anti-angiogenic agents are inhibitors of the FGFR, PDGFR and VEGFR or the respective ligands (e.g VEGF inhibitors like pegaptanib or the anti-VEGF antibody bevacizumab), and thalidomides, such agents being selected from, without limitation, nintedanib, bevacizumab, motesanib, CDP-791, SU-14813, telatinib, KRN-951, ZK-CDK (also an inhibitor of CDK), ABT-869, BMS-690514, RAF-265, IMC-KDR, IMC-18F1, IMiDs (immunomodulatory drugs), thalidomide derivative CC-4047, lenalidomide, ENMD 0995, IMC-D11, Ki 23057, brivanib, cediranib, XL-999 (also an inhibitor of cKit and Flt3), 163, CP 868596, IMC 3G3, R-1530 (also an inhibitor of Flt3), sunitinib (also an inhibitor of cKit and Flt3), axitinib (also an inhibitor of cKit), lestaurtinib (also an inhibitor of Flt3 and PKC), vatalanib, tandutinib (also an inhibitor of Flt3 and cKit), pazopanib, GW 786034, PF-337210, IMC-1121B, AVE-0005, AG-13736, E-7080, CHIR 258, sorafenib tosylate (also an inhibitor of Raf), RAF-265 (also an inhibitor of Raf), vandetanib, CP-547632, OSI-930, AEE-788 (also an inhibitor of EGFR and Her2), BAY-57-9352 (also an inhibitor of Raf), BAY-73-4506 (also an inhibitor of Raf), XL 880 (also an inhibitor of cMet), XL-647 (also an inhibitor of EGFR and EphB4), XL 820 (also an inhibitor of cKit), and nilotinib (also an inhibitor of cKit and brc-abl).

The additional therapeutic agent may also be selected from EGFR inhibitors, it may be a small molecule EGFR inhibitor or an anti-EGFR antibody. Examples for anti-EGFR antibodies, without limitation, are cetuximab, panitumumab, matuzumab; examples for a small molecule EGFR inhibitor, without limitation, are gefitinib, afatinib, osimertinib and olmutinib. Another example for an EGFR modulator is the EGF fusion toxin.

Among the EGFR and Her2 inhibitors useful for combination with the antibody molecule of the invention are lapatinib, gefitinib, erlotinib, afatinib, cetuximab, trastuzumab, nimotuzumab, zalutumumab, vandetanib (also an inhibitor of VEGFR), pertuzumab, XL-647, HKI-272, BMS-599626 ARRY-334543, AV 412, mAB-806, BMS-690514, JNJ-26483327, AEE-788 (also an inhibitor of VEGFR), ARRY-333786, IMC-11F8, Zemab.

Other agents that may be advantageously combined in a therapy with the antibody molecules of the invention are tositumumab and ibritumomab tiuxetan (two radiolabelled anti-CD20 antibodies), alemtuzumab (an anti-CD52 antibody), denosumab, (an osteoclast differentiation factor ligand inhibitor), galiximab (a CD80 antagonist), ofatumumab (a CD20 inhibitor), zanolimumab (a CD4 antagonist), SGN40 (a CD40 ligand receptor modulator), rituximab (a CD20 inhibitor), epratuzumab (a CD22 antibody) or mapatumumab (a TRAIL-1 receptor agonist).

Other chemotherapeutic drugs that may be used in combination with the antibody molecules of the present invention are selected from, but not limited to hormones, hormonal analogues and antihormonals (e.g. tamoxifen, toremifene, raloxifene, fulvestrant, megestrol acetate, flutamide, nilutamide, bicalutamide, cyproterone acetate, finasteride, buserelin acetate, fludrocortisone, fluoxymesterone, medroxyprogesterone, octreotide, arzoxifene, pasireotide, vapreotide), aromatase inhibitors (e.g. anastrozole, letrozole, liarozole, exemestane, atamestane, formestane), LHRH agonists and antagonists (e.g. goserelin acetate, leuprolide, abarelix, cetrorelix, deslorelin, histrelin, triptorelin), antimetabolites (e.g. antifolates like methotrexate, pemetrexed, pyrimidine analogues like 5 fluorouracil, capecitabine, decitabine, nelarabine, and gemcitabine, purine and adenosine analogues such as mercaptopurine thioguanine, cladribine and pentostatin, cytarabine, fludarabine); antitumor antibiotics (e.g. anthracyclines like doxorubicin, daunorubicin, epirubicin and idarubicin, mitomycin-C, bleomycin dactinomycin, plicamycin, mitoxantrone, pixantrone, streptozocin); platinum derivatives (e.g. cisplatin, oxaliplatin, carboplatin, lobaplatin, satraplatin); alkylating agents (e.g. estramustine, meclorethamine, melphalan, chlorambucil, busulphan, dacarbazine, cyclophosphamide, ifosfamide, hydroxyurea, temozolomide, nitrosoureas such as carmustine and lomustine, thiotepa); antimitotic agents (e.g. vinca alkaloids like vinblastine, vindesine, vinorelbine, vinflunine and vincristine; and taxanes like paclitaxel, docetaxel and their formulations, larotaxel; simotaxel, and epothilones like ixabepilone, patupilone, ZK-EPO); topoisomerase inhibitors (e.g. epipodophyllotoxins like etoposide and etopophos, teniposide, amsacrine, topotecan, irinotecan) and miscellaneous chemotherapeutics such as amifostine, anagrelide, interferone alpha, procarbazine, mitotane, and porfimer, bexarotene, celecoxib.

Particularly preferred are ATP generating chemotherapeutics, e.g. doxorubicin where a positive effect of combining doxorubicin with CD73 blockade has been demonstrated (Loi, Proc Natl Acad Sci USA. 2013; 110(27):11091-6).

In certain embodiments, the additional therapeutic agent may be a further immunotherapeutic agent, such as modulators of: TIM-1, TIM3, TIM-4, PDL-1 (e.g. atezolizumab, avelumab or durvalumab), PD-L2, LAG3, CTLA-4, Galectin 9, Galectin-1, CD69, CD113, GPR56, CD48, GARP, CAECAM-1, BTLA, TIGIT, CD160, LAIR1, 2B4, CEACAM, CD39, TGFβ, IL-10, Fas ligand, ICOS, IDO, Toll-like receptor, B7 family (B7-1, B7-2, B7-H1 (PDL-1), B7-DC (PD-L2), B7-H2 (ICOS-L), B7-H3, B7-H4, B7-H5 (VISTA), and B7-H6).

In some embodiments, the additional immunotherapeutic agent is a member of the TNF family of molecules that bind to cognate TNF receptor family members, which include CD40 and CD40L, OX-40, OX-40L, CD70, CD27L, CD30, CD30L, 4-166L, CD137, GITR, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LIGHT, DcR3, HVEM, VEGI/TLIA, TRAMP/DR3, EDAR, EDAI, XEDAR, EDA2, TNFRI, Lymphotoxin α/TNFβ, TNFR2, TNFα, LTβR, Lymphotoxin α1β2, FAS, FASL, RELT, DR6, TROY, NGFR.

In some embodiments, the additional immunotherapeutic agent is selected from (i) antagonists of cytokines that inhibit T cell activation (e.g., IL-6, IL-10, TGF-B, VEGF; "immunosuppressive cytokines") and/or (ii) agonists of cytokines that stimulate T cell activation and/or cytokines such as IL2, for stimulating an immune response, e.g., for treating proliferative diseases, such as cancer.

In some embodiments, the additional immunotherapeutic agent is an agonist of a protein that stimulates T cell activation, such as CD28, GITRL, OX40L, CD27, and CD28H.

The anti-CD73 antibodies described herein can also be used to design bispecific antibodies that target Fca or Fcγ receptor-expressing effectors cells to tumor cells (see, e.g., U.S. Pat. Nos. 5,922,845 and 5,837,243, which are hereby incorporated by reference). Bispecific antibodies can be used to target two separate antigens.

For example anti-Fc receptor/anti-tumor antigen (e.g., Her-2/neu) bispecific antibodies have been used to target macrophages to sites of tumor. This targeting may more effectively activate tumor specific responses. Alternatively, antigen may be delivered directly to DCs by the use of bispecific antibodies which bind to tumor antigen and a dendritic cell specific cell surface marker.

In other embodiments the immunotherapeutic agent may be a cancer vaccine.

Other molecules that can be combined with CD73 antibodies include antagonists of inhibitory receptors on NK cells or agonists of activating receptors on NK cells, for example antagonists of KIR (e.g. lirilumab.

In some embodiments, the additional therapeutic agent may be an agent that inhibits or depletes macrophages or monocytes, including but not limited to CSF-1R antagonists.

In other embodiments the additional therapeutic agent may be an agent that depletes or blocks Treg cells, e.g. an agent that specifically binds to CD25.

In some embodiments, the additional therapeutic agent may be an inhibitor of the A2A, or A2B receptors. Examples are, but not limited to ATL-444, Istradefylline (KW-6002), MSX-3, Preladenant (SCH-420,814), SCH-58261, SCH-412348, SCH-442416, ST-1535, Caffeine, VER-6623, VER-6947, VER-7835, Vipadenant (BIIB-014), PD116,948, ZM 241385, KW 6002, CGS 15943, ST1535, SYN-115, PSB1115, PSB 603, MRS 1754, CPI-444, PBF-509, AZD-4635 or ZM-241385.

In preferred embodiments, the further therapeutic agent is an A2AR antagonist, CD39 antagonist, LAG-3 antagonist, CTLA-4 antagonist, EGFR antagonist, or HER2 antagonist.

When two or more substances or principles are to be used as part of a combined treatment regimen, they can be administered via the same route of administration or via different routes of administration, at essentially the same time (i.e. simultaneously, concurrently) or at different times (e.g. sequentially, successively, alternately, consecutively, or according to any other sort of alternating regime).

When the substances or principles are to be administered simultaneously via the same route of administration, they may be administered as different pharmaceutical formulations or compositions or as part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Of course, the above includes the preparation, and methods of preparing, the antibodies of the invention for the combined use with the above combination partners. Also included are the preparation, and methods of preparing, the above-mentioned combination partners for the combined use with the antibodies of the invention.

The antibody molecules of the invention may be used on their own or in combination with other treatment regimes, for example surgery and/or radiation therapy.

Kits and Methods of Manufacture and Purification

The invention also encompasses kits comprising at least an anti-CD73 antibody as described herein, and one or more other components selected from the group consisting of other drugs used for the treatment of the diseases and disorders as described above.

In one embodiment, the kit includes a composition containing an effective amount of an anti-CD73 antibody molecule of the invention in unit dosage form. In a further embodiment the kit includes both a composition containing an effective amount of an anti-CD73 antibody molecule of the invention in unit dosage form and a composition containing an effective amount of a PD-1 antagonist in unit dosage form, such as an anti PD-1 antibody, most preferably PD1-1, PD1-2, PD1-3, PD1-4, and PD1-5 as described herein.

In some embodiments, the kit comprises a sterile container which contains such a composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, an anti-CD73 antibody molecule, either alone or in combination with another therapeutic agent, such as a PD-1 antagonist, is/are provided together with instructions for administering the antibody/antibodies to a subject having cancer. The instructions will generally include information about the use of the composition for the treatment or prevention of a cancer. In other embodiments, the instructions include at least one of the following: description of the therapeutic agent; dosage schedule and administration for treatment or prevention of cancer or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

In some embodiments, the kit comprises an anti-CD73 antibody molecule as described herein together with a PD-1 antagonist (as further described herein) and optionally a further therapeutic agent as described herein above.

The invention further provides methods of manufacturing an antibody molecule of the invention, such methods generally comprising the steps of:

- culturing host cells comprising an expression vector comprising a nucleic acid encoding an antibody molecule of the invention under conditions that allow formation of the antibody of the invention; and,
- recovering the antibody molecule expressed by the host cells from the culture; and
- optionally further purifying and/or modifying and/or formulating the antibody molecule of the invention.

A nucleic acid of the invention can e.g. be a DNA molecule comprising coding sequences as well as regulatory sequences and optionally natural or artificial introns, or can be a cDNA molecule. It may have its original codons or may have an optimized codon usage that has been specifically adapted for expression in the intended host cell or host organism. According to one embodiment of the invention, the nucleic acid of the invention is in essentially isolated form, as defined above.

The nucleic acid of the invention will typically be incorporated into an expression vector, i.e. a vector that can provide for expression of the polypeptide when transfected into a suitable host cell or other expression system.

For manufacturing the antibodies of the invention, the skilled artisan may choose from a great variety of expression systems well known in the art, e.g. those reviewed by Kipriyanow and Le Gall, 2004.

Expression vectors include plasmids, retroviruses, cosmids, EBV derived episomes, and the like. The expression vector and expression control sequences are selected to be compatible with the host cell. The antibody light chain gene and the antibody heavy chain gene can be inserted into separate vectors. In certain embodiments, both DNA sequences are inserted into the same expression vector.

Convenient vectors are those that encode a functionally complete human CH (constant heavy) or CL (constant light) immunoglobulin sequence, with appropriate restriction sites engineered so that any VH (variable heavy) or VL (variable light) sequence can be easily inserted and expressed, as described above. For the antibody heavy chain, it can be, without limitation, any IgG isotype (IgG1, IgG2, IgG3, IgG4) or other immunoglobulins, including allelic variants.

The recombinant expression vector may also encode a signal peptide that facilitates secretion of the antibody chain from a host cell. The DNA encoding the antibody chain may be cloned into the vector such that the signal peptide is linked in-frame to the amino terminus of the mature antibody chain DNA. The signal peptide may be an immunoglobulin signal peptide or a heterologous peptide from a non-immunoglobulin protein. Alternatively, the DNA sequence encoding the antibody chain may already contain a signal peptide sequence.

In addition to the antibody chain DNA sequences, the recombinant expression vectors typically carry regulatory sequences, optionally heterologous regulatory sequences, including promoters, enhancers, termination and polyadenylation signals and other expression control elements that control the expression of the antibody chains in a host cell. Examples for promoter sequences (exemplified for expression in mammalian cells) are promoters and/or enhancers derived from CMV (such as the CMV Simian Virus 40 (SV40) promoter/enhancer), adenovirus, (e. g., the adenovirus major late promoter (AdMLP)), polyoma and strong mammalian promoters such as native immunoglobulin and actin promoters. Examples for polyadenylation signals are BGH polyA, SV40 late or early polyA; alternatively, 3"UTRs of immunoglobulin genes etc. can be used.

The recombinant expression vectors may also carry sequences that regulate replication of the vector in host cells (e. g. origins of replication) and selectable marker genes. Nucleic acid molecules encoding the heavy chain or an antigen-binding portion thereof and/or the light chain or an antigen-binding portion thereof of an antibody of the invention, and vectors comprising these DNA molecules can be introduced into host cells, e.g. bacterial cells or higher eukaryotic cells, e.g. mammalian cells, according to transfection methods well known in the art, including liposome-mediated transfection, polycation-mediated transfection, protoplast fusion, microinjections, calcium phosphate precipitation, electroporation or transfer by viral vectors.

Preferably, the DNA molecules encoding the heavy chain and the light chain are present on two expression vectors which are co-transfected into the host cell, preferably a mammalian cell.

Mammalian cell lines available as hosts for expression are well known in the art and include, inter alia, Chinese hamster ovary (CHO) cells, NSO, SP2/0 cells, HeLa cells, baby hamster kidney (BHK) cells, monkey kidney cells (COS), human carcinoma cells (e. g., Hep G2 and A-549 cells), 3T3 cells or the derivatives/progenies of any such cell line. Other mammalian cells, including but not limited to human, mice, rat, monkey and rodent cells lines, or other eukaryotic cells, including but not limited to yeast, insect and plant cells, or prokaryotic cells such as bacteria may be used.

The antibody molecules of the invention are produced by culturing the host cells for a period of time sufficient to allow for expression of the antibody molecule in the host cells. Antibody molecules are preferably recovered from the culture medium as a secreted polypeptide or it can be recovered from host cell lysates if for example expressed without a secretory signal. It is necessary to purify the antibody molecules using standard protein purification methods used for recombinant proteins and host cell proteins in a way that substantially homogenous preparations of the antibody are obtained. By way of example, state-of-the art purification methods useful for obtaining antibody molecules of the invention include, as a first step, removal of cells and/or particulate cell debris from the culture medium or lysate. The antibody is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. As a final step in the process for obtaining an antibody molecule preparation, the purified antibody molecule may be dried, e.g. lyophilized, as described below for therapeutic applications.

The present invention is further illustrated by the following examples, without being necessarily limited to these embodiments of the invention. An example or part thereof, including compounds, doses and administration routes, as well as treatment combinations, each as such or in combination with the detailed description above forms part of the invention.

EXAMPLES

Example 1: Generation and Optimization of Antibodies Against CD73

CD73 knock-out mice were immunized with the complete extracellular domain of human CD73 (UniProt accession no. P21589) having a C-terminal 6×His tag and the complete extracellular domain of mouse CD73 (UniProt accession no. Q61503; having a C-terminal Human Fc tag (SEQ ID NO: 131). Hits were identified and recovered by using a single B-cell antibody generation platform. They were screened for binding to human, cynomolgus, mouse, and rat CD73, and tested for inhibition of CD73 in functional assays, as described in Examples 2 to 6. The antibody molecules having the best set of properties according to these assays were used as a basis for further optimized variants.

The CDRs from these anti-CD73 mouse antibodies were sequence-optimized on to human frameworks from closely matching germlines for heavy and light chains using a phage screening method (as described by Singh et al MAbs. 2015 July-August; 7(4): 778-791). The binding activity of the variants were evaluated by ELISA. Variants having high affinity to human CD73 with a high ratio of human residues and low predicted immunogenicity (low Epivax score) were selected.

Example 2: Target Binding and Cellular Selectivity

For the avidity format, the experiment was performed on a Bio-Rad ProteOn XPR36 instrument. Antibodies were captured via Protein A/G and the non-covalent dimeric antigens were flowed over the captured surface. The running buffer for this experiment and all dilutions were prepared in PBS-T-EDTA. The GLM sensor chip was normalized and pre-conditioned as per the manufacturer's recommendations. The sensor chip was activated with an equal mixture of EDC/s-NHS in the horizontal direction for 300 s at a flow rate of 30 μL/min and immobilized with recombinant Protein A/G (50 μg/ml in 10 mM acetate pH 4.5) in the horizontal direction for 300 s at a flow rate of 30 μL/min resulting in about 5000 RU of Protein A/G on the surface. The sensor chip was deactivated with 1M ethanolamine-HCl in the horizontal direction for 300 s at a flow rate of 30 μL/min. The sensor chip was regenerated with 18 s of 0.85% phosphoric acid at a flow rate of 100 μL/min 2 times horizontally and 2 times vertically.

About 300 RU of antibody was captured on the Protein A/G surface vertically for 60 s at a flow rate of 30 μL/min. The capture surface was stabilized by injecting PBS-T-EDTA for 60 s at a flowrate of 100 μL/min horizontally. The analyte (human CD73-His) was injected horizontally over the captured antibody for 600 s at a flow rate of 30 μL/min with a dissociation of 1200 s. The concentrations of human CD73-His were 0 nM, 3.125 nM, 6.25 nM, 12.5 nM, 25 nM and 50 nM. The surface was regenerated by injecting 0.85% phosphoric acid for 18 s at a flow rate of 100 μL/min one time horizontally and one time vertically.

The interspot (interactions with sensor surface) and blank (PBS-T-EDTA or 0 nM analyte) were subtracted from the raw data. Using the Bio-Rad ProteOn Manager software, sensorgrams were fit globally to 1:1 Langmuir binding to provide association rate constant (ka), dissociation rate constant (kd), and equilibrium dissociation constant (KD) values.

TABLE 1

Binding avidity of anti-CD73 antibodies to CD73 by SPR

| Antibody | $K_D$ [pM] |
|---|---|
| B2 | 420 |
| C1 | 72 |
| C2 | 63 |
| C3 | 72 |
| C4 | 74 |
| C5 | 49 |
| C6 | 96 |

Cellular selectivity was determined using cell lines which endogenously express CD73, as well as a CD73 negative cell line in a FACS-based assay. In CD73 positive cells binding was readily detected, whereas in cells negative for CD73 no detectable binding was observed up to concentrations of 1000 nM.

Binding of the anti-CD73 was also determined for mouse CD73 by SPR and compared to binding to human CD73 (P21589, "long isoform").

The tested antibodies bound to human CD73 with higher affinity than to mouse CD73 (C1: 96-fold; C2: 138-fold; C3: 117-fold; C4: 120-fold; C5: 163-fold, C6: 58-fold higher binding to human CD73 than to mouse CD73).

Example 3: Inhibition of CD73 Enzymatic Function

CD73 enzymatic function was measured using a luciferase-based assay. The CD73 substrate AMP is a product of the luciferase reaction and shows inhibitory activity towards luciferase. Plates were blocked followed by addition of recombinant human CD73 protein. Then CD73 antibodies were added at different concentrations. Plates were mixed and incubated for 10 min at 37° C. The substrate AMP was added, plates were mixed and incubated at 37° C. for 30 min. The CellTiterGlo reagent (CellTiterGlo Luminescent Cell Viability Assay Kit, Promega, catalog number #G7571) was dissolved in Reagent Buffer and added to each well. The plate was mixed and incubated for 10 min at RT in the dark. The luminescence signal was measured using an EnVision 2104 Multilabel Reader.

As shown in Table 2, CD73 antibodies described herein show low nanomolar 1090 values for inhibition of the enzyme function of CD73. Data shown are from two independent experiments.

TABLE 2

Inhibition of CD73 enzymatic function by anti-CD73 antibodies.

| Antibody | $IC_{90}$ [nM] mean +/− SD |
|---|---|
| B2 | 1.04 +/− 0.12 |
| C1 | 0.49 +/− 0.09 |
| C2 | 0.49 +/− 0.08 |
| C3 | 0.32 +/− 0.01 |
| C4 | 0.24 +/− 0.08 |
| C5 | 0.29 +/− 0.05 |
| C6 | 0.24 +/− 0.03 |

Example 4: Reduction of CD73 Protein Surface Levels

The reduction of CD73 protein surface levels was determined by flow cytometry. The Colo201 cell line was incubated with CD73 antibodies for 1 h and for 24 h, and a secondary antibody was used to measure the CD73-bound antibody levels on the cell surface.

Colo201 cells were detached by adding TripLE solution (Gibco, No. 12604-013) and seeded in 96 well plates. After 24 hours CD73 antibodies were added. Samples were analyzed after 1 hour and 24 hours by flow cytometry using a labeled secondary antibody. Sample analysis was carried out using the FlowJo X software version 10.0.7r2. The mean fluorescence intensity (FI) of the gated population was normalized to their corresponding mean FI at timepoint 0 (1 h incubation with CD73 antibody). The data was then normalized whereby the fluorescence value of cells incubated with a CD73 antibody not inducing a CD73 surface level reduction (as disclosed in US20090203538 as “067-213 antibody”) was set to 100% (maximum CD73 levels).

The CD73 antibodies described herein show moderate activity in inducing a reduction of CD73 surface levels. Data shown are from at least two independent experiments.

TABLE 3

Reduction of CD73 surface levels by anti-CD73 antibodies.

| Antibody | CD73 surface reduction [%] mean +/− SD |
|---|---|
| B2 | 31 +/− 0.1 |
| C1 | 20 +/− 3.1 |
| C2 | 15 +/− 1.4 |
| C3 | 16 +/− 1.5 |
| C4 | 15 +/− 1.4 |
| C5 | 19 +/− 1.5 |
| C6 | 19 +/− 5.9 |
| “MEDI 9447” | 17 +/− 3.9 |
| “BMS 986179” | 58 +/− 1.7 |

Example 5: Inhibition of Adenosine Formation in Cell Lines

A cell-based assay was used to determine the reduction of adenosine levels by CD73 inhibition. Addition of AMP to Colo-201 cells results in the conversion of AMP to adenosine by CD73 expressed on the cells. The conversion of AMP is inhibited by the anti-CD73 antibodies of the invention as provided herein. Colo-201 cells were cultivated in the presence of CD73 antibodies at 37° C. for 24 hours. Then a blocking solution was added containing Erythro-9-(2-hydroxy-3-nonyl)adenine to block adenosine deaminase, 5-lodotubercidin to block adenosine kinase, f3-glycerophosphate to block alkaline phosphatase and dipyridamole to block ENT1-4 (Ramakers 2008). After an incubation of 20 minutes, 300 μM AMP was added for 30 minutes and the reaction was stopped by addition of a 15 mM HCl solution. 50 μl aliquots of cell supernatants taken from the incubations for each mAb concentration were added to 500 μl acetonitrile containing 0.5 mM isotope-labelled $^{13}$C5-adenosine as internal standard+50 μl of blocking solution in a 96-well plate format. Calibration standards were prepared by serial dilutions in twelve steps. Calibration and quality control samples were prepared by adding 50 μl cell incubation medium as blank matrix plus 50 μl of the respective standard or QC solution to 500 μl acetonitrile containing 0.5 mM isotope-labelled $^{13}$C5-adenosine as internal standard. After centrifugation 50 μl of supernatant were transferred to another 96-well plate, evaporated to dryness under $N_2$ and redissolved in 25% methanol+0.01% formic acid. Adenosine concentrations were determined by HPLC-MS/MS at unit mass resolution with ESI+ ionization. Samples were injected into the HPLC/MS system with a CTC PAL HTS-xt autosampler (injection volume 5 μL). Quantitative analyses were performed with Agilent HP1200 HPLC systems equipped with a Phenomenex Synergy Hydro-RP C18 reversed phase HPLC column at room temperature (particle size 2.5 μm, column dimension 2×50 mm), applying a HPLC gradient with 5 mmol/L ammonium acetate (pH 4.0) as solvent A and acetonitrile with 0.1% formic acid as solvent B with a flow rate of 700 μl/min and a cycle time of 5 min per sample. Solvent B was increased from 2 to 15% from 0 to 3.0 min, increased to 95% B from 3.0 to 3.1 min, kept constant at 95% B from 3.1 to 4.0 min before returning to 2% B from 4.0 to 4.1 min and column re-equilibration from 4.1 to 5.0 min. The HPLC systems were coupled to ABSCIEX API5000 triple quadrupole mass spectrometers operated in MRM mode. Declustering potential (DP) and collision energy (CE) settings were automatically optimized using the ABSCIEX DiscoveryQuant™ 2.1 software. MRM transitions of 268.2 to 136.1 (DP: 62, CE: 27) for adenosine and 273.3 to 136.2 (DP: 64, CE: 27) for $^{13}C_5$-adenosine were used for the quantitation (dwell times: 70 ms). The source temperature of the Turbo Ion Spray source was set to 650° C. Chromatograms were integrated and peak areas were determined with Analyst® 1.5.1 (ABSCIEX). Absolute amounts of adenosine formed were calculated from measured adenosine concentrations and incubation volumes. Data were fitted by iterative calculation using a symmetrical sigmoidal curve analysis program (Graph Pad PRISM) with variable hill slope. Adenosine levels obtained for isotype-treated cells without AMP addition are set to 100% inhibition; adenosine levels obtained for isotype-treated cells with AMP addition are set to 0% inhibition.

The CD73 antibodies described herein reduced adenosine levels in Colo201 cells by >75% compared to isotype-treated cells+/−AMP addition.

The anti-CD73 antibodies described herein showed superior activity in reducing adenosine levels in Colo201 cells compared to the reference anti-CD73 antibodies “MED19447” and “BMS986179” (as defined herein above), as demonstrated in Table 4.

TABLE 4

Inhibition of adenosine formation in Colo201 cells.

| Antibody | Max. adenosine inhibition [%] |
|---|---|
| B2 | 77 |
| C1 | 86 |
| C2 | 88 |
| C3 | 88 |
| C4 | 88 |
| C5 | 87 |
| C6 | 88 |
| "MEDI 9447" | 63 |
| "BMS 986179" | 68 |

Example 6: Induction of T Cell Proliferation and IFNγ Release

The effect of CD73 inhibition on T cells was investigated using a primary human T cell assay. Human peripheral blood mononuclear cells (PBMCs) from STEMCELL Technologies were thawed and T cells were enriched by negative selection (T-Cell enrichment Kit, Easy Sep Negative Selection; Stem Technologies #19051). Donors were internally labeled donor A-F. T cells were labeled with Cell Trace Violet (CellTrace™ Violet Proliferation Kit, Molecular Probes, #C34557) according to the manufacturer's protocol. The assay was performed in a 96 well round bottom plate pre-coated with anti-CD3 (Ultra-LEAF™ purified anti-CD3 antibody, clone HIT3a, Biolegend, #300332) overnight at 4° C. CTV-labeled T cells were plated and incubated with anti-CD28 (Ultra-LEAF™ purified anti-CD28 antibody, clone CD28.2; Biolegend, #302934) and anti-huCD73 or anti-TNP HulgG1K0 control at different concentrations. After 22 hours incubation at 37° C. and 5% CO2, AMP (Adenosine 5'-monophosphate disodium salt; Sigma Aldrich, Cat#01930) was added at a final concentration of 200 μM. Cells were incubated at 37° C. and 5% $CO_2$ for another 5 days. Supernatants were taken and analysed for IFN gamma secretion by Meso Scale Diagnostics V-PLEX Human IFN-γ Kit according to the manufacturer's instructions. Values were normalized to stimulated isotype-treated cells with AMP addition. Proliferation of cells was determined by analysis of the CTV label on CD4+ and CD8+ cells using a BD FACS Canto II Flow Cytometer and the BD FACSDiva software (Version 8.0.1). Proliferation of stimulated isotype-treated cells without AMP addition was set to 100%, proliferation of stimulated isotype-treated cells with AMP addition was set to 0%.

The CD73 antibodies described herein restore T cell proliferation and cytokine release.

The antibodies described herein show superior activity in inducing T cell proliferation and IFNγ release in primary human T cells in certain donors compared to "MED19447" and "BMS986179" (Table 5 and 6). Thus, the CD73 antibodies generated have the capacity to restore functions of T cells suppressed by AMP to higher levels compared to both competitor molecules in certain donors.

TABLE 5

CD8 T cell proliferation, provided in [%] of control (isotype-treated cells +/− AMP, whereby stimulated isotype-treated cells without AMP addition are set to 100% and stimulated isotype-treated cells with AMP addition are set to 0%); n.d.: not determined

| CD73 mAb | Donor A | Donor B | Donor C | Donor D | Donor E | Donor F |
|---|---|---|---|---|---|---|
| B2 | 55.6 | 62.2 | 95.8 | 98.5 | 99.1 | −8.9 |
| C1 | 103.5 | 86.7 | 106.9 | 99.5 | 100.9 | 84.2 |
| C2 | 103.0 | 68.5 | n.d. | n.d. | n.d. | n.d. |
| C3 | 103.2 | 80.2 | 116.5 | 99.3 | 101.0 | 91.3 |
| C4 | 103.5 | 70.3 | 110.9 | 98.5 | 100.2 | 92.6 |
| C5 | 103.2 | 80.3 | 100.6 | 99.3 | 100.4 | 86.0 |
| C6 | 102.4 | 65.4 | 88.3 | 99.6 | 100.4 | 91.1 |
| "MEDI9447" | 43.9 | 46.7 | 115.1 | 98.0 | 85.5 | −34.1 |
| "BMS986179" | 40.7 | 61.7 | 99.6 | 98.7 | 95.4 | 22.5 |

TABLE 6

IFNγ release [fold change over control]. The control is stimulated isotype-treated cells with AMP addition.

| CD73 mAb | Donor A | Donor B | Donor C | Donor D | Donor E | Donor F |
|---|---|---|---|---|---|---|
| B2 | 12.6 | 8.1 | 34.1 | 17.7 | 11.1 | 3.1 |
| C1 | 20.9 | 12.0 | 51.3 | 20.9 | 12.8 | 6.7 |
| C2 | 20.3 | 7.8 | n.d. | n.d. | n.d. | n.d. |
| C3 | 19.9 | 7.7 | 31.9 | 19.0 | 14.2 | 6.7 |
| C4 | 20.2 | 8.7 | 35.2 | 13.7 | 14.1 | 7.1 |
| C5 | 24.5 | 11.3 | 59.3 | 22.9 | 12.4 | 5.8 |
| C6 | 24.3 | 12.9 | 55.5 | 25.8 | 14.0 | 10.3 |
| "MEDI9447" | 7.7 | 5.3 | 16.2 | 20.7 | 5.0 | 1.1 |
| "BMS986179" | 10.9 | 5.2 | 36.4 | 13.3 | 7.2 | 2.9 |

Table 5 and 6 above demonstrate that the tested anti-CD73 antibodies show superior activity in inducing T cell proliferation and IFNγ release in certain donors compared to "MEDI9447" and "BMS986179". Data are from head to head comparisons at CD73 antibody concentration of 1 nM; 4 biological replicates per donor.

Example 7: Dendritic Cell/T Cell Co-Culture

Further, a dendritic cell/T cell co-culture system was established. Human peripheral blood mononuclear cells (PBMCs) were isolated from heparinized blood of healthy donors by Ficoll-Hypaque density gradient centrifugation and stored frozen at −150° C. PBMCs were thawed and monocytes were enriched by negative selection (magnetic beads). Monocytes were cultivated in medium with 3 ng/ml human IL-4 and 50 ng/ml human GM-CSF at 37° C. and 5% $CO_2$ to differentiate to dendritic cells (DCs). On day 5 10 ng/ml TNF alpha was added for maturation and cells were cultivated overnight. PBMCs from a different donor were thawed, T cells were isolated by immunomagnetic negative selection and cultivated overnight in medium with 5 ng/ml human IL-2. 200000 cells per well of T cells were co-cultured with 50000 cells per well of allogenic mature DCs in 96 well plates in the presence of the antiPD-1 antibody pembrolizumab (as further described herein, and e.g. in WO2009/114335 and WO2015/088847) and various anti-CD73 antibodies of the invention at different concentrations. Human IgG4Pro and human IgG1 KO isotype controls were used as a negative control. After 22 hours at 37° C. and 5% CO2 Adenosine 5'-monophosphate disodium salt (AMP) was added. The co-culture was incubated for 5 days at 37° C., then supernatants were taken and IFN gamma secretion was analyzed by Meso Scale Diagnostics V-PLEX Human IFN-γ Kit according to the manufacturer's instructions.

Effects of inhibiting PD1, CD73 or both can be investigated in this system. Addition of AMP was found to inhibit the anti-PD1 response, and anti-CD73 treatment using the antibodies provided herein led to a reversal of this AMP-mediated inhibition (see FIG. 1). Data shown are from head to head comparisons at CD73 antibody concentration of 1 μg/ml; 5 biological replicates per donor and antibody.

Example 8: Inhibition of Cell-Bound Vs Non-Cell-Bound CD73

Colo-201 cells were incubated with CD73 antibodies at 37° C. for 24 hours, then the blocking solution (see "Inhibition of adenosine formation in cell lines") was added for 20 minutes. Cells were pelleted by centrifugation and supernatant was transferred into a new low binding plate. The cells were washed and 300 μM AMP was added to the cells as well as to the supernatant. After an incubation time of 30 minutes, the reaction was stopped by addition of a 15 mM HCl solution. Supernatants were taken and mixed with an acetonitril/blocking solution mixture to stop possible enzyme reactions. Samples were analysed for adenosine levels by liquid chromatography-mass spectrometry. This allows investigating inhibition of cell-bound CD73 versus inhibition of CD73 in cell culture supernatants (non-cell-bound CD73). Adenosine levels obtained for isotype treatment without AMP addition were set to 100% inhibition; adenosine levels obtained for isotype treatment with AMP addition were set to 0% inhibition. As demonstrated in Tables 7 and 8, the CD73 antibodies according to the present invention, in particular C1, C2, C3, C4, C5 and C6, inhibited cell-bound CD73 as well as CD73 present in cell culture supernatants (non-cell-bound CD73) by 70-80%. "MED19447" displayed an approximately 20% lower inhibitory activity on cell-bound CD73. Both "MED19447" and "BMS 986179" showed lower activities in inhibiting CD73 present in cell culture supernatants. Thus, the CD73 antibodies according to the present invention led to a more complete inhibition of CD73 compared to both competitor molecules.

TABLE 7

Inhibition of cell-bound CD73

| Antibody | % of max. adenosine inhibition |
|---|---|
| B2 | 70 +/− 3 |
| C1 | 79 +/− 3 |
| C2 | 78 |
| C3 | 81 +/− 4 |
| C4 | 82 +/− 3 |
| C5 | 82 +/− 6 |
| C6 | 81 +/− 3 |
| "MEDI 9447" | 62 +/− 4 |
| "BMS 986179" | 84 +/− 5 |

Table 7 demonstrates that the antibodies of the invention are superior to the comparative prior art antibody "MEDI 9447" in inhibiting cell-bound CD73. Data shown is from at least two independent experiments apart from antibody C2 (n=1).

TABLE 8

Inhibition of non-cell-bound CD73

| Antibody | % of max. adenosine inhibition |
|---|---|
| B2 | 62 +/− 2 |
| C1 | 76 +/− 3 |
| C2 | 77 |
| C3 | 82 +/− 3 |
| C4 | 81 +/− 1 |
| C5 | 80 +/− 5 |
| C6 | 78 +/− 2 |
| "MEDI 9447" | 56 +/− 7 |
| "BMS 986179" | 63 +/− 1 |

Table 8 demonstrates that the antibodies of the invention are superior to the comparative prior art antibodies "MEDI 9447" and/or "BMS 986179" in inhibiting CD73 in cell culture supernatants. Data shown is from at least two independent experiments apart from antibody C2 (n=1).

Example 9: Complex Formation of Anti-CD73 Antibodies and CD73

The oligomeric state of the complexes of CD73 and two anti-CD73 antibodies was investigated using samples of CD73 and two different antibodies by sedimentation velocity analytical ultracentrifugation ("SV-AUC") experiments as single components and as mixtures with an 1:1 molar CD73:antibody ratio. For optimal signal to noise ratio at 280 nm, the mixtures were examined at a concentration of 2.4 μM. Individual aliquots of CD-73 protein and the inventive antibody were also examined at a concentration of 2.4 μMolar to facilitate g(s) comparison. CD73 protein and the inventive antibody were dialyzed into PBS buffer prior to mixing and centrifugation.

SV-AUC experiments were analyzed qualitatively by preparing g(s) distribution curves by a transformation of the raw data, and more quantitatively by various curve fitting algorithms. For paucidisperse non-reversible systems, or reversible systems with concentrations greater than or equal to 2 orders of magnitude above all interaction $K_D$ values, the c(s) distribution function is a robust curve fitting method that will return accurate estimates of percentage of each species and molecular weight. The individual components (CD73 and the associated anti-CD73 antibodies (inventive anti-CD73 antibody C4; "MED19447") were of sufficient purity to be curve fit by the c(s) algorithm and returned the expected molecular weights. The mixtures of CD73 protein with anti-CD-73 antibodies gave broad distributions that were not amenable to deconvolution by the c(s) algorithm, so a g(s), apparent sedimentation distribution plot, was made to qualitatively compare the distribution of species formed by CD73 and anti-CD73 antibodies.

Materials

CD73 HuCD73_His_tagged, molecular weight of dimer (Daltons): 118,032, partial specific volume 0.73744, A280/mg/ml/cm 0.954, storage buffer 1×PBS, 0.2 M Sucrose, 0.01% CHAPS, 5% Glycerol, 1 mM TCEP, pH-7.2.

Anti-CD73 antibody C04, calculated molecular weight is 148,232 Da, including 3000 Da for glycosylation. Anti-CD73 antibody "MED19447", calculated molecular weight including estimated 3000 Da for glycosylation is150,669 Da.

Methods

Data collection for SV-AUC experiments were performed with a Beckman XL-I analytical ultracentrifuge (Beckman Coulter, Brea, Calif.). On the day of each experiment, samples stored at the appropriate storage temperature were thawed, if necessary, and at room temperature are mixed gently by pipette, and diluted to a concentration resulting in an absorbance signal within the linear range of the detector. Samples were loaded into the sample sectors of charcoal-filled epon cells with sapphire or quartz windows. The sample sector was loaded with 400 μL of diluted sample. 406 μL of matched buffer was used in the reference sector of the cell. Experiments were carried out using an analytical four-hole titanium An-60 Ti rotor (Beckman Coulter). The calibration counterweight was placed in hole 4. An initial scan at 3000 RPM was performed to verify cell integrity and to perform a radial calibration for the instrument. Also a wavelength scan was performed on each cell at 3000 RPM to verify absorbance. Samples were allowed to reach temperature equilibrium at 20° C. for at least 2 h before initiation of centrifugation at high speed, 40,000 RPM. The data scans of each cell reporting concentration as a function of radial position were collected by absorbance scanning at 280 nm with a radial step size of 0.003 cm, continuous scanning, 1 flash per channel.

Data Analysis of SV-AUC Using the c(s) Algorithm.

Scans were chosen from the first scan to about the 10th scan after the sample has pelleted. Excess scans after the sample had pelleted contain no information and overly weight the baseline contribution. Buffer properties and an estimate of the partial specific volume calculated by the protein sequence were input as parameters to the curve fit. Data were analyzed, producing continuous c(s) distributions using the software package SEDFIT version 15.01b (Schuck Biophys J. 2000 March; 78(3):1606-19).

Apparent sedimentation coefficient distribution functions, g(s) curves, and whole boundary curve fitting were performed with the program SEDANAL (w w w sedanal.org; Biophysical Chemistry 108 (2004) 231-243). All c(r) data files were examined and metadata such as the meniscus position, range to fit, cell base, and optical corrections, if needed, were written to a channel data file (*.abr file for SEDANAL). The g(s) plot is the apparent sedimentation distribution function plot and represents a transformation of the raw data onto an x-axis of apparent sedimentation coefficient (or speed axis) and onto the y-axis of the g(s) function (a form of derivative of the c(r) data). This is a model free transformation and the position of the peaks represent the speed of the boundary while the width of the boundary represents either the diffusion of single species or diffusion and the growing separation of multiple species (if multiple species are present). A small number of c(r) pairs are used to generate each g(s) plot. The exact shapes of g(s) plots depend on the time span and the elapsed time from the start of rotation of the data used to generate the plot. On the x-axis, the g(s) of even a single ideal species will become more narrow and taller proportional to the elapsed time of the scans from the start of sedimentation. Overlays of time span matched sets of g(s) plots may be used to demonstrate or invalidate reversible self-association of a dilution series of the same sample.

SEDANAL will also perform direct curve fits to raw data transformed by the dc/dt (change in concentration divided by change in time) operation. Using a model specified by the user, SEDANAL does a non-linear least squares curve fit of the dc/dt curves of a subset of a data channel to obtain the best fit parameters of the model to the data. SV-AUC is one of the few biophysical methods that can rank the goodness of fit of a number of models, helping the analyst choose the best model to fit the data.

Results

A sample of CD73 was run at and curve fit by SEDANAL and SEDFIT.

| SEDANAL curve fit for HuCD73his20170303 | |
|---|---|
| S value | 6.341 |
| Weight | 121000 |
| Sedfit curve fit for HuCD73his20170303 | |
| S value | 6.389 |
| Weight | 126000 |

The sample of C04 was run and curve fit by SEDANAL and SEDFIT

| SEDFIT curve fit for C04 | |
|---|---|
| S value | 6.304 |
| Weight | 141000 |
| SEDFIT curve fit for C04 | |
| S value | 6.300 |
| Weight | 144000 |

The sample "MED19447" was run and curve fit by SEDANAL and SEDFIT

| SEDANAL curve fit for "MEDI9447" | |
|---|---|
| S value | 6.347 |
| Weight | 141000 |
| SEDFIT curve fit for "MEDI9447" | |
| S value | 6.321 |
| Weight | 147000 |

Figure 2:
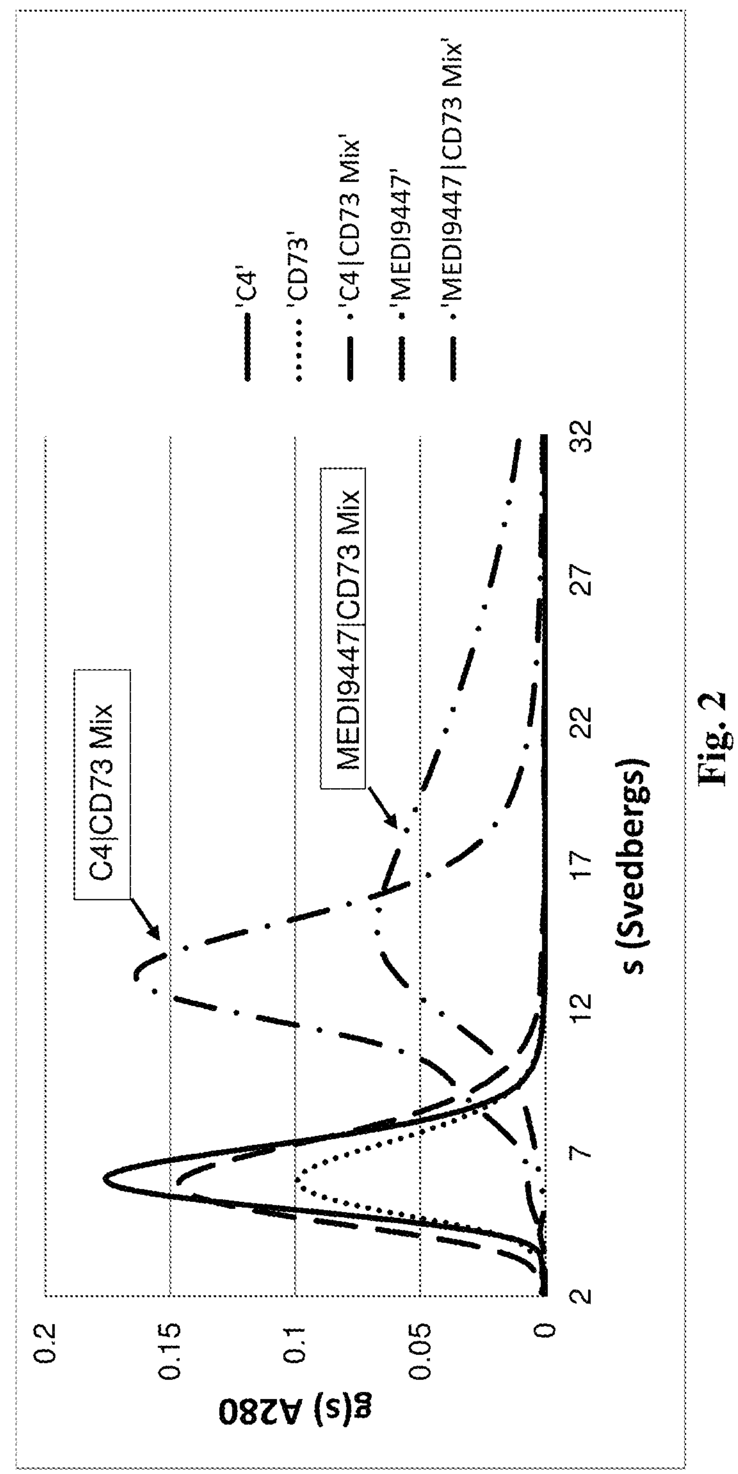
FIG. 2: Complex formation of anti-CD73 antibodies and CD73. Depicted is the assessment of the oligomeric state of complexes of CD73 and two anti-CD73 antibodies (as described in Example 9). The anti-CD73 antibody molecule according to the invention forms antigen-antibody complexes with soluble CD73 with a defined size, such as a 2:2 oligomer. These complexes are smaller compared to complexes formed by other CD73 antibodies known in the art, such as "MED19447".

Curve fitting the mixtures by c(s) and SEDANAL did not return reliable results and the conclusion was that there were too many species to deconvolute. For qualitative comparison, g(s) overlay graphs were prepared (see: FIG. 2).

Correlation between Svedbergs and molecular weight:

| (Svedbergs) | Mw Daltons |
|---|---|
| 2 | 30,000 |
| 4 | 85,000 |
| 6 | 156,000 |
| 8 | 241,000 |
| 10 | 337,000 |
| 12 | 442,000 |
| 14 | 558,000 |
| 16 | 681,000 |
| 18 | 813,000 |
| 20 | 952,000 |
| 24 | 1,250,000 |
| 28 | 1,580,000 |
| 32 | 1,930,000 |

Example 10: Crystallography

Cd73 Protein:

The CD73 protein construct is based on Knapp, K. Et al. (2012) Structure 20: 2161-2173 (10.103/j.str.2012.10.001) and comprises mutations to support protein production and crystallization behaviour. The respective mutations are ASN53ASP, LYS145SER, LYS147SER, ASN311ASP, ASN333ASP, ASN403ASP, LYS478SER, in addition it contains SER, PRO, ASP, PRO at the N-terminus after cleavage with enterokinase. It was expressed, refolded and purified as described in Knapp, K. Et al. (2012) Structure 20: 2161-2173.

FAB:

The Fab fragment of an anti-CD73 antibody according to the invention was obtained by enterokinase cleavage.

Crystal Structure Determination

Figure 3:
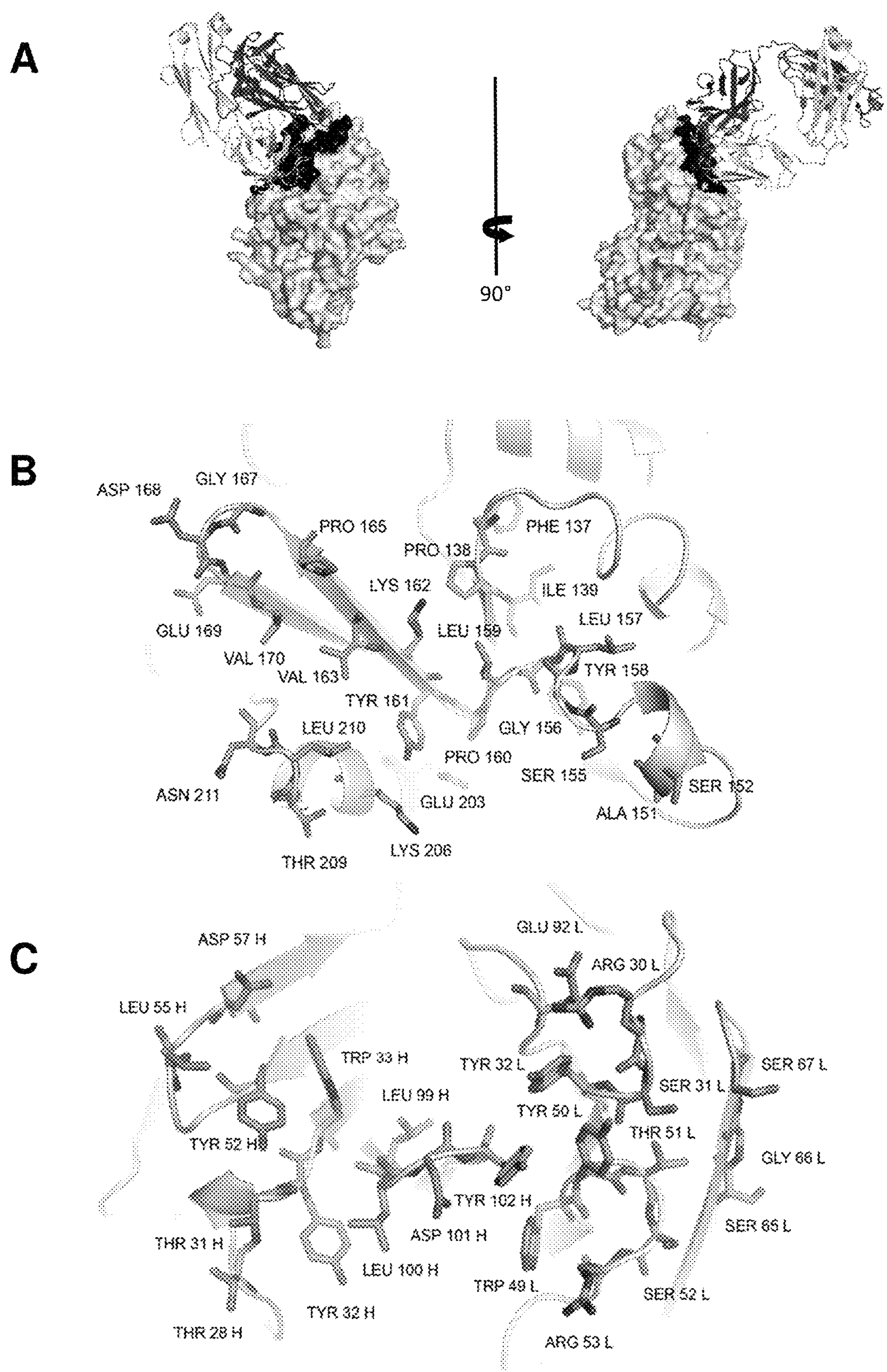
FIG. 3: Crystal structure of an anti-CD73 antibody—CD73 crystal (A) Depicted is the binding of a Fab fragment of the anti-CD73 antibody of the invention to its conformational epitope on CD73. Residues which are contacted and/or specifically bound by the Fab fragment of the inventive anti-CD73 antibody are depicted in black; $V_H$ of the Fab fragment is colored in dark grey, $V_L$ in light grey (B) enlargement of the conformational epitope shown in black in (A) which is specifically bound by the inventive antibody; amino acid residues of CD73 which are comprised in the conformational epitope are labeled using the 3-letter amino acid code; (C) amino acid residues of the heavy (H) and light (L) chain of the inventive antibody which contribute to the paratope of the Fab fragment of the inventive antibody shown in (A) which contacts and/or specifically binds to the conformational epitope depicted in (A); amino acid residues which contact and/or specifically bind to the conformational epitope on CD73 are labeled using the 3-letter amino acid code with (H) and (L) indicating heavy and light chain amino acid residues.

Proteins (Fab fragment and CD73) were complexed, purified by gel filtration and concentrated to 21 mg/ml in 10 mM Tris, 150 mM NaCl, pH=8. Crystals were obtained at 20° C. by mixing 0.2 μl of a solution containing 12% PEG8000, 0.1 M MOPS pH 7.6 and 0.1 M magnesium acetate with 0.2 μL protein solution. Plate-shaped crystals grew after 3 days. Crystals were transferred in reservoir solution supplemented with 25% PEG400 and flash frozen in liquid nitrogen. Diffraction data was collected at Swiss Light Source and the structure was solved by molecular replacement. Model building and refinement resulted in the crystal structure of the CD73:anti-CD73 Fab complex depicted in FIG. 3.

Example 11: Pharmaceutical Formulation for i.v. Administration

Any of the above antibody molecules of the invention can be selected for the manufacture of a pharmaceutical formulation for intravenous application having a composition as follows:

Drug substance: 50 mg/ml
Histidine buffer: 10 mM, pH 6.0
Sucrose: 220 mM
Polysorbate 20: 0.02

The above composition is formulated in a solution in water for injection (WFI) having the above composition, sterilized and stored at 2 to 8° C. in a 10 ml vial. The above composition can optionally be provided as a lyophilized formulation that is to be reconstituted in WFI before use.

Example 12: Pharmaceutical Use in Humans

The solutions outlined in Example 9 above is applied to a patient in need thereof, such as a human being suffering from a cancer, by intravenous infusion (dosage of 0.05 to 50.0 mg per kilogram of body weight and dose) every two to four weeks.

According to the Examples, a number of different anti-CD73 antibodies of the invention were prepared. In the following table, the sequences of these antibodies are provided. A1, A2, A3 and A4 are murine antibodies, respectively. B1, B2, C1, C2, C3, C4, C5 and C6 are humanized antibodies, respectively. The CDR sequences are provided according to the IMGT definition as described herein.

Furthermore, the sequences of the anti-PD1 antibodies of the invention are provided, which are termed PD1-1, PD1-2, PD1-3, PD1-4, and PD1-5, respectively.

TABLE 9

Amino acid sequences and SEQ ID NOs of CDRs, VH, VL, light and heavy chains of the anti-CD73 and anti-PD1 antibodies of the invention.

| SEQ ID NO: | Description | Amino acid sequence |
|---|---|---|
| 1 | A1-HCDR1 | GFTFSHYYMS |
| 2 | A1-HCDR2 | TINGGGGNTYYPDSVKD |
| 3 | A1-HCDR3 | GGPYSNYVWFAY |
| 4 | A1-LCDR1 | RASQSVTTSSYTYMH |
| 5 | A1-LCDR2 | YASNLES |
| 6 | A1-LCDR3 | QHSWENPYT |
| 7 | A2-HCDR1 | GFTFSSSYIS |
| 8 | A2-HCDR2 | WIYAGTGNTNYNQKFTD |
| 9 | A2-HCDR3 | HVNWDYFDY |
| 10 | A2-LCDR1 | KASQDVGTAVV |
| 11 | A2-LCDR2 | WASSRHT |
| 12 | A2-LCDR3 | QQYRSYPWT |
| 13 | A3-HCDR1 | GYTFTTYWMH |
| 14 | A3-HCDR2 | AIYPGNSDTTYNQKFKG |
| 15 | A3-HCDR3 | LLDYAMDY |
| 16 | A3-LCDR1 | RASQDIRNYLN |
| 17 | A3-LCDR2 | YTSRLHS |
| 18 | A3-LCDR3 | QQGNTLPWT |
| 19 | A4-HCDR1 | GLTFSSYVMS |

TABLE 9-continued

Amino acid sequences and SEQ ID NOs of CDRs, VH, VL, light and heavy chains of the anti-CD73 and anti-PD1 antibodies of the invention.

| SEQ ID NO: | Description | Amino acid sequence |
|---|---|---|
| 20 | A4-HCDR2 | TISSGGVSTYYPDTVKG |
| 21 | A4-HCDR3 | RETARATGFAY |
| 22 | A4-LCDR1 | KASQSVSNDVT |
| 23 | A4-LCDR2 | YASNRYT |
| 24 | A4-LCDR3 | QQDYSSPWT |
| 25 | B1-HCDR1 | GLTFSSYVMS |
| 26 | B1-HCDR2 | TISSGGVSTYYPDTVKG |
| 27 | B1-HCDR3 | RETARATGFAY |
| 28 | B1-LCDR1 | KASQSVSNDVT |
| 29 | B1-LCDR2 | YASNRYT |
| 30 | B1-LCDR3 | QQDYSSPWT |
| 31 | B2-HCDR1 | GLTFSSYVMS |
| 32 | B2-HCDR2 | TISSGGVSTYYPDTVKG |
| 33 | B2-HCDR3 | RETARATGFAY |
| 34 | B2-LCDR1 | KASQSVSDDVT |
| 35 | B2-LCDR2 | YASNRYT |
| 36 | B2-LCDR3 | QQDYSSPWT |
| 37 | C1-HCDR1 | GYTFTTYWMH |
| 38 | C1-HCDR2 | AIYPGFSDTTYSQKFKG |
| 39 | C1-HCDR3 | LLDYAMDY |
| 40 | C1-LCDR1 | RASQDIRSYLN |
| 41 | C1-LCDR2 | YTSRLHS |
| 42 | C1-LCDR3 | QQGETLPWT |
| 43 | C2-HCDR1 | GYTFTTYWMH |
| 44 | C2-HCDR2 | AIYPGLSDTTYSQKFKG |
| 45 | C2-HCDR3 | LLDYAMDY |
| 46 | C2-LCDR1 | RASQDIRSYLN |
| 47 | C2-LCDR2 | YTSRLHS |
| 48 | C2-LCDR3 | QQGETLPWT |
| 49 | C3-HCDR1 | GYTFTTYWMH |
| 50 | C3-HCDR2 | AIYPGLSDTTYSQKFKG |
| 51 | C3-HCDR3 | LLDYAMDY |
| 52 | C3-LCDR1 | RASQDIRSYLN |
| 53 | C3-LCDR2 | YTSRLHS |
| 54 | C3-LCDR3 | QQGETLPWT |
| 55 | C4-HCDR1 | GYTFTTYWMH |
| 56 | C4-HCDR2 | AIYPGLSDTTYNQKFKG |

TABLE 9-continued

Amino acid sequences and SEQ ID NOs of CDRs, VH, VL, light and heavy chains of the anti-CD73 and anti-PD1 antibodies of the invention.

| SEQ ID NO: | Description | Amino acid sequence |
|---|---|---|
| 57 | C4-HCDR3 | LLDYAMDY |
| 58 | C4-LCDR1 | RASQDIRSYLN |
| 59 | C4-LCDR2 | YTSRLHS |
| 60 | C4-LCDR3 | QQGETLPWT |
| 61 | C5-HCDR1 | GYTFTTYWMH |
| 62 | C5-HCDR2 | AIYPGNSDTTYNQKFKG |
| 63 | C5-HCDR3 | LLDYAMDY |
| 64 | C5-LCDR1 | RASQDIRSYLN |
| 65 | C5-LCDR2 | YTSRLHS |
| 66 | C5-LCDR3 | QQGETLPWT |
| 67 | C6-HCDR1 | GYTFTTYWMH |
| 68 | C6-HCDR2 | AIYPGNSDTTYNQKFKG |
| 69 | C6-HCDR3 | LLDYAMDY |
| 70 | C6-LCDR1 | RASQDIRNYLN |
| 71 | C6-LCDR2 | YTSRLHS |
| 72 | C6-LCDR3 | QQGNTLPWT |
| 73 | A1-VH | DVKLVESGGGLVKLGGSLKLSCVASGFTFSHYYMSWIRQTPEKRLEWV ATINGGGGNTYYPDSVKDRFTISRDNAKNTLYLQMSSLNSEDTAVYYC ARGGPYSNYVWFAYWGQGTLVTVSA |
| 74 | A1-VL | DIVLTQSPASLAVSLGQRATISCRASQSVTTSSYTYMHWYQQKPGQPP KLLIKYASNLESGVPARFSGSGSGTDFTLNIHPVEEEDTAIYYCQHSW ENPYTFGGGTKLEIK |
| 75 | A2-VH | QGQMQQSGAELVKPGTSVKLSCKTSGFTFSSSYISWLKQRPRQSLEWI AWIYAGTGNTNYNQKFTDKAQVTVDTSSSTAYMQLSSLTSEDSAIYYC ARHVNWDYFDYWGQGTTLTVSS |
| 76 | A2-VL | DIVMTQSHKFMSTSVGDRVSITCKASQDVGTAVVWYQQKPGQSPKLLI YWASSRHTGVPDRFTGSGSGTDFTLTLTNVQSEDLADYFCQQYRSYPW TFGGGTNLEIK |
| 77 | A3-VH | EVQLQQSGTVLARPGDSVKMSCKTSGYTFTTYWMHWVKQRPGQGLEWI GAIYPGNSDTTYNQKFKGKAKLTAVTSASTAYMKLSSLTNEDSAVYYC TRLLDYAMDYWGQGTSVTVSS |
| 78 | A3-VL | EIQMTQTTSSLSASLGDRVTISCRASQDIRNYLNWHQQKPDGTVKLLI WYTSRLHSGVPSRFSGSGSGTDYSLTISNLEQEDIATYFCQQGNTLPW TFGGGTKLEIK |
| 79 | A4-VH | EVQLVESGGGLVKPGGSLKLSCAASGLTFSSYVMSWVRQTPAKRLEWV ATISSGGVSTYYPDTVKGRFTISRDNAKNTLYLQMSSLMSEDTAMYYC ARRETARATGFAYWGQGTLVTVSA |
| 80 | A4-VL | SIVMTQTPKFLLVSAGDRVTITCKASQSVSNDVTWYQQKPGQSPKLLI YYASNRYTGVPDRFTGSGYGTDFTFTINTVQAEDLAVYFCQQDYSSPW TFGGGTKLEIK |
| 81 | B1-VH | EVQLVESGGGLVQPGGSLRLSCAASGLTFSSYVMSWVRQAPGKGLEWV STISSGGVSTYYPDTVKGRFTISRDNSKNTLYLQMNSLRAEDTAVYYC AKRETARATGFAYWGQGTLVTVSA |
| 82 | B1-VL | DIQMTQSPSSLSASVGDRVTITCKASQSVSNDVTWYQQKPGKAPKLLI YYASNRYTGVPSRFSGSGSGTDFTFTISSVQPEDIATYYCQQDYSSPW TFGGGTKLEIK |

TABLE 9-continued

Amino acid sequences and SEQ ID NOs of CDRs, VH, VL, light and heavy chains of the anti-CD73 and anti-PD1 antibodies of the invention.

| SEQ ID NO: | Description | Amino acid sequence |
|---|---|---|
| 83 | B2-VH | EVQLVESGGGLVQPGGSLRLSCAASGLTFSSYVMSWVRQAPGKGLEWVSTISSGGVSTYYPDTVKGRFTISRDNSKNTLYLQMNSLRAEDTAVYYCAKRETARATGFAYWGQGTLVTVSA |
| 84 | B2-VL | DIQMTQSPSSLSASVGDRVTITCKASQSVSDDVTWYQQKPGKAPKLLIYYASNRYTGVPSRFSGSGSGTDFTFTISSVQPEDIATYYCQQDYSSPWTFGGGTKLEIK |
| 85 | C1-VH | QVQLVQSGAEVKKPGDSVKVSCKASGYTFTTYWMHWVRQAPGQGLEWMGAIYPGFSDTTYSQKFKGKVTMTRDTSTSTVYMKLSSLRSEDTAVYYCARLLDYAMDYWGQGTLVTVSS |
| 86 | C1-VL | DIQMTQSPSSLSASVGDRVTITCRASQDIRSYLNWHQQKPGKAPKLLIWYTSRLHSGVPSRFSGSGSGTDYTLTISSLEPEDFATYFCQQGETLPWTFGQGTKLEIK |
| 87 | C2-VH | QVQLVQSGAEVKKPGDSVKVSCKASGYTFTTYWMHWVRQAPGQGLEWMGAIYPGLSDTTYSQKFKGKVTMTRDTSTSTVYMKLSSLRSEDTAVYYCARLLDYAMDYWGQGTLVTVSS |
| 88 | C2-VL | DIQMTQSPSSLSASVGDRVTITCRASQDIRSYLNWHQQKPGKAPKLLIWYTSRLHSGVPSRFSGSGSGTDYTLTISSLEPEDFATYFCQQGETLPWTFGQGTKLEIK |
| 89 | C3-VH | QVQLVQSGAEVKKPGDSVKVSCKASGYTFTTYWMHWVRQAPGQGLEWMGAIYPGLSDTTYSQKFKGKVTMTRDTSTSTVYMKLSSLRSEDTAVYYCARLLDYAMDYWGQGTLVTVSS |
| 90 | C3-VL | DIQMTQSPSSLSASVGDRVTITCRASQDIRSYLNWHQQKPGKAPKLLIWYTSRLHSGVPSRFSGSGSGTDYTLTISSLQPEDFATYFCQQGETLPWTFGQGTKLEIK |
| 91 | C4-VH | QVQLVQSGAEVKKPGDSVKVSCKASGYTFTTYWMHWVRQAPGQGLEWMGAIYPGLSDTTYNQKFKGKVTMTRDTSTSTVYMKLSSLRSEDTAVYYCARLLDYAMDYWGQGTLVTVSS |
| 92 | C4-VL | DIQMTQSPSSLSASVGDRVTITCRASQDIRSYLNWHQQKPGKAPKLLIWYTSRLHSGVPSRFSGSGSGTDYTLTISSLQPEDFATYFCQQGETLPWTFGQGTKLEIK |
| 93 | C5-VH | QVQLVQSGAEVKKPGDSVKVSCKASGYTFTTYWMHWVRQAPGQGLEWMGAIYPGNSDTTYNQKFKGKVTMTRDTSTSTVYMKLSSLRSEDTAVYYCARLLDYAMDYWGQGTLVTVSS |
| 94 | C5-VL | DIQMTQSPSSLSASVGDRVTITCRASQDIRSYLNWHQQKPGKAPKLLIWYTSRLHSGVPSRFSGSGSGTDYTLTISSLEPEDFATYFCQQGETLPWTFGQGTKLEIK |
| 95 | C6-VH | QVQLVQSGAEVKKPGDSVKVSCKASGYTFTTYWMHWVRQAPGQGLEWMGAIYPGNSDTTYNQKFKGKVTMTRDTSTSTVYMKLSSLRSEDTAVYYCARLLDYAMDYWGQGTLVTVSS |
| 96 | C6-VL | DIQMTQSPSSLSASVGDRVTITCRASQDIRNYLNWHQQKPGKAPKLLIWYTSRLHSGVPSRFSGSGSGTDYTLTISSLQPEDFATYFCQQGNTLPWTFGQGTKLEIK |
| 97 | A1-HC | DVKLVESGGGLVKLGGSLKLSCVASGFTFSHYYMSWIRQTPEKRLEWVATINGGGGNTYYPDSVKDRFTISRDNAKNTLYLQMSSLNSEDTAVYYCARGGPYSNYVWFAYWGQGTLVTVSAASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 98 | A1-LC | DIVLTQSPASLAVSLGQRATISCRASQSVTTSSYTYMHWYQQKPGQPPKLLIKYASNLESGVPARFSGSGSGTDFTLNIHPVEEEDTAIYYCQHSWENPYTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 9-continued

Amino acid sequences and SEQ ID NOs of CDRs, VH, VL, light and heavy chains of the anti-CD73 and anti-PD1 antibodies of the invention.

| SEQ ID NO: | Description | Amino acid sequence |
|---|---|---|
| 99 | A2-HC | QGQMQQSGAELVKPGTSVKLSCKTSGFTFSSSYISWLKQRPRQSLEWI AWIYAGTGNTNYNQKFTDKAQVTVDTSSSTAYMQLSSLTSEDSAIYYC ARHVNWDYFDYWGQGTTLTVSSASTKGPSVFPLAPSSKSTSGGTAALG CLVKDYFPEPVTVSWNSGALTSGVHTFPAVLQSSGLYSLSSVVTVPSS SLGTQTYICNVNHKPSNTKVDKRVEPKSCDKTHTCPPCPAPEAAGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKT ISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEA LHNHYTQKSLSLSPGK |
| 100 | A2-LC | DIVMTQSHKFMSTSVGDRVSITCKASQDVGTAVVWYQQKPGQSPKLLI YWASSRHTGVPDRFTGSGSGTDFTLTLTNVQSEDLADYFCQQYRSYPW TFGGGTNLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 101 | A3-HC | EVQLQQSGTVLARPGDSVKMSCKTSGYTFTTYWMHWVKQRPGQGLEWI GAIYPGNSDTTYNQKFKGKAKLTAVTSASTAYMKLSSLTNEDSAVYYC TRLLDYAMDYWGQGTSVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTI SKAKGQPREPQVYTLPPSREEMTKNQVSLTCLVKGFYPSDIAVEWESN GQPENNYKTTPPVLDSDGSFFLYSKLTVDKSRWQQGNVFSCSVMHEAL HNHYTQKSLSLSPGK |
| 102 | A3-LC | EIQMTQTTSSLSASLGDRVTISCRASQDIRNYLNWHQQKPDGTVKLLI WYTSRLHSGVPSRFSGSGSGTDYSLTISNLEQEDIATYFCQQGNTLPW TFGGGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 103 | A4-HC | EVQLVESGGGLVKPGGSLKLSCAASGLTFSSYVMSWVRQTPAKRLEWV ATISSGGVSTYYPDTVKGRFTISRDNAKNTLYLQMSSLMSEDTAMYYC ARRETARATGFAYWGQGTLVTVSAASTKGPSVFPLAPSSKSTSGGTAA LGCLVKDYFPEPVTVSWNSGALTSGVHTFPAVLQSSGLYSLSSVVTVP SSSLGTQTYICNVNHKPSNTKVDKRVEPKSCDKTHTCPPCPAPEAAGG PSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIE KTISKAKGQPREPQVYTLPPSREEMTKNQVSLTCLVKGFYPSDIAVEW ESNGQPENNYKTTPPVLDSDGSFFLYSKLTVDKSRWQQGNVFSCSVMH EALHNHYTQKSLSLSPGK |
| 104 | A4-LC | SIVMTQTPKFLLVSAGDRVTITCKASQSVSNDVTWYQQKPGQSPKLLI YYASNRYTGVPDRFTGSGYGTDFTFTINTVQAEDLAVYFCQQDYSSPW TFGGGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 105 | B1-HC | EVQLVESGGGLVQPGGSLRLSCAASGLTFSSYVMSWVRQAPGKGLEWV STISSGGVSTYYPDTVKGRFTISRDNSKNTLYLQMNSLRAEDTAVYYC AKRETARATGFAYWGQGTLVTVSAASTKGPSVFPLAPSSKSTSGGTAA LGCLVKDYFPEPVTVSWNSGALTSGVHTFPAVLQSSGLYSLSSVVTVP SSSLGTQTYICNVNHKPSNTKVDKRVEPKSCDKTHTCPPCPAPEAAGG PSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIE KTISKAKGQPREPQVYTLPPSREEMTKNQVSLTCLVKGFYPSDIAVEW ESNGQPENNYKTTPPVLDSDGSFFLYSKLTVDKSRWQQGNVFSCSVMH EALHNHYTQKSLSLSPGK |
| 106 | B1-LC | DIQMTQSPSSLSASVGDRVTITCKASQSVSNDVTWYQQKPGKAPKLLI YYASNRYTGVPSRFSGSGSGTDFTFTISSVQPEDIATYYCQQDYSSPW TFGGGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 107 | B2-HC | EVQLVESGGGLVQPGGSLRLSCAASGLTFSSYVMSWVRQAPGKGLEWV STISSGGVSTYYPDTVKGRFTISRDNSKNTLYLQMNSLRAEDTAVYYC AKRETARATGFAYWGQGTLVTVSAASTKGPSVFPLAPSSKSTSGGTAA LGCLVKDYFPEPVTVSWNSGALTSGVHTFPAVLQSSGLYSLSSVVTVP SSSLGTQTYICNVNHKPSNTKVDKRVEPKSCDKTHTCPPCPAPEAAGG |

TABLE 9-continued

Amino acid sequences and SEQ ID NOs of CDRs, VH, VL, light and heavy chains of the anti-CD73 and anti-PD1 antibodies of the invention.

| SEQ ID NO: | Description | Amino acid sequence |
|---|---|---|
| | | PSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIE KTISKAKGQPREPQVYTLPPSREEMTKNQVSLTCLVKGFYPSDIAVEW ESNGQPENNYKTTPPVLDSDGSFFLYSKLTVDKSRWQQGNVFSCSVMH EALHNHYTQKSLSLSPGK |
| 108 | B2-LC | DIQMTQSPSSLSASVGDRVTITCKASQSVSDDVTWYQQKPGKAPKLLI YYASNRYTGVPSRFSGSGSGTDFTFTISSVQPEDIATYYCQQDYSSPW TFGGGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 109 | C1-HC | QVQLVQSGAEVKKPGDSVKVSCKASGYTFTTYWMHWVRQAPGQGLEWM GAIYPGFSDTTYSQKFKGKVTMTRDTSTSTVYMKLSSLRSEDTAVYYC ARLLDYAMDYWGQGTLVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTI SKAKGQPREPQVYTLPPSREEMTKNQVSLTCLVKGFYPSDIAVEWESN GQPENNYKTTPPVLDSDGSFFLYSKLTVDKSRWQQGNVFSCSVMHEAL HNHYTQKSLSLSPG |
| 110 | C1-LC | DIQMTQSPSSLSASVGDRVTITCRASQDIRSYLNWHQQKPGKAPKLLI WYTSRLHSGVPSRFSGSGSGTDYTLTISSLEPEDFATYFCQQGETLPW TFGQGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 111 | C2-HC | QVQLVQSGAEVKKPGDSVKVSCKASGYTFTTYWMHWVRQAPGQGLEWM GAIYPGLSDTTYSQKFKGKVTMTRDTSTSTVYMKLSSLRSEDTAVYYC ARLLDYAMDYWGQGTLVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTI SKAKGQPREPQVYTLPPSREEMTKNQVSLTCLVKGFYPSDIAVEWESN GQPENNYKTTPPVLDSDGSFFLYSKLTVDKSRWQQGNVFSCSVMHEAL HNHYTQKSLSLSPG |
| 112 | C2-LC | DIQMTQSPSSLSASVGDRVTITCRASQDIRSYLNWHQQKPGKAPKLLI WYTSRLHSGVPSRFSGSGSGTDYTLTISSLEPEDFATYFCQQGETLPW TFGQGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 113 | C3-HC | QVQLVQSGAEVKKPGDSVKVSCKASGYTFTTYWMHWVRQAPGQGLEWM GAIYPGLSDTTYSQKFKGKVTMTRDTSTSTVYMKLSSLRSEDTAVYYC ARLLDYAMDYWGQGTLVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTI SKAKGQPREPQVYTLPPSREEMTKNQVSLTCLVKGFYPSDIAVEWESN GQPENNYKTTPPVLDSDGSFFLYSKLTVDKSRWQQGNVFSCSVMHEAL HNHYTQKSLSLSPG |
| 114 | C3-LC | DIQMTQSPSSLSASVGDRVTITCRASQDIRSYLNWHQQKPGKAPKLLI WYTSRLHSGVPSRFSGSGSGTDYTLTISSLQPEDFATYFCQQGETLPW TFGQGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 115 | C4-HC | QVQLVQSGAEVKKPGDSVKVSCKASGYTFTTYWMHWVRQAPGQGLEWM GAIYPGLSDTTYNQKFKGKVTMTRDTSTSTVYMKLSSLRSEDTAVYYC ARLLDYAMDYWGQGTLVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTI SKAKGQPREPQVYTLPPSREEMTKNQVSLTCLVKGFYPSDIAVEWESN GQPENNYKTTPPVLDSDGSFFLYSKLTVDKSRWQQGNVFSCSVMHEAL HNHYTQKSLSLSPG |

TABLE 9-continued

Amino acid sequences and SEQ ID NOs of CDRs, VH, VL, light and heavy chains of the anti-CD73 and anti-PD1 antibodies of the invention.

| SEQ ID NO: | Description | Amino acid sequence |
|---|---|---|
| 116 | C4-LC | DIQMTQSPSSLSASVGDRVTITCRASQDIRSYLNWHQQKPGKAPKLLI WYTSRLHSGVPSRFSGSGSGTDYTLTISSLQPEDFATYFCQQGETLPW TFGQGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 117 | C5-HC | QVQLVQSGAEVKKPGDSVKVSCKASGYTFTTYWMHWVRQAPGQGLEWM GAIYPGNSDTTYNQKFKGKVTMTRDTSTSTVYMKLSSLRSEDTAVYYC ARLLDYAMDYWGQGTLVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTI SKAKGQPREPQVYTLPPSREEMTKNQVSLTCLVKGFYPSDIAVEWESN GQPENNYKTTPPVLDSDGSFFLYSKLTVDKSRWQQGNVFSCSVMHEAL HNHYTQKSLSLSPG |
| 118 | C5-LC | DIQMTQSPSSLSASVGDRVTITCRASQDIRSYLNWHQQKPGKAPKLLI WYTSRLHSGVPSRFSGSGSGTDYTLTISSLEPEDFATYFCQQGETLPW TFGQGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 119 | C6-HC | QVQLVQSGAEVKKPGDSVKVSCKASGYTFTTYWMHWVRQAPGQGLEWM GAIYPGNSDTTYNQKFKGKVTMTRDTSTSTVYMKLSSLRSEDTAVYYC ARLLDYAMDYWGQGTLVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTI SKAKGQPREPQVYTLPPSREEMTKNQVSLTCLVKGFYPSDIAVEWESN GQPENNYKTTPPVLDSDGSFFLYSKLTVDKSRWQQGNVFSCSVMHEAL HNHYTQKSLSLSPG |
| 120 | C6-LC | DIQMTQSPSSLSASVGDRVTITCRASQDIRNYLNWHQQKPGKAPKLLI WYTSRLHSGVPSRFSGSGSGTDYTLTISSLQPEDFATYFCQQGNTLPW TFGQGTKLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 121 | PD1-1-HC | EVMLVESGGGLVQPGGSLRLSCTASGFTFSASAMSWVRQAPGKGLEWV AYISGGGGDTYYSSSVKGRFTISRDNAKNSLYLQMNSLRAEDTAVYYC ARHSNVNYYAMDYWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLG |
| 122 | PD1-1-LC | EIVLTQSPATLSLSPGERATMSCRASENIDTSGISFMNWYQQKPGQAP KLLIYVASNQGSGIPARFSGSGSGTDFTLTISRLEPEDFAVYYCQQSK EVPWTFGQGTKLEIKRTVAAPSVFIFPPSDEQLKSGTASVVCLLNNFY PREAKVQWKVDNALQSGNSQESVTEQDSKDSTYSLSSTLTLSKADYEK HKVYACEVTHQGLSSPVTKSFNRGEC |
| 123 | PD1-2-HC | EVMLVESGGGLVQPGGSLRLSCTASGFTFSASAMSWVRQAPGKGLEWV AYISGGGGDTYYSSSVKGRFTISRDNAKNSLYLQMNSLRAEDTAVYYC ARHSNPNYYAMDYWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLG |
| 124 | PD1-2-LC | EIVLTQSPATLSLSPGERATMSCRASENIDTSGISFMNWYQQKPGQAP KLLIYVASNQGSGIPARFSGSGSGTDFTLTISRLEPEDFAVYYCQQSK EVPWTFGQGTKLEIKRTVAAPSVFIFPPSDEQLKSGTASVVCLLNNFY |

TABLE 9-continued

Amino acid sequences and SEQ ID NOs of CDRs, VH, VL, light and heavy chains of the anti-CD73 and anti-PD1 antibodies of the invention.

| SEQ ID NO: | Description | Amino acid sequence |
|---|---|---|
| | | PREAKVQWKVDNALQSGNSQESVTEQDSKDSTYSLSSTLTLSKADYEK HKVYACEVTHQGLSSPVTKSFNRGEC |
| 125 | PD1-3-HC | EVMLVESGGGLVQPGGSLRLSCTASGFTFSKSAMSWVRQAPGKGLEWV AYISGGGGDTYYSSSVKGRFTISRDNAKNSLYLQMNSLRAEDTAVYYC ARHSNVNYYAMDYWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLG |
| 126 | PD1-3-LC | EIVLTQSPATLSLSPGERATMSCRASENIDVSGISFMNWYQQKPGQAP KLLIYVASNQGSGIPARFSGSGSGTDFTLTISRLEPEDFAVYYCQQSK EVPWTFGQGTKLEIKRTVAAPSVFIFPPSDEQLKSGTASVVCLLNNFY PREAKVQWKVDNALQSGNSQESVTEQDSKDSTYSLSSTLTLSKADYEK HKVYACEVTHQGLSSPVTKSFNRGEC |
| 127 | PD1-4-HC | EVMLVESGGGLVQPGGSLRLSCTASGFTFSKSAMSWVRQAPGKGLEWV AYISGGGGDTYYSSSVKGRFTISRDNAKNSLYLQMNSLRAEDTAVYYC ARHSNVNYYAMDYWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLG |
| 128 | PD1-4-LC | EIVLTQSPATLSLSPGERATMSCRASENIDVSGISFMNWYQQKPGQAP KLLIYVASNQGSGIPARFSGSGSGTDFTLTISRLEPEDFAVYYCQQSK EVPWTFGQGTKLEIKRTVAAPSVFIFPPSDEQLKSGTASVVCLLNNFY PREAKVQWKVDNALQSGNSQESVTEQDSKDSTYSLSSTLTLSKADYEK HKVYACEVTHQGLSSPVTKSFNRGEC |
| 129 | PD1-5-HC | EVMLVESGGGLVQPGGSLRLSCTASGFTFSKSAMSWVRQAPGKGLEWV AYISGGGGDTYYSSSVKGRFTISRDNAKNSLYLQMNSLRAEDTAVYYC ARHSNVNYYAMDYWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLG |
| 130 | PD1-5-LC | EIVLTQSPATLSLSPGERATMSCRASENIDVSGISFMNWYQQKPGQAP KLLIYVASNQGSGIPARFSGSGSGTDFTLTISRLEPEDFAVYYCQQSK EVPWTFGQGTKLEIKRTVAAPSVFIFPPSDEQLKSGTASVVCLLNNFY PREAKVQWKVDNALQSGNSQESVTEQDSKDSTYSLSSTLTLSKADYEK HKVYACEVTHQGLSSPVTKSFNRGEC |
| 131 | mCD73-HuFc-His6 | WELTILHTNDVHSRLEQTSDDSTKCLNASLCVGGVARLFTKVQQIRKE EPNVLFLDAGDQYQGTIWFTVYKGLEVAHFMNILGYDAMALGNHEFDN GVEGLIDPLLRNVKFPILSANIKARGPLAHQISGLFLPSKVLSVGGEV VGIVGYTSKETPFLSNPGTNLVFEDEISALQPEVDKLKTLNVNKIIAL GHSGFEMDKLIAQKVRGVDIVVGGHSNTFLYTGNPPSKEVPAGKYPFI VTADDGRQVPVVQAYAFGKYLGYLKVEFDDKGNVITSYGNPILLNSSI PEDATIKADINQWRIKLDNYSTQELGRTIVYLDGSTQTCRFRECNMGN LICDAMINNNLRHPDEMFWNHVSMCIVNGGGIRSPIDEKNNGTITWEN LAAVLPFGGTFDLVQLKGSTLKKAFEHSVHRYGQSTGEFLQVGGIHVV YDINRKPWNRVVQLEVLCTKCRVPIYEPLEMDKVYKVTLPSYLANGGD GFQMIKDELLKHDSGDQDISVVSEYISKMKVVYPAVEGRIKFSGGSGG SGGSGGSGGSGGSGGEPKSCDKTHTCPPCPAPELLGGPSVFLFPPKPK DTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPR EPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKS LSLSPGKAGSAHHHHHH |

The invention claimed is:

1. An antibody that binds specifically to CD73 comprising:

heavy chain CDRs comprising the amino acid sequence of SEQ ID NO:55 (hcCDR1), SEQ ID NO:56 (hcCDR2) and SEQ ID NO:57 (hcCDR3) and light chain CDRs comprising the amino acid sequence of SEQ ID NO:58 (lcCDR1), SEQ ID NO:59 (lcCDR2) and SEQ ID NO:60 (lcCDR3).

2. The antibody molecule of claim 1 wherein said antibody molecule is a humanized antibody molecule.

3. The antibody molecule of claim 1 or 2 wherein said antibody molecule is a monoclonal antibody molecule, Fab, $F(ab')_2$, Fv or scFv.

4. The antibody molecule of claim 1, which comprises a heavy chain constant region selected from the group consisting of IgG1, IgG2, IgG3, IgG4, IgM, IgA and IgE constant regions.

5. The antibody molecule of claim 4 wherein the heavy chain constant region is selected from the group consisting of: IgG1 and IgG1 with a L234A and/or a L235A mutation.

6. The antibody molecule of claim 1, wherein the light chain constant region is kappa or lambda.

7. The antibody molecule of claim 1, wherein said antibody molecule has a heavy chain variable region comprising an amino acid sequence at least 85% identical to SEQ ID NO: 91.

8. The antibody molecule of claim 1, wherein said antibody molecule has a heavy chain variable region comprising an amino acid sequence of SEQ ID NO: 91.

9. The antibody molecule of claim 1, wherein said antibody molecule has a light chain variable region comprising an amino acid sequence at least 85% identical to SEQ ID NO: 92.

10. The antibody molecule of claim 1, wherein said antibody molecule comprises a light chain variable region comprising the amino acid sequence of SEQ ID NO: 92.

11. The antibody molecule of claim 1, wherein said antibody molecule comprises a heavy chain comprising the amino acid sequence of SEQ ID NO: 115.

12. The antibody molecule of claim 1, wherein said antibody molecule comprises a light chain comprising the amino acid sequence of SEQ ID NO: 106, 108, 110, 112, 114, 116, 118 or 120.

13. The antibody molecule of claim 1, wherein said antibody molecule comprises a heavy chain variable region comprising the amino acid sequence of SEQ ID NO: 91 and a light chain variable region comprising the amino acid sequence of SEQ ID NO: 92.

14. The antibody molecule of claim 1, wherein said antibody molecule comprises a heavy chain comprising the amino acid sequence of SEQ ID NO: 115 and a light chain comprising the amino acid sequence of SEQ ID NO: 116.

15. An isolated nucleic acid molecule comprising a nucleic acid sequence encoding the heavy chain variable region and/or the light chain variable region of an antibody molecule of claim 1.

16. An expression vector comprising a nucleic acid molecule comprising the nucleotide sequence of claim 15.

17. A host cell comprising an expression vector of claim 16.

18. The host cell of claim 17, wherein the cell is a mammalian cell.

19. A method of manufacturing an antibody molecule of claim 1 comprising the steps of:

culturing a host cell comprising an expression vector comprising a nucleic acid molecule encoding the heavy chain variable region and/or the light chain variable region of said antibody molecule under conditions that allow formation of said antibody molecule; and, recovering said antibody molecule.

20. The method of claim 19, additionally comprising the step of further purifying and/or modifying and/or formulating said antibody molecule.

21. The method of claim 19, additionally comprising the step of formulating said antibody molecule into a pharmaceutical composition.

22. A pharmaceutical composition comprising an anti-CD73 antibody molecule of claim 1 and a pharmaceutically acceptable carrier.

23. The pharmaceutical composition of claim 22 further comprising a PD-1 antagonist.

24. A kit of parts comprising an antibody of claim 1 and a PD-1 antagonist.

25. The composition of claim 23, wherein the PD-1 antagonist is an anti-PD-1 antibody or an anti-PDL-1 antibody.

26. The composition of claim 25, wherein the PD-1 antagonist is an anti-PD-1 antibody selected from the group consisting of PDR-001, pembrolizumab, nivolumab and pidilizumab.

27. The composition of claim 25, wherein the PD-1 antagonist is an anti-PDL-1 antibody selected from the group consisting of atezolizumab, avelumab or durvalumab.

28. The composition of claim 25, wherein the PD-1 antagonist is an anti-PD-1 antibody comprising (i) a heavy chain comprising the amino acid sequence of SEQ ID NO: 121 and a light chain comprising the amino acid sequence of SEQ ID NO: 122; or (ii) a heavy chain comprising the amino acid sequence of SEQ ID NO: 123 and a light chain comprising the amino acid sequence of SEQ ID NO: 124; or (iii) a heavy chain comprising the amino acid sequence of SEQ ID NO: 125 and a light chain comprising the amino acid sequence of SEQ ID NO: 126; or (iv) a heavy chain comprising the amino acid sequence of SEQ ID NO: 127 and a light chain comprising the amino acid sequence of SEQ ID NO: 128; or (v) a heavy chain comprising the amino acid sequence of SEQ ID NO: 129 and a light chain comprising the amino acid sequence of SEQ ID NO: 130.

29. The composition of claim 22 further comprising one or more additional therapeutic agents.

30. A method of treating cancer comprising administering to a patient in need thereof a therapeutically effective amount of the antibody molecule of claim 1.

31. The method of claim 30, further comprising a PD-1 antagonist.

32. The method of claim 31 wherein the antibody molecule is to be administered simultaneously, concurrently, sequentially, successively, alternatively or separately, with the PD-1 antagonist.

33. The method of claim 31, wherein the PD-1 antagonist is an anti-PD-1 antibody or an anti-PDL-1 antibody.

34. The method of claim 33, wherein the PD-1 antagonist is an anti-PD-1 antibody selected from the group consisting of PDR-001, pembrolizumab, nivolumab and pidilizumab.

35. The method of claim 33, wherein the PD-1 antagonist is an anti-PDL-1 antibody selected from the group consisting of atezolizumab, avelumab and durvalumab.

36. The method of claim 33, wherein the PD-1 antagonist is an anti-PD-1 antibody molecule comprising (i) a heavy chain comprising the amino acid sequence of SEQ ID NO: 121 and a light chain comprising the amino acid sequence of SEQ ID NO: 122; or (ii) a heavy chain comprising the amino acid sequence of SEQ ID NO: 123 and a light chain comprising the amino acid sequence of SEQ ID NO: 124; or (iii) a heavy chain comprising the amino acid sequence of SEQ ID NO: 125 and a light chain comprising the amino acid sequence of SEQ ID NO: 126; or (iv) a heavy chain comprising the amino acid sequence of SEQ ID NO: 127 and a light chain comprising the amino acid sequence of SEQ ID NO: 128; or (v) a heavy chain comprising the amino acid sequence of SEQ ID NO: 129 and a light chain comprising the amino acid sequence of SEQ ID NO: 130.

37. The method of claim 30 wherein said cancer is selected from the group consisting of kidney cancer, gastrointestinal cancer and lung cancer.

38. The method of claim 30, wherein the antibody molecule(s) is administered in combination with one or more further therapeutic agents or procedures.

39. The method of claim 38, wherein the one or more further therapeutic agents or procedures is selected from chemotherapy, a targeted anti-cancer therapy, an oncolytic drug, a cytotoxic agent, an immune-based therapy, a cytokine, a surgical procedure, a radiation procedure, or a cellular immunotherapy.

40. The method of claim 38, wherein the further therapeutic agent is an A2AR antagonist, CD39 antagonist, LAG-3 antagonist, CTLA-4 antagonist, EGFR antagonist, or HER2 antagonist.

41. The method of claim 30, wherein the patient to be treated is selected based on increased expression of CD73.

42. The method of claim 30, wherein the patient to be treated has previously undergone treatment with another treatment agent.

43. The method of claim 37 wherein said lung cancer is non-small cell lung cancer.

44. The method of claim 42, wherein said treatment agent is a PD-1 antagonist.

45. The method of claim 44, wherein said PD-1 antagonist is selected from the group consisting of pembrolizumab, nivolumab, pidilizumab, atezolizumab, avelumab, durvalumab and an antibody comprising (i) a heavy chain comprising the amino acid sequence of SEQ ID NO: 121 and a light chain comprising the amino acid sequence of SEQ ID NO: 122; or (ii) a heavy chain comprising the amino acid sequence of SEQ ID NO: 123 and a light chain comprising the amino acid sequence of SEQ ID NO: 124; or (iii) a heavy chain comprising the amino acid sequence of SEQ ID NO: 125 and a light chain comprising the amino acid sequence of SEQ ID NO: 126; or (iv) a heavy chain comprising the amino acid sequence of SEQ ID NO: 127 and a light chain comprising the amino acid sequence of SEQ ID NO: 128; or (v) a heavy chain comprising the amino acid sequence of SEQ ID NO: 129 and a light chain comprising the amino acid sequence of SEQ ID NO: 130.

* * * * *